United States Patent
Yellen et al.

(10) Patent No.: US 11,420,204 B2
(45) Date of Patent: Aug. 23, 2022

(54) PLATFORMS FOR SINGLE CELL ANALYSIS

(71) Applicant: Duke University, Durham, NC (US)

(72) Inventors: Benjamin B. Yellen, Durham, NC (US); Roozbeh Abedini-Nassab, Durham, NC (US); Korine A. Ohiri, Durham, NC (US); David M. Murdoch, Durham, NC (US); Kris Wood, Durham, NC (US)

(73) Assignee: Duke University, Durham, NC (US)

( * ) Notice: Subject to any disclaimer, the term of this patent is extended or adjusted under 35 U.S.C. 154(b) by 524 days.

(21) Appl. No.: 16/066,089

(22) PCT Filed: Jan. 12, 2017

(86) PCT No.: PCT/US2017/013103
§ 371 (c)(1),
(2) Date: Jun. 26, 2018

(87) PCT Pub. No.: WO2017/123697
PCT Pub. Date: Jul. 20, 2017

(65) Prior Publication Data
US 2020/0269246 A1 Aug. 27, 2020

Related U.S. Application Data

(60) Provisional application No. 62/377,856, filed on Aug. 22, 2016, provisional application No. 62/296,138, (Continued)

(51) Int. Cl.
*B01L 3/00* (2006.01)
*G01N 33/543* (2006.01)
*G01N 33/48* (2006.01)

(52) U.S. Cl.
CPC .......... *B01L 3/502761* (2013.01); *G01N 33/54326* (2013.01); *B01L 2200/0668* (2013.01);
(Continued)

(58) Field of Classification Search
CPC ..... B01L 2200/0668; B01L 2300/0816; B01L 2300/0864; B01L 2400/043;
(Continued)

(56) References Cited

U.S. PATENT DOCUMENTS 6,568,052 B1   5/2003   Rife et al.
2006/0223185 A1*  10/2006  Fedorov .............. C12N 13/00
                                                                435/461
2015/0064764 A1   3/2015   Kim et al.
(Continued)

FOREIGN PATENT DOCUMENTS

WO   2007041671 A2   4/2007

OTHER PUBLICATIONS

International Preliminary Report on Patentability and Written Opinion issued in PCT Application No. PCT/US2017/013103 dated Jul. 17, 2018. (ten (10) pages.

International Search Report and Written Opinion dated Jun. 7, 2017 from related International Application No. PCT/US2017/013103. 15 pages.

(Continued)

*Primary Examiner* — Dean Kwak
(74) *Attorney, Agent, or Firm* — Olive Law Group, PLLC

(57) ABSTRACT

Provided herein are devices, systems, and methods for analysis of objects, such as cells. The devices, systems, and methods organize a plurality of objects in a plurality of partitions by trapping an object in a trap and transferring the
(Continued)

object to an adjacent partition. The devices, systems, and methods provide for parallel analysis of a plurality of objects.

7 Claims, 79 Drawing Sheets

Related U.S. Application Data filed on Feb. 17, 2016, provisional application No. 62/278,148, filed on Jan. 13, 2016.

(52) U.S. Cl.
CPC ............ *B01L 2300/0816* (2013.01); *B01L 2300/0864* (2013.01); *B01L 2300/0893* (2013.01); *B01L 2400/043* (2013.01); *B01L 2400/0436* (2013.01); *B01L 2400/0487* (2013.01)

(58) Field of Classification Search
CPC ....... B01L 3/502761; B01L 2400/0427; B01L 3/502715; B01L 2200/0652; B01L 2300/0867; B01L 2400/0436; B01L 2200/027; B01L 2200/0647; B01L 2400/0487; G01N 33/54326; G01N 2035/00158

See application file for complete search history.

(56) References Cited

U.S. PATENT DOCUMENTS

| 2015/0151298 A1 | 6/2015 | Hobbs et al. |
| 2016/0199837 A1* | 7/2016 | Breinlinger ....... B01L 3/502761 435/308.1 |

OTHER PUBLICATIONS

Lin, S et al. "Single Cell Manipulation Technology" Nano Biomedical Engineering. vol. 7, Issue 3, Jul. 24, 2015. pp. 75-91. Doi: 10.5101/nbe.v7i3.p75-91.

Lim, B et al. "Magnetophoretic Circuits for Digital Control of Single Particles and Cells" Nature Communications vol. 5, Issue 14, May 14, 2014; Doi:10.1038/ncomms4846.

Khalili, A et al. "Numerical Analysis of Hydrodynamic Flow in Microfluidic Biochip for Single-Cell Trapping Application" International Journal of Molecular Sciences.

* cited by examiner

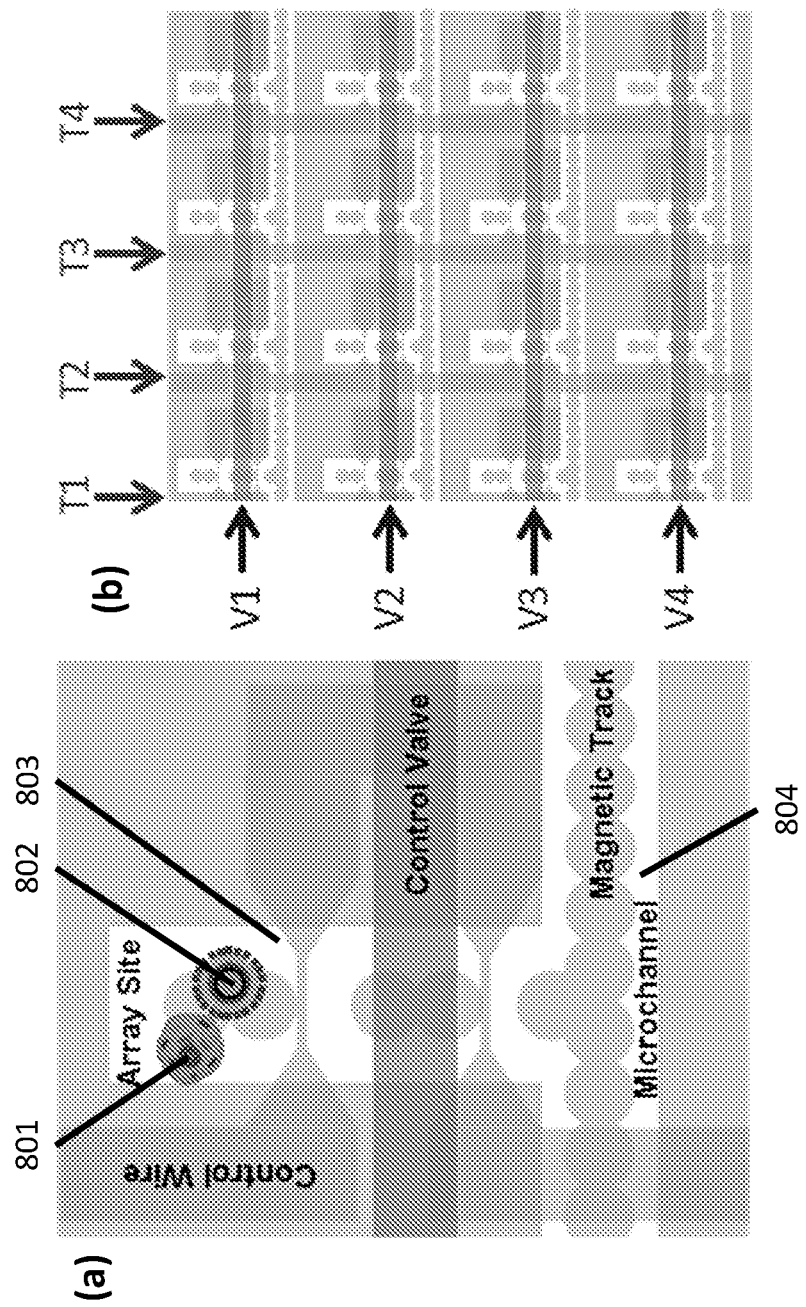
Fig. 8a-b

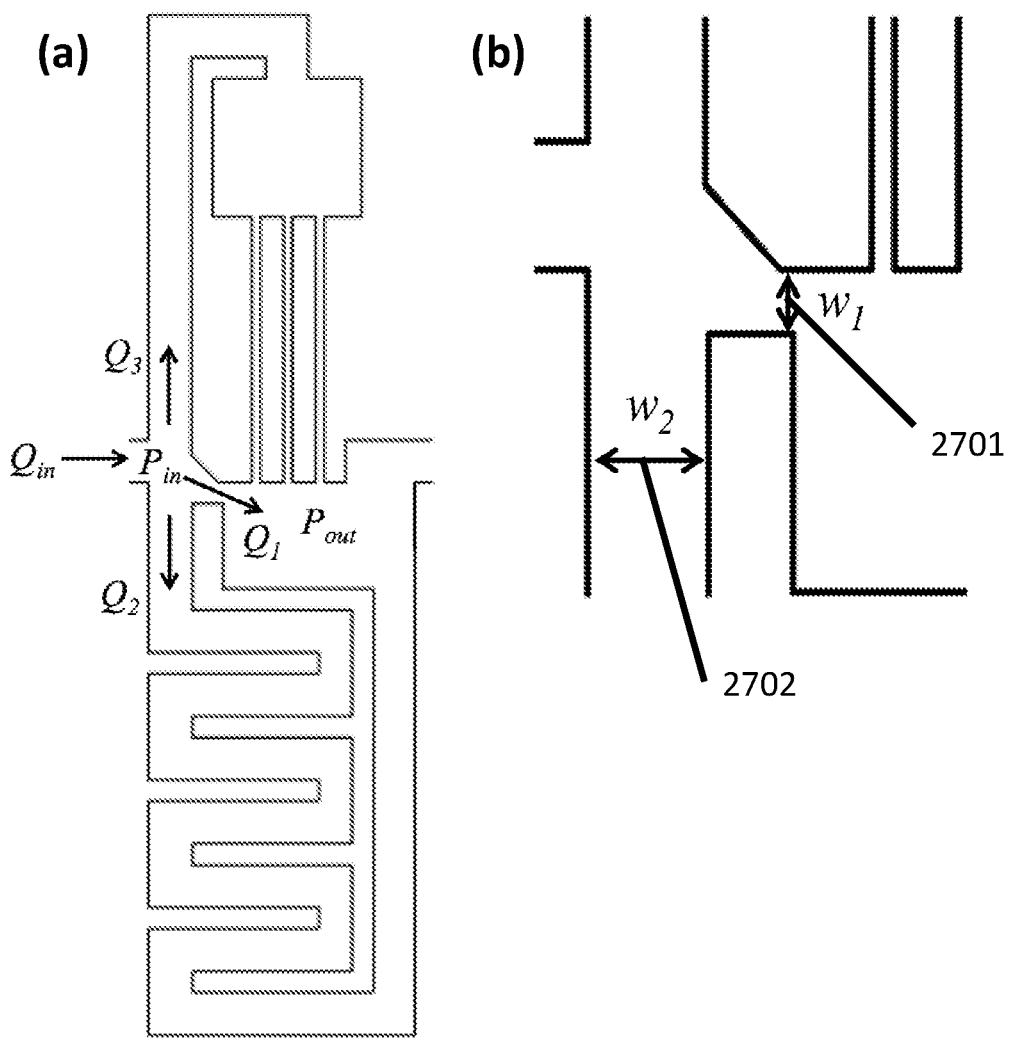
Fig. 27a-b

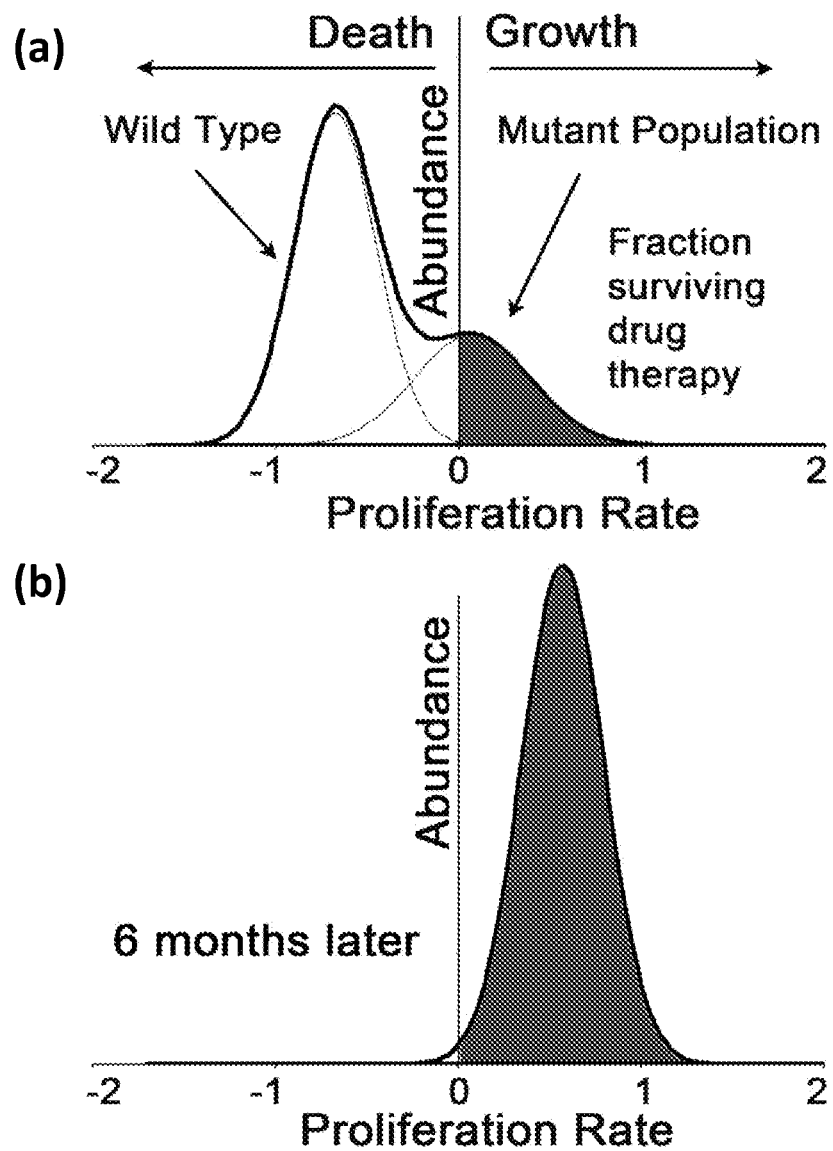
Fig. 30a-b

Step 1. Capture Single
Cells in Fluidic Traps
(Acoustics OFF)

Fluidic trapping of single cells

Step 1. Capture Single
Cells in Fluidic Traps
(Acoustics OFF)

Zoom in of fluid trap site

Step 2. Transfer of single cells into microchambers (Acoustics ON)

Step 2. Transfer of single cells into microchambers (Acoustics ON)

PLATFORMS FOR SINGLE CELL ANALYSIS

CROSS REFERENCE

This is a 371 national stage patent application claims priority to PCT International Patent Application No. PCT/US2017/013103, filed Jan. 12, 2017, and titled PLATFORMS FOR SINGLE CELL ANALYSIS, which claims priority to U.S. Provisional Application No. 62/278,148, filed Jan. 13, 2016; U.S. Provisional Patent Application No. 62/296,138, filed Feb. 17, 2016; and U.S. Provisional Patent Application No. 62/377,856, filed Aug. 22, 2016; the disclosures of which are incorporated herein in their entireties.

STATEMENT AS TO FEDERALLY SPONSORED RESEARCH

This invention was made with the support of the United States government under Federal Grant No. P30 A1027767 awarded by the Creative and Novel Ideas in Research (CNIHR) Program of the National Institute of Allergy and Infectious Diseases (NIAID), as well as Grant No. 5R21GM111584, and Grant No. 1R56-AI112360. The government has certain rights in the invention.

BACKGROUND

Rare cells are implicated in the pathogenesis of diverse human disease. For example, rare immune cells harboring latent viral reservoirs make it difficult to fully cure HIV infected patients, and rare drug resistant cancer cells similarly limit the curative potential of chemotherapies. Existing single cell analysis platforms are impeded by low-throughput, high-cost, and incomplete characterization of cellular behavior.

SUMMARY

An aspect of the present disclosure provides a method may comprise capturing an object in a trap and transferring the object from the trap into a partition. In some cases, the trap may be formed therein a microfluidic device. In some cases, the partition may be adjacent thereto the trap and formed therein the microfluidic device. In some cases, after the transferring, the trap may be available to trap an additional object. In some cases, a width of the partition may be from about 20 micrometers (um) to about 200 um. In some cases, a width of the partition may be less than about 150 um.

In some cases, the object may comprise a cell or fragment thereof, a bead, a liquid droplet, an embryo or fragment thereof, an organism, or any combination thereof. In some cases, the object may be the cell, and the cell may be an adherent or non-adherent eukaryotic cell. In some cases, the object may be the cell, and the cell may be selected from the group consisting of: an adherent prokaryotic cell, a non-adherent prokaryotic cell, a yeast cell, a bacterial cell, an algae cell, a fungal cell and any combination thereof. In some cases, the object may be the bead and the bead may be a magnetic bead. In some cases, the object may be the liquid droplet. In some cases, the bead may be conjugated to an antibody or fragment thereof, an enzyme, a receptor, a protein or fragment thereof, a polysaccharide, a lipid, a peptide, a small molecule, a nucleic acid or fragment thereof, an oligonucleotide or fragment thereof, or any combination thereof.

In some cases, a volume of the partition may be about 100 picoliters. In some cases, a width and a length of the partition may be equivalent to a monolayer of from 1 to about 10 cells. In some cases, a distance from the trap to the partition adjacent thereto may be from about 20 um to about 200 um. In some cases, the trap may be a hydrodynamic trap. In some cases, the additional object may be an additional cell or fragment thereof or an additional bead.

In some cases, the method may further comprise, after the transferring, trapping an additional object in the trap and transferring the additional object into the partition. In some cases, the transferring may employ a transfer mechanism selected from the group consisting of: a magnetic mechanism, an acoustic mechanism, an electric mechanism, an optical mechanism, an optoelectronic mechanism, a gravitational mechanism, a centrifugal acceleration mechanism, and any combination thereof. In some cases, the transferring may employ one or more magnets and a magnetic track. In some cases, the transferring may employ an acoustic track, an electric track, or an optoelectronic track. In some cases, the partition may comprise structural resonance features and the transferring may employ an acoustic energy. In some cases, the acoustic energy may be generated by a piezoelectric transducer. In some cases, the piezoelectric transducer may comprise quartz, lead zirconium titanate, barium titanate, zinc oxide, lithium niobate, lithium tantalate, lanthanum gallium silicate, or any combination thereof. In some cases, the transferring may employ a laser trap. In some cases, the transferring may employ a gravitational sedimentation force applied to the microfluidic device or the transferring may employ a centrifugal force applied to the microfluidic device.

Another aspect of the present disclosure provides a method of organizing a plurality of objects on a microfluidic device. The method may comprise populating one or more traps of a plurality of traps formed therein a microfluidic device with at least a portion of the plurality of objects and collectively transferring a plurality of captured objects into a plurality of partitions. In some cases, an object may be captured in a trap. In some cases, a majority of partitions may be adjacent thereto a trap. In some cases, greater than about 1,000 partitions may be populated with at least one object by performing a collective transfer. In some cases, at least about 5,000 objects may be collectively transferred into partitions by performing a collective transfer. In some cases, the plurality of objects may comprise cells or fragments thereof, beads, or a combination thereof. In some cases, the plurality of objects may comprise cells or fragments thereof and the cells may comprise an adherent eukaryotic cell or a non-adherent eukaryotic cell. In some cases, the plurality of objects may be greater than about 30,000 objects. In some cases, the plurality of objects may be greater than about 100,000 objects. In some cases, the plurality of objects may comprise cells or fragments thereof and the cells or fragments thereof may be collectively transferred along an acoustic track. In some cases, the plurality of objects may comprise cells or fragments thereof and the cells or fragments thereof may be collectively transferred along an electric track. In some cases, the plurality of objects may comprise cells or fragments thereof and the cells or fragments thereof may be collectively transferred along an optoelectronic track. In some cases, the plurality of objects may comprise cells or fragments thereof and the transferring may comprise applying a gravitational sedimentation force to the microfluidic device or applying a centrifugal force to the microfluidic device. In some cases, the plurality of objects may comprise beads and the beads may be collectively transferred along a magnetic track. In some cases, the plurality of objects may comprise cells adhered to particles and the cells may be collectively transferred along a magnetic track.

In some cases, a volume of a partition of the plurality of partitions may be from about 50 picoliters to about 500 picoliters. In some cases, a volume of a partition of the plurality of partitions may accommodate from about 2 to about 1000 cells. In some cases, a volume of a partition of the plurality of partitions may accommodate at least about 6 cell doublings. In some cases, a distance from a trap of the plurality of traps to a partition adjacent thereto may be from about 20 micrometers to about 1000 micrometers. In some cases, after the collectively transferring, an object occupancy rate for the plurality of partitions may be greater than about 90%. In some cases, a movement of the plurality of captured objects during the collectively transferring may have a precision of at least about +/−2 micrometers.

In some cases, the one or more traps may be hydrodynamic traps. In some cases, the plurality of traps may be hydrodynamic traps. In some cases, after the collectively transferring, each partition of the plurality of partitions may comprise an object. In some cases, at least two objects of the plurality of objects may be transferred into a partition. In some cases, the populating further may comprise flowing a fluid along a path adjacent thereto at least one partition of the plurality of partitions. In some cases, at least a portion of the plurality of partitions may further comprise at least one hydrodynamic trap. In some cases, the at least one hydrodynamic trap may permit the fluid to flow through the at least one hydrodynamic trap. In some cases, the collectively transferring may further comprise flowing the fluid within the at least a portion of the plurality of partitions.

In some cases, may further comprise phenotyping the plurality of objects. In some cases, the phenotyping may comprise determining a cell proliferation, a cell morphology, a cell motility, an expression level of a protein or fragment thereof or a nucleic acid or fragment thereof, a subcellular localization of a protein or fragment thereof or a nucleic acid or fragment thereof, a viral shedding, a viral secretion, a protein secretion, a transcriptional profile, or any combination thereof.

In some cases, the method may further comprise contacting an identifier to an object of the plurality of objects. In some cases, the contacting may occur during the collectively transferring or after the object may be transferred to a partition. In some cases, the identifier may be a known identifier. In some cases, the identifier may be a unique identifier. In some cases, the method may further comprise pooling at least a portion of the plurality of objects. In some cases, an identity of the identifier may be known or may be deciphered prior to the pooling. In some cases, the contacting may be based on a determination of an object phenotype such that a particular identifier may correspond to a particular object phenotype. In some cases, the plurality of traps may comprise at least about 5,000 traps. In some cases, a volumetric flow rate through an unoccupied hydrodynamic trap may be substantially higher than the volumetric flow through an occupied hydrodynamic trap such that no more than an object may occupy a hydrodynamic trap at one time. In some cases, the method may further comprise controlling one or more conditions of a partition independently from the remaining partitions. In some cases, a phenotype of an object within the partition may be determined. In some cases, the one or more conditions may be selected from the group consisting of a temperature within a partition, a fluid composition within a partition, a bead content within a partition, a cellular content within a partition, or any combination thereof.

Another aspect of the present disclosure provides a method comprising fluidically capturing an object at a trap location on a microfluidic device and non-fluidically transferring the object from the trap location into a section of a partition adjacent thereto the trap location. In some cases, the partition may be formed therein the microfluidic device. In some cases, the trap location may be a hydrodynamic trap. In some cases, the object may comprise a cell or fragment thereof, a bead, a liquid droplet, an embryo or fragment thereof, an organism, or any combination thereof. In some cases, the object may be the cell and the cell may be an adherent or non-adherent eukaryotic cell. In some cases, the object may be the bead and the bead may be a magnetic bead. In some cases, a volume of the partition may be from about 50 picoliters to about 500 picoliters. In some cases, after the non-fluidically transferring, the trap location may be available to capture an additional object. In some cases, the additional object may be a cell or fragment thereof or a bead.

In some cases, after the non-fluidically transferring, the method may further comprise (i) trapping an additional object in the trap location and (ii) transferring the additional object into the partition. In some cases, the non-fluidically transferring may comprise a transfer mechanism selected from the group consisting of: a magnetic mechanism, an acoustic mechanism, an electric mechanism, an optical mechanism, an optoelectronic mechanism, and any combination thereof. In some cases, the non-fluidically transferring may comprise one or more magnets and a magnetic track. In some cases, the non-fluidically transferring may comprise an acoustic track an electric track, an optoelectronic track, or any combination thereof. In some cases, the non-fluidically transferring may comprise applying a gravitational sedimentation force, a centrifugal force, or a combination thereof to the microfluidic device. In some cases, a volumetric flow through an unoccupied hydrodynamic trap may be substantially higher than a volumetric flow through an occupied hydrodynamic trap such that no more than one object may occupy the hydrodynamic trap at one time. In some cases, the object may be non-fluidically transferred into the partition when a volumetric flow rate through the partition may be substantially smaller than a volumetric flow through an unoccupied trap. In some cases, a volumetric flow within the partition may direct the object to a different section of the partition. In some cases, a distance from the trap location to the partition adjacent thereto may be from about 20 micrometers to about 200 micrometers.

Another aspect of the present disclosure provides a microfluidic device that may comprise a path configured to receive a plurality of objects, a trap adjacent thereto to the path and configured for occupancy of an object of the plurality of objects, a partition adjacent thereto the trap, and a transfer mechanism selected from the group consisting of: a magnetic mechanism, an acoustic mechanism, an electric mechanism, an optical mechanism, an optoelectronic mechanism, a gravitational mechanism, a centrifugal acceleration mechanism, and any combination thereof, positioned adjacent thereto the trap and the partition. In some cases, the object may transfer between the trap and the partition.

Another aspect of the present disclosure provides a microfluidic device that may comprise a path configured to receive a plurality of objects, a trap adjacent thereto the path and configured for occupancy of an object of the plurality of objects, a partition adjacent thereto the trap, and a non-fluidic transfer mechanism positioned adjacent thereto the trap and the partition. In some cases, the non-fluidic transfer mechanism may transfer the object between the trap and a section of the partition.

In some cases, the trap may be a hydrodynamic trap, a bubble trap, an optical trap, a trident trap, a physical barrier trap, a magnetic trap, an acoustic trap, a laser trap, or any combination thereof. In some cases, the partition may be a plurality of partitions. In some cases, a packing density of partitions of the plurality of partitions may be greater than about 1,000 partitions per square centimeter of the microfluidic device. In some cases, an outer length and an outer width of the microfluidic device may be less than about 8 inches (in) by less than about 8 in. In some cases, the transfer mechanism may comprise an inside track for the object to transfer between the trap and the partition adjacent thereto and an outside track for the object to transfer between the partition adjacent thereto and the trap. In some cases, the inside track and the outside track may be different. In some cases, the transfer mechanism may be an acoustic track. In some cases, a width of the partition may be from about 20 micrometers to about 200 micrometers. In some cases, a width of the partition may be less than about 150 um. In some cases, a volume of the partition may be from about 50 picoliters to about 500 picoliters.

In some cases, the plurality of objects may comprise a cell or fragment thereof, a bead, a liquid droplet, an embryo or fragment thereof, an organism, or any combination thereof. In some cases, the plurality of objects may comprise cells or fragments thereof and a volume of the partition may be equivalent to a volume of at least about 40 cells. In some cases, a volume of the partition may accommodate at least about 6 cell doublings.

In some cases, the partition may be a plurality of partitions. In some cases, the plurality of partitions may be at least about 5,000 partitions. In some cases, a packing density of the partitions in the plurality of partitions may be greater than about 1,000 partitions per square centimeter of the microfluidic device. In some cases, the plurality of objects may comprise at least about 100,000 objects. In some cases, the plurality of objects may comprise at least about 10,000 objects. In some cases, the plurality of objects may comprise at least about 20,000 objects. In some cases, the plurality of objects may comprise at least about 30,000 objects. In some cases, the plurality of objects may comprise at least about 50,000 objects.

In some cases, the microfluidic device may further comprise an electrical conductor. In some cases, the electrical conductor may produce a magnetic field. In some cases, a thickness of the electrical conductor may be at least about 100 nanometers. In some cases, the trap may be the hydrodynamic trap and the hydrodynamic trap may provide a hydrodynamic resistance less than about $10^{15}$ Newton*second per meter$^\wedge$5 (Ns/m$^5$). In some cases, the electrical conductor may comprise a gold, silver, a platinum, a copper, or any combination thereof. In some cases, a surface of the path, the trap, the partition, or any combination thereof may comprise a polyethylene glycol, a poly[oligo(ethylene glycol) methyl ether methacrylate], a zwitterionic polymer comprising carboxybetaine or sulfobetaine, a polytetrafluoroethylene or other fluoropolymer, or any combination thereof.

In some cases, the microfluidic device may further comprise one or more sensors. In some cases, the one or more sensors may comprise an optical sensor, an electrochemical sensor, an optoelectronic sensor, a piezoelectric sensor, a capacitance sensor, a magnetic sensor, a biosensor, a chemical sensor, a pressure sensor, or any combination thereof. In some cases, the one or more sensors may measure a temperature, a pH, a volume of a liquid, a concentration of a compound, a change in a concentration of a compound, or any combination thereof.

In some cases, the compound may be an ion, a gas, a nutrient or fragment thereof, a buffer, a drug or fragment thereof, a protein or fragment thereof, a ligand or fragment thereof, a hormone or fragment thereof, a cytokine or fragment thereof, a chemokine or fragment thereof, a growth factor or fragment thereof, a carbohydrate or fragment thereof, a lipid or fragment thereof, a nucleic acid or fragment thereof, a cDNA, an siRNA, an shRNA, a microRNA, an sgRNA, an mRNA, a virus or fragment thereof, a retrovirus or fragment thereof, a lentivirus or fragment thereof, a kinase or fragment thereof, an enzyme or fragment thereof, an antibody or fragment thereof, an aptamer or fragment thereof, an antigen or fragment thereof, a micelle, a nanoparticle, a liposome, a microparticle, a lysis buffer, or any combination thereof. In some cases, the compound may be the ion and the ion may be $Ca^{2+}$, $Mg^{2+}$, or a combination thereof. In some cases, the compound may be the gas and the gas may be oxygen, carbon dioxide, or a combination thereof. In some cases, the compound may be the nutrient and the nutrient may be glucose, an amino acid, or combinations thereof. In some cases, each chamber of the plurality of chambers may comprise at least one sensor. In some cases, the microfluidic device may further comprise a control module to direct the one or more sensors to make one or more measurements.

Another aspect of the present disclosure provides a system for organizing a plurality of objects on a microfluidic device. The system may comprise a) a control module, and b) the microfluidic device comprising: a plurality of paths; a plurality of traps, a plurality of partitions, and a plurality of transfer mechanisms. In some cases, the transfer mechanism may be positioned adjacent thereto the at least one trap and the partition. In some cases, the control module may direct the transfer of the object between the at least one trap and the partition. In some cases, each trap may be adjacent thereto at least one path and may be configured for occupancy of an object. In some cases, a partition may be adjacent thereto at least one trap. In some cases, a transfer mechanism may be selected from the group consisting of: a magnetic mechanism, an acoustic mechanism, an electrical mechanism, an optoelectronic mechanism, an optical mechanism, a gravitational mechanism, a centrifugal acceleration mechanism, or any combination thereof.

Another aspect of the present disclosure provides a system for organizing a plurality of objects on a microfluidic device. The system may comprise a) a control module, and b) the microfluidic device comprising: a plurality of paths; a plurality of traps, a plurality of partitions, and a plurality of non-fluidic transfer mechanisms. In some cases, a partition may be adjacent thereto at least one trap. In some cases, a transfer mechanism may be positioned adjacent thereto the at least one trap and the partition. In some cases, the control module may direct the non-fluidic transfer of the object between the at least one trap and the partition. In some cases, each trap may be adjacent thereto at least one path and may be configured for occupancy of an object.

Another aspect of the present disclosure provides a system for organizing a plurality of objects on a microfluidic device. The system may comprise a) a control module, and b) the microfluidic device comprising: a plurality of paths; a plurality of traps, a plurality of partitions, and a plurality of transfer mechanisms. In some cases, a transfer mechanism may be positioned adjacent thereto the at least one trap and the partition. In some cases, the control module may direct collective transfer of the plurality of objects between the plurality of traps and the plurality of partitions. In some cases, the control module may direct selective transfer of at least a subset of the plurality of objects between the plurality of traps and the plurality of partitions. In some cases, each trap may be adjacent thereto at least one path and may be configured for occupancy of an object. In some cases, a partition may be adjacent thereto at least one trap.

In some cases, the system may further comprise an imaging module. In some cases, the imaging module may measure one or more parameters and may deliver the one or more parameters to the control module. In some cases, the transfer mechanism may be the magnetic mechanism. In some cases, the system may comprise at least one magnetic material adjacent thereto or formed therein the microfluidic device. In some cases, the transfer mechanism may be the magnetic mechanism. In some cases, the magnetic mechanism may comprise a source of magnetic field produced from an external controller, a source of magnetic field produced from a magnetic track inside the partition or a combination thereof. In some cases, a speed that the magnetic object travels along the magnetic track may be from about 1 micrometer per second (um/sec) to about 100 um/sec. In some cases, the transfer mechanism may be the magnetic mechanism. In some cases, the control module may direct application of an external rotating field to a portion of the microfluidic device. In some cases, the control module may direct a supply of heat from at least one heating element to the microfluidic device such that a set temperature may be matched. In some cases, the set temperature may be input to the control module by a user. In some cases, the object may be a cell and the cell may be cultured in the partition for at least about 1 day.

Another aspect of the present disclosure provides a method for evaluating a plurality of second objects. The method may comprise (a) organizing a plurality of first objects into a plurality of partitions of the microfluidic device, (b) identifying an identity of a portion of first objects of the plurality of first objects, (c) organizing a plurality of second objects into the plurality of partitions, (d) associating at least one second object of the plurality of second objects with at least one first object of the plurality of first objects, and (e) removing the plurality of first objects from the microfluidic device. In some cases, the plurality of first objects may be a plurality of beads and the plurality of second objects may be a plurality of cells. In some cases, the method may further comprise lysing the at least one cell and reverse transcribing RNA from the lysed cell onto a bead. In some cases, the lysing and the reverse transcribing may be after (d). In some cases, the method may further comprise adding a drug or salt thereof or a vehicle control to at least one partition of the plurality of partitions. In some cases, the adding may be after (d).

In some cases, the method may identify a drug-resistant cell in the plurality of cells. In some cases, the method may identify a therapeutic compound for a disease or condition. In some cases, the disease or condition may be cancer. In some cases, the disease or condition may be an immunological disease, an infectious disease, a neurological disease, or a combination thereof. In some cases, the plurality of beads may comprise unique barcode sequences. In some cases, the identifying may further comprise exposing the plurality of first objects, the plurality of second objects, or a combination thereof to a set of sequencing reagents, performing a series of synthesis reactions, and determining an identify of each of the unique barcode sequences during (c). In some cases, the unique barcode sequences may comprise fluorescent barcodes.

In some cases, at least a portion of the method may be automated. In some cases, greater than about 1,000 cells may be evaluated in parallel. In some cases, the bead may be a magnetic bead. In some cases, a barcode may be attached to a bead of the plurality of beads. In some cases, the barcode may comprise a DNA sequence. In some cases, the DNA sequence may be a unique DNA sequence. In some cases, a length of the barcode may be at least about 10 basepairs (bp). In some cases, the barcode may be mapped to a cell phenotype. In some cases, following the adding, a level of a cellular protein, a level of a phosphoprotein, a degree of protein localization, a level of an organelle function, or any combination thereof, may be measured using a fluorescence-based assay.

In some cases, the plurality of first objects may comprise beads. In some cases, the beads may be conjugated to antibodies, cytokine-specific antibodies, chemokine-specific antibodies, growth factor-specific antibodies enzymes, enzyme substrates, proteins, small molecules, glycoproteins, drug molecules, polysaccharides, fluorophores, oligonucleotides, oligonucleotide barcodes, or any combination thereof. In some cases, the plurality of first objects may comprise beads. In some cases, the beads may be conjugated to a molecule that adheres to an outer membrane of a virus particle. In some cases, the method may further comprise determining a level of the virus particle in each of the plurality of partitions.

In some cases, the method may further comprise introducing at least a second plurality of objects into the microfluidic device and sorting the at least second plurality of objects into the plurality of partitions. In some cases, the at least second plurality of objects may comprise at least a second plurality of cells of the same cell type or a different cell type so as to sort a homogeneous set or a heterogeneous set of two or more cells into each partition. In some cases, the heterogeneous set of two or more cells may comprise immune cells and the method may be used to analyze immunological interactions. In some cases, the heterogeneous set of two or more cells may comprise immune cells, cancer cells, or a combination thereof and the method may be used to study immune surveillance or immunotherapies. In some cases, the heterogeneous set of two or more cells may comprise neuron cells, muscle cells, or a combination thereof and the method may be used to study the formation of neuromuscular junctions. In some cases, the heterogeneous set of two or more cells may comprise neuron cells, glial cells, astrocytes, or any combination thereof and the method may be used to study neuronal signaling and/or drug-dependence. In some cases, the heterogeneous set of two or more cells may comprise tumor cells, endothelial cells, epithelial cells, macrophages, neutrophils, NK cells, fibroblasts, stromal cells, smooth muscle cells, adipocytes, or any combination thereof and the method may be used to study a tumor microenvironment. In some cases, the homogeneous set or the heterogeneous set of two or more cells may comprise a pair of adherent cells and adhesion between the pair of adherent cells may be studied. In some cases, the heterogeneous set of two or more cells may comprise an immune cell and a pathogen and an interaction between the immune cell and the pathogen may be analyzed. In some cases, the heterogeneous set of two or more cells may comprise a leukocyte and an endothelial cell and an interaction between the leukocyte and the endothelial cell may be analyzed. In some cases, the heterogeneous set of two or more cells may comprise a pair of cells and the pair of cells may be used to analyze a tight junction, a gap junction, a junction involving direct contact between membranes of the pair of cells, or any combination thereof.

In some cases, the method may further comprise selectively transferring a portion of objects from their respective partition to an outlet port of the microfluidic device. In some cases, the method may further comprise collectively transferring objects from their respective partition to an outlet port of the microfluidic device. In some cases, the selective transferring may comprise reversing a fluid flow or employing a magnetic mechanism, an electric mechanism, an acoustic mechanism, a centrifugal mechanism, a gravitational mechanism, or any combination thereof. In some cases, the collective transferring may comprise reversing a fluid flow or employing a magnetic mechanism, an electric mechanism, an acoustic mechanism, a centrifugal mechanism, a gravitational mechanism, or any combination thereof. In some cases, the method may further comprise destroying a portion of objects in their respective partitions, and transferring an undestroyed portion of objects to an outlet port of the microfluidic device. In some cases, the destroying may comprise employing a laser, increasing or decreasing a local temperature, adding a local buffer, or any combination thereof.

In some cases, the acoustic mechanism may be an acoustic source that provides a standing acoustic wave to the microfluidic device. In some cases, a frequency of the standing acoustic wave may be from about 1 MHz to about 20 MHz.

In some cases, the acoustic mechanism may be an acoustic source that may be configured to provide acoustic streaming to the microfluidic device. In some cases, a frequency of the acoustic streaming may be from about 1 kHz to about 2000 kHz. In some cases, a frequency of the acoustic streaming may be associated with an acoustic wavelength that may be larger than a structural feature of the microfluidic device. In some cases, the non-fluidic transfer mechanism may comprise a channel comprising at least one corner, at least one edge, or a combination thereof. In some cases, the at least one corner may comprise a corner angle of about 90 degrees. In some cases, the at least one edge may comprise an angle of less than about 90 degrees. In some cases, the non-fluidic transfer mechanism may comprise a channel comprising at least one corner or beam-like structure. In some cases, the width of the corner or beam-like structure may be less than about 20 um. In some cases, the width of the corner or beam-like structure may be less than about 15 um. In some cases, the width of the corner or beam-like structure may be less than about 10 um. In some cases, the width of the corner or beam-like structure may be less than about 8 um. In some cases, the width of the corner or beam-like structure may be less than about 6 um. In some cases, the width of the corner or beam-like structure may be less than about 5 um. In some cases, the width of the corner or beam-like structure may be less than about 4 um. In some cases, a channel may comprise 1, 2, 3, 4, 5, 6, 7, 8, 9, 10 or more corners or beam-like structures. One or more corners or beam-like structures may be positioned adjacent to one another along a channel or may be spaced apart, such as spaced apart by about: 1 um, 2 um, 3 um, 4 um, 5 um, 6 um, 7 um, 8 um, 9 um, 10 um or more. Spacing between corners or beam-like structures may be constant such as 2 um spacing. Spacing may vary, such as 2 um spacing between a first corner and a second corner, and 4 um spacing between the second corner and a third corner.

Another aspect of the present disclosure provides a microfluidic device. In some cases, the microfluidic device comprises: a path configured to receive a plurality of objects; a trap adjacent thereto to the path and configured for occupancy of an object of the plurality of objects; a partition adjacent thereto the trap; and a channel positioned between the trap and the partition, wherein the channel comprises at least one corner, at least one edge, at least one beam-like structure or a combination thereof. In some cases, the at least one corner may comprise a corner angle of about 90 degrees. In some cases, the at least one edge may comprise an angle of less than about 90 degrees. In some cases the width of the beam structure may be less than about 20 um. In some cases, the width of the corner or beam-like structure may be less than about 15 um. In some cases, the width of the corner or beam-like structure may be less than about 10 um. In some cases, the width of the corner or beam-like structure may be less than about 8 um. In some cases, the width of the corner or beam-like structure may be less than about 6 um. In some cases, the width of the corner or beam-like structure may be less than about 5 um. In some cases, the width of the corner or beam-like structure may be less than about 4 um.

Another aspect of the present disclosure provides a method of screening a compound. In some cases, the method comprises: providing an array of partitions comprising a plurality of partitions, introducing the compound into at least a portion of the partitions of the plurality of partitions; and quantifying a biological response within the plurality of partitions. In some cases, a cell may be disposed within each partition of the plurality of partitions. In some cases, the biological response may be an amount of viral replication, a presence of cell death, an amount of intracellular viral RNA, or a combination thereof. In some cases, the cell may be a latently infected virus cell. In some cases, the cell may be infected with human immunodeficiency virus (HIV). In some cases, the cell may be resistant to an antiretroviral therapy (ART). In some cases, the compound may be an anti-latency drug. In some cases, the array of partitions may be the plurality of partitions.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "figure" and "FIG." herein), of which:

FIG. 8a-b shows a magnified view of one array site (a) and a 4×4 array having control wires (T1-T4) and control valves (V1-V4) (b).

FIG. 25 shows a fluid flow in a microfluidic channel allowing fluid to flow through three paths when a fluid flow is turned on.

FIG. 26 shows a hydrodynamic resistance in a microfluidic channel when a fluid flow is turned off and when an acoustic field is turned on.

FIG. 27a-b shows a fluid flow that splits into a parallel network of three flow streams.

FIG. 30a-b shows (a) a proliferation rate of a heterogeneous population of cancer cells exposed to drug therapy and (b) a proliferation rate of the cancer cells six months later.

DETAILED DESCRIPTION

Figure 1:
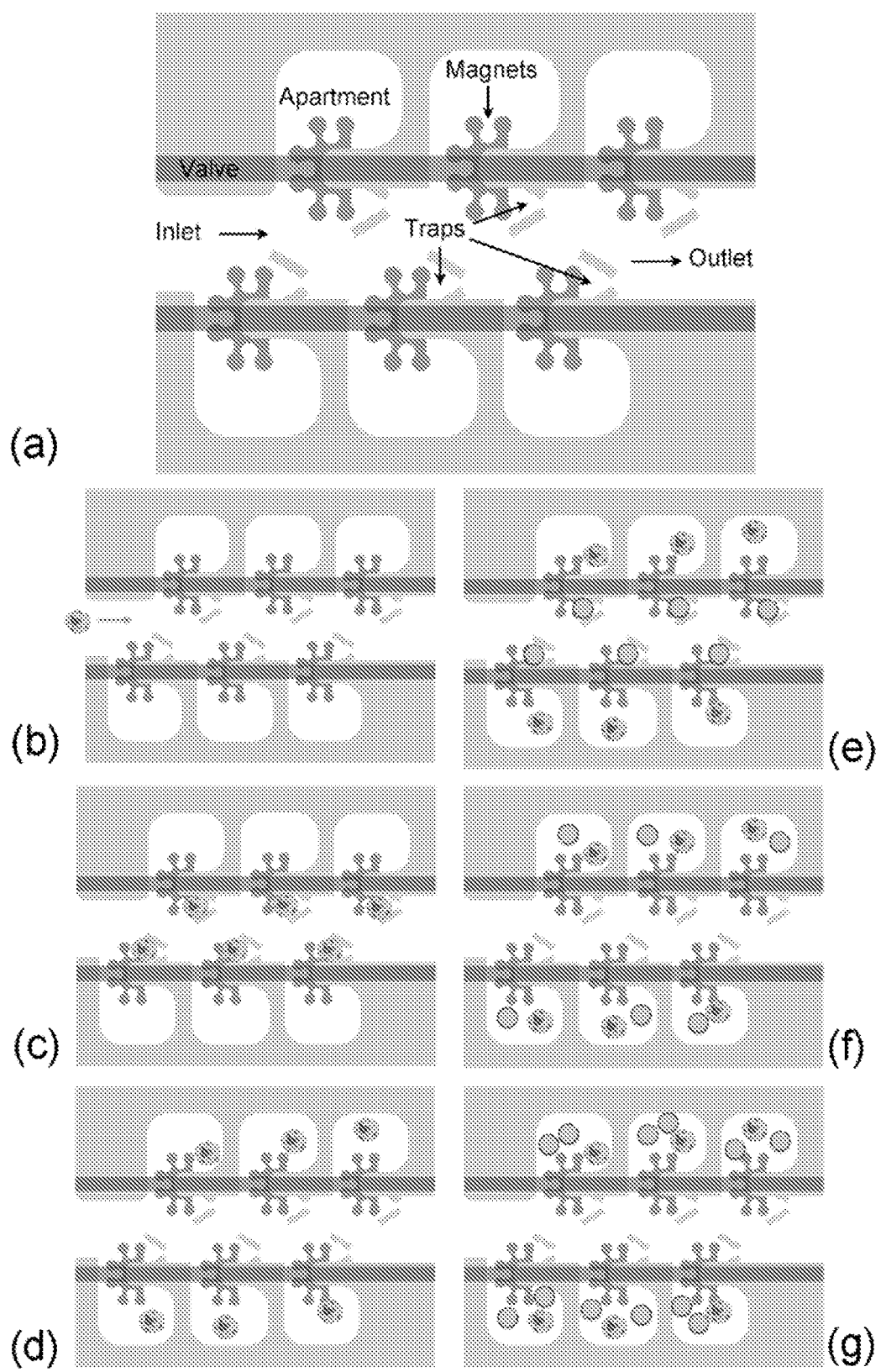
FIG. 1a-g shows an illustration of a two-step transfer process to first trap objects in a trap disposed in a flow path, and then transfer the trapped object into a partition using a magnetic mechanism.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

As used herein, the singular forms "a", "an", and "the" include plural references unless the context clearly dictates otherwise. Any reference to "or" herein is intended to encompass "and/or" unless otherwise stated.

As used herein, the term "about" means the referenced numeric indication plus or minus 15% of that referenced numeric indication.

As used herein, the term "object," generally refers to a cell or fragment thereof, a bead, a droplet such as a liquid droplet, an embryo or fragment thereof, an organism, or any combination thereof. An object may be a bead, wherein the bead comprises antibodies, cytokine-specific antibodies, chemokine-specific antibodies, growth factor-specific antibodies enzymes, enzyme substrates, proteins, small molecules, glycoproteins, drug molecules, polysaccharides, fluorophores, oligonucleotides, oligonucleotide barcodes, or any combination thereof.

As used herein, the term "trap," generally refers to a location of restricted movement of an object. A trap may be a physical trap, such as a physical barrier. A trap may be a non-physical trap, such as a laser trap. A trap may be a hydrodynamic trap. A trap may trap a single object at one time. A trap may trap multiple objects at one time. A trap may trap multiple objects in sequence, by removing a first trapped object to permit a second object to be trapped. A partition may comprise a trap, such as a hydrodynamic trap. A trap may be a hydrodynamic trap, a bubble trap, an optical trap, a trident trap, a physical barrier trap, a magnetic trap, a laser trap, or any combination thereof. A microfluidic device may comprise more than one type of trap. A microfluidic device may comprise 2 different types of traps. A microfluidic device may comprise a single type of trap. A partition may comprise a first type of trap and adjacent thereto a partition and fluidically connected to a path may be a second type of trap. A trap may be adjacent thereto at least one path and at least one partition.

As used herein, the term "partition," generally refers to a physical space that is separate from other partitions adjacent thereof. A partition may be an apartment. A partition may be a microfluidic chamber or well. A partition may be fluidically or operatively connected to a track, a trap, a path, a valve, a sensor, or any combination thereof. A partition may comprise an object, such as a cell or a bead. A partition may comprise more than one object, such as both a bead and a cell. A partition may comprise a volume to accommodate multiple cell doublings.

As used herein, the term "path," generally refers to a path along which an object and/or a fluid may travel. A path may be a channel, such as a microfluidic channel. A path may accommodate a flow of fluid, such as a buffer or cell media. A path may accommodate multiple objects, such as cells and/or beads. A path may be fluidically or operatively connects to one or more tracks, one or more traps, one or more partitions, one or more valves, one or more sensors, or any combination thereof.

As used herein, the term "cell," generally refers to a prokaryotic cell or a eukaryotic cell. The cell may be an adherent or a non-adherent cell, such as an adherent prokaryotic cell, adherent eukaryotic cell, non-adherent prokaryotic cell, or non-adherent eukaryotic cell. A cell may be a yeast cell, a bacterial cell, an algae cell, a fungal cell, or any combination thereof. A cell may be a mammalian cell. A cell may be a primary cell obtained from a subject. A cell may be a cell line or an immortalized cell. A cell may be obtained from a mammal, such as a human or a rodent. A cell may be a cancer or tumor cell. A cell may be an epithelial cell. A cell may be a red blood cell or a white blood cell. A cell may be an immune cell such as a T cell, a B cell, a natural killer (NK) cell, a macrophage, a dendritic cell, or others. A cell may be a neuronal cell, a glial cell, an astrocyte, a neuronal support cell, a Schwann cell, or others. A cell may be an endothelial cell. A cell may be a fibroblast or a keratinocyte. A cell may be a pericyte, hepatocyte, a stem cell, a progenitor cell, or others. A cell may be a circulating cancer or tumor cell or a metastatic cell. A cell may be a marker specific cell such as a CD8+ T cell, a CD4+ T cell, a $CD44^{high}/CD24^{low}$ cell, an Lgr5/6+ stem cell, or others. A cell may be a neuron. A neuron may be a central neuron, a peripheral neuron, a sensory neuron, an interneuron, a intraneuron, a motor neuron, a multipolar neuron, a bipolar neuron, or a pseudo-unipolar neuron. A cell may be a neuron supporting cell, such as a Schwann cell. A cell may be one of the cells of a blood-brain barrier system. A cell may be a cell line, such as a neuronal cell line. A cell may be a primary cell, such as cells obtained from a brain of a subject. A cell may be a population of cells that may be isolated from a subject, such as a tissue biopsy, a cytology specimen, a blood sample, a fine needle aspirate (FNA) sample, or any combination thereof. A cell may be obtained from a bodily fluid such as urine, milk, sweat, lymph, blood, sputum, amniotic fluid, aqueous humour, vitreous humour, bile, cerebrospinal fluid, chyle, chyme, exudates, endolymph, perilymph, gastric acid, mucus, pericardial fluid, peritoneal fluid, pleural fluid, pus, rheum, saliva, sebum, serous fluid, smegma, sputum, tears, vomit, or other bodily fluid. A cell may comprise cancerous cells, non-cancerous cells, tumor cells, non-tumor cells, healthy cells, or any combination thereof.

As used herein, the term "bead," generally refers to a particle. A bead may be a nano-sized particle. A bead may be a micro-sized particle. A bead may be smaller than a cell. A bead may be a magnetic bead. A bead may comprise a magnetic material, a polymeric material, or a combination thereof. A bead may be configured to bind to a second bead or to a cell or cellular fragment thereof. A bead may have a surface coating adjacent to at least a portion of the bead surface. A bead may be conjugated to one or more antibodies or fragments thereof, enzymes, receptors, proteins or fragments thereof, polysaccharides, lipids, peptides, small molecules, nucleic acids or fragments thereof, oligonucleotides or fragments thereof, DNA molecules, RNA molecules, or any combination thereof.

As used herein, the term "high priority object," generally refers to an object such as a cell, that is of higher priority than other objects in a plurality of objects. For example, the high priority cell may be a drug-resistant cell. A high priority cell may exhibit a cellular phenotype that warrants collection of the cell for further analysis. A high priority cell may be a cell of a plurality of cells that is responsive, is most responsive, or is least responsive to a compound such as a drug or salt thereof.

As used herein, the term "transfer mechanism," generally refers to a feature to transfer an object from a first location to a second location, such as from a trap into a partition adjacent thereto. A transfer mechanism may be a physical structure. A transfer mechanism may be a non-physical structure. A transfer mechanism may fluidically transfer an object. A transfer mechanism may non-fluidically transfer an object. A transfer mechanism may comprise a track or specific path along which an object transfers from a first location to a second location, such as from a trap into a partition adjacent thereto. The track may be a physical structure or a non-physical structure. A transfer mechanism may comprise magnetic material. A transfer mechanism may comprise a magnetic field, an electric field, a gravitational force, a centrifugal force, a laser force, a fluidic force, or any combination thereof. A transfer mechanism may comprise a magnetic mechanism, acoustic mechanism, electric mechanism, optical mechanism, optoelectronic mechanism, gravitational mechanism, centrifugal mechanism, acceleration mechanism, or any combination thereof.

As used herein, the term "phenotyping," generally refers to characteristics or traits of an object, such as a cell or bead. A metric to determine a bead phenotype may include determining whether the bead is a magnetizable bead or a non-magnetizable bead. A metric to determine a cellular phenotype may include measuring a cell proliferation, a cell morphology, a cell motility, a cell adherence to a surface or to another cell, an expression level of a protein or a nucleic acid or a surface marker or a fragment thereof, a subcellular localization of a protein or a nucleic acid or a fragment thereof, a viral shedding, a viral secretion, a protein secretion, a transcriptional profile, a number and type of cell-cell junction, or any combination thereof.

As used herein, the term "identifier," generally refers to an identifier that identifies an object, such as a cell or a bead, or a partition. An identifier may be a known identifier. The identity of an identifier may be deciphered or determined. An identifier may be a unique identifier. An identity of an identifier may be determined prior to addition to a device or system or to an object. An identify of an identifier may be determined after addition to the device or system or to an object. Each partition of a plurality of partitions may comprise a unique identifier. Each object of a plurality of objects may comprise a unique identifier. An identifier may comprise a barcode, such as a DNA barcode. An identifier may be conjugated or adjacent thereto an object, such as a bead or a cell. An identifier may be conjugated or adjacent thereto two objects, such as a bead and a cell. An identifier may be associated with a partition, such as located within a partition or adhered to a partition. An identifier may uniquely identify a partition of a plurality of partitions. An identifier may be printed into a partition during a device fabrication. An identifier may be introduced into a partition after device fabrication. An identifier may uniquely identity each partition of a plurality of partitions. An identifier may be known prior to associating such identifier with a partition. In such cases, the identifier may not need to be deciphered. An identifier may be associated with an object prior to introducing the object into the device or system. An identifier may be associated with an object once the object and the identifier are both positioned within a partition. An identifier may be known prior to associating such identifier with an object, a partition, or a combination thereof. In such cases, the identifier may not need to be deciphered.

As used herein, the term "condition," generally refers to a condition of the devices, systems, or methods provided herein. For example, a condition may be a temperature of a device or system or a temperature of a portion of the device. A condition may be a gas composition within the device or system, such as within one or more partitions. A condition may be a nutrient level the device or system, such as within one or more partitions. A condition may be a flow rate of a fluid flowing in a path of the device. A condition may be a cell number or a bead number within one or more partitions. A condition may be a compound concentration within one or more partitions. A condition may be a contamination level or endotoxin level within the device or system.

As used herein, the term "non-fluidic transfer," generally refers to a transfer that uses forces other than fluid flow to perform the transfer. For example, a non-fluidic transfer may be employing a magnetic field to move an object along a magnetic track, or an acoustic wave to push an object along a preferred direction, or an acoustic streaming that creates a fluidic vortex near structural elements, the fluidic vortex of which may push an object along a preferred direction.

As used herein, the term "sensor," generally refers to a sensor that senses or measured a specific metric. A sensor may be a temperature sensor, a pH sensor, a gas sensor such as an $O_2$ sensor or $CO_2$ sensor, a glucose sensor, a level sensor, or any combination thereof. A sensor may be an optical sensor such as a bioluminescent sensor that senses a fluorescent or luminescent signal. A sensor may be an electrochemical sensor such as an amperometric sensor, a conductometric sensor, a potentiometric sensor, or a sensor that senses superficial charge. A sensor may be an optoelectric sensor such as a resonant mirror, a fiber optic, or a surface plasmon resonance sensor. A sensor may be a piezoelectric sensor such as a crystal resonance frequency sensor, a surface acoustic wave sensor, an acoustic streaming sensor, or a surface transverse wave sensor. A sensor may be a biosensor such as an enzyme electrode, an immunosensor, a DNA sensor, a RNA sensor, a microbial sensor, or any combination thereof. A sensor may comprise one or more identifiers (such as unique identifiers). A sensor comprising an identifier may be associated with a partition, thereby identifying the partition from a plurality of partitions. A sensor comprising an identifier may be associated with a partition, such as adhered to a portion of the partition or located within a partition. A sensor comprising an identifier may be printed into a partition during a device fabrication. A sensor comprising an identifier may be introduced into a partition after device fabrication. A sensor comprising an identifier may uniquely identity each partition of a plurality of partitions. A sensor comprising an identifier may be known prior to associating such identifier with a partition. In such cases, the identifier may not need to be deciphered at a later time point. A device or system may have one or more sensors such as one or more electrochemical sensors, one or more optical sensors, one or more thermal sensors, one more resonant sensors, one or more ion-sensitive sensors, one or more biosensors (such as a DNA sensor or RNA sensor), or any combination thereof. A device or system may have 1, 2, 3, 4, 5, 6, 7, 8, 9, 10, 11, 12, 13, 14, 15, 20, 30, 40, 50, 100, 200, 500 sensors or more. A device or system may have at least 1 sensor for each partition. A device or system may have at least 2 sensors for each partition. A device or system may have at least 3 sensors for each partition. A device or system may have at least 2, 3, 4, 5, 6, 7, 8 sensors or more for each partition. A temperature sensor associated with a partition may sense a temperature or an optical sensor associated with a partition may sense a bioluminescence. A sensor may sense a metric specific to a single partition. A sensor may sense one or more metrics of an array of partitions. A sensor may sense a metric of the device or system. A metric that a sensor may sense may include a temperature, an 02 concentration, a CO2 concentration, a pH level, a protein concentration, a bioluminescence concentration, a fluorescence concentration, a mass or weight, a number of distinct RNA or DNA molecules in a cell lysis, or any combination thereof. A control system operatively coupled to a sensor may direct a routine sensing of a metric. For example, a control system may direct a thermistor to sense a temperature of a partition every 60 minutes. Alternatively, a control system operatively coupled to a sensor may direct a specific sensing of a metric when a parameter is met. For example, a control system may direct a gas sensor to sense a CO2 concentration of a partition when a pH sensor senses a pH level of the partition rises above 7.4. A user may input a routine sensing schedule into the control system. A user may input a specific sensing schedule into the control system.

As used herein, the term "compound," generally refers to a compound that may produce an altered cellular response. A compound may be a drug or a pharmaceutical composition or salt thereof. A compound may be a protein, a peptide, a nucleic acid, an antibody, an aptamer, a small molecule, a fragment thereof, or any combination thereof. A compound may be a cell or a fragment thereof. A compound may be a tissue or tissue fragment. A compound may be a naturally-derived compound or a synthetic compound.

As used herein, the term "ion," generally refers to a molecule with a net electric charge. Examples of ions may include cations and anions including calcium, potassium, sodium, lithium, magnesium, aluminum, zinc, iron, copper, silver, barium, chromium, hydrogen, hydronium, lead, manganese, mercury, nitronium, potassium, strontium, tin, hydride, fluoride, chloride, bromide, iodide, sulfate, hydrogen sulfate, thiosulfate, perchlorate, chlorate, chlorite, hypochlorite, carbonate, hydrogen carbonate, bicarbonate, acetate, cyanide, cyanate, thiocyanate, hydroxide, or any combination thereof.

As used herein, the term "gas," generally refers to a type of fluid. Examples of gases may include nitrogen, oxygen, argon, carbon dioxide, neon, helium, methane, krypton, hydrogen, xenon, or any combination thereof.

As used herein, the term "nutrient," generally refers to macronutrients and micronutrients that are needed for an organism to survive and/or grow. Examples of macronutrients include carbohydrates and fragments thereof, proteins and fragments thereof, fats and fragments thereof, or any combination thereof. Examples of micronutrients include (i) minerals such as salts, copper, or iron, (ii) vitamins such as vitamin A, vitamin B1, vitamin B2, vitamin B3, vitamin B5, vitamin B6, vitamin B7, vitamin B9, vitamin B12, vitamin C, vitamin D, vitamin E, vitamin K, (iii) water, or any combination thereof. Nutrients may include (i) essential nutrients such as fatty acids, amino acids, vitamins, minerals, and (ii) non-essential nutrients such as dietary fiber.

The term "subject," as used herein, generally refers to any animal or living organism. Animals can be mammals, such as humans, non-human primates, rodents such as mice and rats, dogs, cats, pigs, sheep, rabbits, and others. Animals can be fish, reptiles, or others. Animals can be neonatal, infant, adolescent, or adult animals. Humans can be more than about 1, 2, 5, 10, 20, 30, 40, 50, 60, 65, 70, 75, or about 80 years of age. The subject may have or be suspected of having a disease, such as a cancer or a tumor. The subject may be a patient being treated for a disease, such as a cancer patient, a tumor patient, or a cancer and tumor patient. The subject may be predisposed to a risk of developing a disease such as a cancer or a tumor. The subject may be in remission from a disease, such as a cancer or a tumor. The subject may not have a cancer, may not have a tumor, or may not have a cancer nor a tumor. The subject may be healthy.

As used herein, the term "disease or condition," generally refers to an abnormal condition or disorder that affects a subject. The condition may be a medical condition. The disease or condition may have symptoms or may be symptom-less. The disease or condition may be a cancer, such as adrenal cortical cancer, anal cancer, aplastic anemia, bile duct cancer, bladder cancer, bone cancer, bone metastasis, central nervous system (CNS) cancers, peripheral nervous system (PNS) cancers, breast cancer, Castleman's disease, cervical cancer, childhood Non-Hodgkin's lymphoma, lymphoma, colon and rectum cancer, endometrial cancer, esophagus cancer, Ewing's family of tumors (e.g. Ewing's sarcoma), eye cancer, gallbladder cancer, gastrointestinal carcinoid tumors, gastrointestinal stromal tumors, gestational trophoblastic disease, hairy cell leukemia, Hodgkin's disease, Kaposi's sarcoma, kidney cancer, laryngeal and hypopharyngeal cancer, acute lymphocytic leukemia, acute myeloid leukemia, children's leukemia, chronic lymphocytic leukemia, chronic myeloid leukemia, liver cancer, lung cancer, lung carcinoid tumors, Non-Hodgkin's lymphoma, male breast cancer, malignant mesothelioma, multiple myeloma, myelodysplastic syndrome, myeloproliferative disorders, nasal cavity and paranasal cancer, nasopharyngeal cancer, neuroblastoma, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma (adult soft tissue cancer), melanoma skin cancer, non-melanoma skin cancer, stomach cancer, testicular cancer, thymus cancer, uterine cancer (e.g. uterine sarcoma), vaginal cancer, vulvar cancer Waldenstrom's macroglobulinemia, or any combination thereof. The disease or condition may be a viral infection, such as HIV, viral hepatitis, herpes simplex type 1, encephalitis, meningitis, rabies, coxsackie B virus, varicella zoster virus, human herpesvirus 6, smallpox, molluscum contagiosum, human papillomavirus (HPV), rubella, measles, coxsackie A virus, influenza virus, respiratory syncytial virus, SARS coronavirus, poliovirus, HTLV-1, adenovirus, rotavirus, or any combination thereof. The disease or condition may be a neuronal condition such as Parkinson's disease, Alzheimer's disease, motor neuron disease, multiple sclerosis, myopathy, neuromuscular transmission disorder, neuropathy, myelopathy, dementia, amyotrophic lateral sclerosis (ALS), cerebral palsy, essential tremor, Huntington's disease, muscular dystrophy, neuromyotonia, or any combination thereof.

Rare cell subsets may hold the key to understanding the pathogenesis and outcomes of human disease; yet, surprisingly few technologies are equipped to perform the wide assortment of phenotypic and genotypic measurements necessary to quantify disease states in rare cells. A direct mapping between the phenotypic properties of a single cell, such as its proliferation rate, drug response, and viral or protein secretions, and the transcriptional properties of that same cell, may advance understanding of basic disease biology and lead to new methods for credentialing drugs or immunotherapies. Even within a single tumor, there exists a remarkable genetic and phenotypic heterogeneity, which is believed to drive the resistance to chemotherapy. As described by the devices, systems, and methods provided herein, the ability to excise a patient's tumor, dissociate the cells, organize them in arrays, and study their drug sensitivities with single cell resolution may permit identification of rare drug resistant cells and use next generation sequencing (NGS) to quantify their pathways of drug resistance. These approaches may advance research and drug discovery in fields like immunology, infectious diseases, and neuroscience. For example, the quest for an HIV cure may benefit tremendously from the ability to measure the functional responses of infected T-cells (e.g., identify cells shedding viral particles), and the transcriptome of the infected cells, which together may provide important insights into the mechanisms by which anti-latency compounds disrupt HIV reservoirs. Commercial platforms, such as Fluidigm® and DEPArray® can measure the function and gene expression of single cells, but their unfavorable scaling principles hinder parallelization beyond ~1,000 cells. On the other hand, stochastic assembly of single cells with DNA barcodes in droplets and in microarrays can access larger scales but are unable to simultaneously measure cell function and gene expression in each single cell. Thus, there remains an urgent need for scalable, comprehensive single cell analysis platforms.

The devices, systems, and methods provided herein may trap objects in partitions of a microfluidic device, such as a microfluidic chip, and may selectively release objects from the partitions in an addressable manner. The devices, systems, and methods provided herein may employ a combination of external fields to organize objects in a highly efficient, rapid, parallel manner. The external fields may consist of magnetic fields, electric fields, acoustic fields, hydrodynamic flow, or any combinations thereof, which may operate jointly to transport objects, ranging from spherical colloidal particles to cells, into specific partitions of a microfluidic device.

The devices, systems, and methods provided herein may be in the general field of cellular analysis, and particularly may be in the field of new cellular analysis platforms and may allow large numbers of cells to be individually isolated into partitions, comprehensively phenotyped, and their gene expression analyzed in a massively parallel format. There is a need in the field of cellular analysis to design systems that are flexible, scalable platforms, which can sort individual cells into arrays, monitor their morphology, proliferation, viability, and the molecules they secrete, and retrieve their DNA and RNA transcripts for gene expression analysis. Single cell arrays platforms as described herein are an important tool for analyzing the mechanisms driving heterogeneous cellular responses to myriad of environmental stimuli, such as the presence of drug compounds, or interactions with other cells. To date there is a need for platforms having the required flexibility, programmability, scalability, and controllability to organize a large array of single objects (far in excess of 10,000 single objects), comprehensively phenotype the behavior and function of those objects (such as cells), and then retrieve their content for analysis (such as genetic content for transcriptome and other gene expression analysis). There remains an urgent need to develop systems, which can automate the placement of objects in partitions, enable long-term evaluation (such as microscopic evaluation) in response to different environmental cues (such as exposure to drugs or other single objects), and retrieve selective objects at specified times for follow-on analysis (such as transcriptomic analysis or clonal expansion).

A fundamental limitation of existing trapping approaches is an inability to release the trapped object and transfer it to an adjacent partition, thereby freeing up the trap to capture a second, third, and fourth object and so on. The devices, systems, and methods provided herein overcome this problem by providing an ability to use magnetic force, electric force, acoustic force, optical force, a fluid force, or other force, or any combination thereof to transfer the object from the trap into an adjacent partition, such as a microchamber or microwell. By serially repeating this processes N times, it is possible to place N types of objects in a given partition.

Existing microfabrication systems designed to load objects into micro-wells via sedimentation of a suspension of objects may be designed with lateral dimensions slightly larger than the diameter of a single object, such that there is a low probability to capture more than one cell per microwell. Due to the random nature of this sedimentation process, the single object trapping efficiency in these systems may be very low (such as about 5-10%). In contrast, the devices, systems, and methods described herein may provide a novel approach for organizing objects into partitions, such as microfabricated chambers, with high efficiency and/or speed. More than one type of object may be organized in each partition (such as a microchamber), such as a pair of single cells, and/or a cell co-organized with one or more different types of particles (such as colloidal particles). The objects, such as cells, added to the arrayed partitions may be maintained for extended durations inside the partition, where they may proliferate, migrate, interact with other cells, and be characterized with fluorescent stains or other methods for analyzing cellular phenotypes. The microchambers may be individually addressed, when it may be desirable to import or to export objects such as cells or particles from specific microchambers. Many objects may be retrieved from the microchambers in parallel, such as in applications where colloidal particle supports may be used to capture the genetic/genomic material of cells or their RNA transcripts of single cells, or when specific "high-value" cells may need to be retrieved for clonal expansion.

In some embodiments of the devices, systems, and methods provided herein, a combination of particle manipulation approaches may be used to increase the speed and efficiency for organizing a large array of objects, such as single cells, into partitions. For example, a set of traps (such as hydrodynamic traps) that may be placed adjacent thereto partitions and may be used to passively capture objections such as single colloidal particles or cells with high efficiency. After the traps are populated with the single objects, such as cells or single colloidal particles, they may be moved into the partitions by imposing a time-varying magnetic field or by activating an acoustic field, a high frequency electric field in patterned electrodes or by other methods.

The devices, systems and methods provided herein provide a platform for manipulating cells similarly to the way that electronic information is manipulated in a computer memory. Integrated circuits may transport magnetically labeled cells down desired paths (conductors), switch their directions at junctions (transistors), store them in local partitions or apartments (capacitors), and organize them in arrays (multiplexers). In essence, this platform can "write" single cells (or small cell populations) to individual partitions, and "read" the functional responses of objects, such as live single cells, in situ. These high-throughput platforms can sort >$10^6$ single objects, such as cells, into an array, conduct multiplexed phenotypic analysis of the arrayed cells, and then assign known DNA barcodes to the RNA transcripts of each phenotyped cell to enable downstream tracking during pooled sequencing. The platform can be automated and can phenotype and barcode single cells, as well as decipher the barcodes prior to or after pooling them for further analysis, such as Next Generation Sequencing (NGS). For example, the devices, systems, and methods provided herein may organize single DNA-barcoded magnetic beads in large arrays; decipher the identity of each DNA barcode in situ with sequencing by synthesis (SBS); co-assemble single cells in each array site to form bead/cell pairs; analyze the function and phenotype of the arrayed cells; reverse transcribe single cell RNA onto DNA barcodes; and pool the barcoded transcripts for massively parallel CEL-seq analysis. The ability to map individual cell phenotypes with known DNA barcodes will allow the RNA from "high priority" phenotypes to be isolated and studied in a targeted manner.

The devices, systems, and methods provided herein provide for a single cell platform that can be automated, can measure the function and gene expression of single cells in high-throughput and can down-select which single cells undergo Next Generation Sequencing (NGS) by enriching the transcripts of these "high priority" phenotypes. These fundamental advantages enable significant cost reductions and targeted genomic analysis of rare cell subsets responsible for the pathogenesis of human diseases. Applicable to diverse fields of inquiry, this platform can provide a multitude of information about single cells, such as: (a) image-based phenotyping of arrayed cells (i.e., for properties such as morphology, motility, and expression/staining/subcellular localization of proteins of interest); (b) assemble controlled numbers of objects in each array site (i.e., single cell pairs, cell/bead pairs, etc.); (c) analyze single cell proliferation in the presence of drug treatments or other single cells; (d) attach known DNA barcodes to the RNA transcripts of each arrayed cell; (e) retrieve the barcoded RNA of all cells to allow selective PCR amplification of high priority phenotypes, and combinations thereof.

The devices, systems and methods provided herein can enable the end user to conduct targeted transcriptomic analysis of "high priority" cell phenotypes by selectively enriching specific barcodes. This ability to perform targeted enrichment of specific cellular RNA can allow the pooled transcripts to be analyzed immediately, or kept for later analysis.

The devices, systems, and methods provided herein may (a) probe heterogeneous cell-cell architectures that involve two or more single cell types within a confined spatial region, which can be used to assess future cancer immunotherapies and monitor individual cell-cell cytolytic interactions; (b) integrate local chemosensors for detecting secreted molecules, such as cytokines, chemokines, and growth factors; (c) extract specific cells of interest for additional interrogation, immortalization, or clonal expansion, and/or (d) develop electroporation and/or CRISPR/Cas9 techniques to edit the genome of cells in situ.

A method to organize an object, such as a cell or bead, into a partition may include capturing the object in a trap that is adjacent thereto the partition and then transferring the object into the partition. The partition may be a well, such as a microwell, or an apartment. The trap may trap a single object at a time. Once an object is release from a trap or transferred into a partition, the trap may be available to trap an additional object. When a trap has already trapped an object, a second object may pass by the filled trap and travel along a path to a next available trap. In this way, multiple objects may singularly fill multiple traps along a path. The partition may accommodate more than one object, such that a plurality of objects may be sequentially trapped and transferred into the same partition. Traps may be populated by flowing objects along a path that may be adjacent thereto one trap or multiple traps in series. A continuous flow comprising a flow rate may be input into the device to populate the traps with objects. A single flow or an intermittent flow may be input into the device to populate the traps with objects. Before activating a transfer mechanism to transfer the object into an adjacent partition, a flow in an adjacent path may be stopped, such as when a trap is filled with an object or such as when a portion of traps are filled with objects.

Between a trap and a partition may be a channel, such as an entrance or exist channel through which an object enters or exits an individual partition. A channel may operatively or fluidically connect a trap to a partition adjacent thereto. An object may travel along the channel to enter or to exit a partition. In some cases, there is not a channel between the trap and the partition adjacent thereto.

An object may be a cell or a bead. In some cases, a cell may be trapped and transferred into a partition, followed by a bead that may be trapped and transferred into the same partition. In some cases, a bead may be trapped and transferred into a partition, followed by a cell that may be trapped and transferred into the same partition. In some cases, a first cell may be trapped and transferred into a partition, followed by a second cell that may be trapped and transferred into the same partition. In some cases, the transfer employed to transfer the first object may be the same as the transfer employed to transfer the second object. In some cases, the transfer employed to transfer the first object may be different than the transfer employed to transfer the second object. For example, the transfer of a bead into a partition may employ a magnetic track and a transfer of a cell into a partition may also employ a magnetic track. In another example, the transfer of the bead into a partition may employ a magnetic track and a transfer of a cell into a partition may employ an acoustic mechanism.

A bead may be a magnetic bead. A magnetic bead may interact with a magnetic component of a microfluidic device, such as a magnetic track positioned between a trap and an adjacent partition. A bead may further be conjugated with an antibody or fragment thereof, a receptor, a protein or fragment thereof, a polysaccharide, a lipid, a peptide, a small molecule (such as an organic small molecule), a nucleic acid or fragment thereof, an oligonucleotide or fragment thereof such that a cell may bind to the magnetic bead. A cell may bind to the bead in a partition. A cell-bead pair may be moved within the partition or transferred between the partition and the trap and the path, in some cases using a magnetic track when the bead is a magnetic bead. A bead may be a nanobead. A bead may be a microbead. A bead may be spherical. A bead may be non-spherical. A bead may be porous or solid. A bead may comprise a specific surface chemistry. A bead may be associated with a cell. A plurality of beads may be associated with a cell. An association between a bead and a cell may be a bond, a conjugation, a physical proximity, a cell engulfing a bead, or others, or combinations thereof. A bead may comprise a barcode, such as a DNA barcode and a barcode thereon the bead may be mapped to a cell phenotype of the cell to which the bead is associated.

In some cases, the one or more objects that are transferred to partitions, may also be removed from the partitions. The objects may be removed from the partition using a magnetic track, or by reversing the fluid flow through the device. The objects may be selectively removed, such as a subset of objects in partitions may be removed. The objects may be collectively removed, such as all the objects in partitions are removed. Selective removal may remove cells of interest, cells that possess a particular phenotype, cells that require further analysis, or combinations thereof. Selective removal may occur by selectively addressing the partition containing the cell of interest. Selective removal may result from destroying the unselected objects, and that collectively removing those selected objects that remain undestroyed. When the object is a cell, destruction may involve cell lysis, laser or optical destruction, or other methods of inducing cell death. A subset of a plurality of objects may be selectively removed from a plurality of partitions, wherein the remaining objects remain in their respective partitions. An object may be selectively removed from a partition, wherein other objects in other partitions remain. For example, a cell of interest such as a drug-resistant cell may be selectively removed from a partition for further analysis, wherein non-drug-resistant cells remain in their respective partitions. Selective removal from a partition may also occur for a cell-cell pair or a cell-bead pair, wherein the cells or the cell and bead are associated together, such as conjugated together. The selective removal may comprise a fluid flow or employing a magnetic mechanism, an electric mechanism, an acoustic mechanism, a centrifugal mechanism, a gravitational mechanism, or any combination thereof. A collective removal of a plurality of objects or plurality of object pairs may comprise a fluid flow or employing a magnetic mechanism, an electric mechanism, an acoustic mechanism, a centrifugal mechanism, a gravitational mechanism, or any combination thereof. Selective removal may also comprise destroying a portion of objects, such as objects in their respective partitions. In this case, the objects not of interest may be destroyed, whereas the objects of interest are not destroyed. The objects of interest may then be removed from the device. The destroying may comprise employing a laser stimulus, increasing or decreasing a local temperature, adding a local buffer, or any combination thereof.

A transfer mechanism may comprise one or more magnets. A transfer mechanism may comprise a microfluidic device having a magnetic material and applying a magnetic field to the microfluidic device. The magnetic material may be formed in a specific shape such as a track. The track may be positioned between or connect a trap and a partition.

A transfer mechanism may comprise a microfluidic device with structural resonance features. The structural resonance features may be formed in one or more partitions or in a connecting channel between a trap and a partition. The structural resonance features may include a partition shaped in tiered widths or in a cone shape. The widest part of the cone or the widest tiered width may be closest to the adjacent trap and the narrowest part of the cone or the narrowest tiered width may be farthest from the adjacent trap. Changing an acoustic stimulus applied to the microfluidic device may change the position of an object within the device based on the structural resonance features. Examples of this are shown in FIG. 6a-d, FIG. 7, FIG. 28a-c, FIG. 29a-c, and FIG. 31a-c. An acoustic energy may be generated by a piezoelectric transducer. The transducer may be attached to an exterior of the device. The transducer may be disposed to provide a bulk acoustic wave or acoustic streaming through the device. The transducer may comprise one or more materials such as quartz, lead zirconium titanate, barium titanate, zinc oxide, lithium niobate, lithium tantalite, lanthanum gallium silicate, or combinations thereof. The transducer may be excited by a set of interdigitated electrodes to produce a surface acoustic wave or acoustic streaming.

A transfer mechanism may comprise a laser trap. A laser trap may create a focal point, a focal point of which may be shifted or moved in space which may pull or drag an object out of the trap, such as a hydrodynamic trap, and into a partition. A collective transfer of multiple objects trapped in multiple traps employing a laser trap may be propagated by a holographic array.

A transfer mechanism may comprise a sedimentation force applied to the microfluidic device. After an object may be captured in a trap, a sedimentation force may be applied by tilting of the device in a single direction to sediment an object from a trap into an adjacent partition, such as using a gravitational force. A transfer mechanism may comprise a centrifugal force applied to the microfluidic device. After an object may be captured in a trap, a centrifugal force may be applied by spinning the device, such as in a centrifuge.

A transfer mechanism may comprise a combination of mechanisms. A transfer mechanism may comprise both a magnetic transfer mechanism and an acoustic transfer mechanism, such as applying a magnetic field to a device comprising a magnetic track and applying an acoustic wave or an acoustic streaming. A transfer mechanism may comprise a combination of a magnetic, acoustic, electric, optical, optoelectronic, gravitational, centrifugal, acceleration, or any combination thereof.

A method may comprise populating one or more traps of a plurality of traps and collectively transferring the trapped objected into partitions adjacent thereto the individual traps. A device may comprise one trap adjacent thereto a partition. A device may comprise two traps adjacent thereto a partition. A device may comprise a trap adjacent thereto two partitions. Multiple partitions may be populated with at least one object in a single collective transfer. For example, greater than 1,000 individual objects may be collectively transferred from their respective trap into a partition adjacent thereto. The objects may be cells or fragments thereof, beads, or a combination thereof. A device may populate a plurality of traps, collectively transfer a first set of trapped objects and subsequently populate a second plurality of traps and collectively transfer a second set of trapped objects into partitions. The trapping and transferred may be repeated. Objects contained within partitions may be collectively transferred out of their respective partitions using a transfer mechanism. Collective transfer of beads may occur along magnetic tracks positions between individual traps and partitions adjacent thereto. Collective transfer of cells may comprise an acoustic mechanism and/or magnetic mechanism. A single collective transfer may produce an object occupancy rate for the plurality of partitions at greater than about: 70%, 80%, 85%, 90%, 91%, 92%, 93%, 94%, 95%, 96%, 97%, 98%, or 99%. A single collective transfer may produce a single object occupancy rate for each of a plurality of partitions at greater than about: 70%, 80%, 85%, 90%, 91%, 92%, 93%, 94%, 95%, 96%, 97%, 98%, or 99%.

A trap may be a hydrodynamic trap. A trap may permit a single object to occupy the trap at one time. After an object leaves a trap such as back into a flow of a path or into an adjacent partition, the trap may be available to trap an additional object either from the partition or from the flow in the path. All traps of a device may be hydrodynamic traps. A portion of all traps of the device may be hydrodynamic traps. One or more partitions may comprise a trap, such as a hydrodynamic trap. At least a portion of the flow of the path may pass through the hydrodynamic trap. A plurality of traps may comprise a same type of trap, such as a hydrodynamic trap. A plurality of traps may comprise traps of different types, such as a hydrodynamic trap, a bubble trap, an optical trap, a trident trap, a physical barrier trap, a magnetic trap, an acoustic trap, a laser trap, or any combination thereof. Traps adjacent to a partition may comprise one type of trap such as a hydrodynamic trap and traps within a partition may comprise as same type of trap, such as a hydrodynamic trap or a different type of trap, such as an acoustic trap. In some cases, a volumetric flow through an unoccupied trap, such as a hydrodynamic trap, may be substantially higher than a volumetric flow through an occupied trap, such that no more than one object occupies a trap at one time. In some cases, no more than two objects that occupy a trap at one time.

Objects disposed within partitions of a device may be analyzed for a particular phenotype or a change in a phenotype. When objects are cells, a phenotype may include a cell proliferation, a cell morphology, a cell motility, an expression level of a protein or fragment thereof or a nucleic acid or fragment thereof, a subcellular localization of a protein or fragment thereof or a nucleic acid or fragment thereof, a viral shedding, a viral secretion, a protein secretion, a transcriptional profile, or any combination thereof. A phenotype of an individual cell may be analyzed. A phenotype of multiple cells may be analyzed, such as a pair of cells. A phenotype may be measured at one or more time points. A phenotype may be measured before introducing a compound to a partition, after introducing a compound to a partition, or a combination thereof.

The methods described herein may include contacting an object with another object, such as contacting a cell with a bead. The contacting may occur in a partition, in a path, in a channel operatively connecting a trap and a partition. Contacting may include contacting an object with an identifier, such as contacting a cell with an identifier or contacting a bead with an identifier. A bead may be pre-attached or pre-conjugated to an identifier prior to introduction into the device. An identifier may be a known identifier. An identifier may be a unique identifier. Each identifier introduced to a device may be unique from one another. An identifier added to a partition and subsequently contacted to an object, such as a cell or fragment thereof, may identify the cell or fragment thereof. After removing the cell or fragment thereof from the device, the identifier may continue to identify the cell or fragment thereof such that it may be sorted from a population of cells or fragments thereof or selectively analyzed. An identity of an identifier may be known prior to introduction into a device. An identity of an identifier may be deciphered after removal from a device. An identity of an identifier may be deciphered in the device, such as when an identifier is located within a partition. A contacting may be based on a determination of an object phenotype, such as adding a bead with an identifier to a subset of partitions having a particular phenotype. In such cases, a particular identifier may correspond to a particular object phenotype. An identifier may be a barcode sequence, such as a nucleic acid barcode sequence, such as a DNA barcode sequence. Identifying an object may comprise exposing an object to a set of sequencing reagents, performing a series of synthesis reactions, and determining an identify of the barcode sequence. The barcode sequence may comprise a fluorescent barcode.

In some cases, objects, such as cells, can be maintained or cultured in partitions of the device for one or more days, such as 2, 3, 4, 5, 6, 7, 14 days or more. A volume of a partition is sufficient to accommodate cell doubling during this culture time. A temperature, nutrient level, gas composition, or other may be maintained during this time to maintain cell viability.

In some cases, one or more conditions of a partition of a plurality of partitions or a subset of partitions of a plurality of partitions may be independently controlled. For example, a subset of partitions may be controlled at a temperature than is at least 2 degrees lower than the remaining partitions. A subset of partitions may be controlled at a media exchange rate than is higher than the remaining partitions. Addition of a compound may be added to a subset of partitions and not to the remaining partitions. A compound may be added two or more times to a subset of partitions and a single time to the remaining partitions. A subset of partitions may have a lysis buffer added and the remaining partitions do not have a lysis buffer added. A subset of partitions may have an additional object added, such as a cell or bead, and the remaining partitions do not have an additional object added.

Methods as provided herein may include fluidically capturing an object, such as capturing an object in a hydrodynamic trap and non-fluidically transferring the object into an adjacent partition, such as transferring the object along a magnetic track positions between the trap and the partition. The trap may be a hydrodynamic trap. After the transferring, the trap may be available to fluidically capture an additional object. The additional object may be a cell or a bead. The non-fluidically transferring may comprise a magnetic mechanism such as applying a magnetic field to the device comprising a magnetic material, such as a magnetic track positions between a trap and the partition, positioned within a partition, position along a channel connecting a trap and a partition, or any combination thereof. The non-fluidically transferring may comprise one more magnets and a magnetic track. The non-fluidically transferring may comprise a magnetic mechanism, an acoustic mechanism, an electric mechanism, an optical mechanism, an optoelectronic mechanism, applying a gravitational force, applying a centrifugal force, or any combination thereof. The non-fluidically transferring may comprise applying an acoustic stimulus to the device having structural resonance features disposed within the device, such as within a partition, within a trap, within a channel operatively connecting a trap and a partition, within a path, or any combination thereof. The non-fluidically transferring may comprise applying an acoustic stimulus to the device having a partition with a tiered or cone-shaped or tapered structure, such that a width of a partition is sequentially reduced from an end closest to the trap and reducing towards an end farthest from the trap. An object may be non-fluidically transferring into a partition when a volumetric flow through the partition is substantially smaller than a volumetric flow through an unoccupied trap. A volumetric flow through the partition may be substantially smaller than the volumetric flow through either the unoccupied trap or the bypass region, such that no objects may be transferred into the partition unless they are moved by non-fluidic transferring into a section of the partition wherein the volumetric flow inside the partition may move the object deeper into the interior of the partition.

A transferring may move an object from a trap into a partition. A transferring may move an object from a trap into a channel operatively connecting a trap and a partition. A transferring may move an object from a trap into a channel and into a partition. A transferring may move an object from a trap into a channel, into a partition, out of a partition, out of a channel, or any combination thereof. A transferring may include moving an object into a partition along one track, such as an inside track or an inside wall of a partition, and moving an object out of a partition along the same track, such as an inside track or an inside wall of the partition. A transferring may include moving an object into a partition along one track, such as an inside track or an inside wall of the partition, and moving the object out of the partition along a different track, such as an outside track or an outside wall of the partition. A transferring, such as an acoustic mechanism, a magnetic mechanism, a fluid flow or other may move an object to a different location within a trap. For example, a transferring may include moving an object deeper inside a partition. A transferring may include moving an object to a lower region, a middle region, or an upper region of a partition. A transferring may include moving an object to a region of a partition or a channel that comprises a second object such as a cell or bead. A transferring may facilitate a contacting of an object with a second object. A transferring may include moving an object to a region of a partition or a channel that comprises a particular surface chemistry. A transferring may include moving an object to one side or another of a valve with the channel or partition.

A device may be a microfluidic device. A microfluidic device may comprise a path, such as a microfluidic channel. The path may be configured to receive a plurality of objects, a plurality of second objects and so on. A path may be configured to receive a fluid flow. A path may be configured adjacent to one or more traps, such as hydrodynamic traps or others. The trap may be configured for single object occupancy. The trap may be configured for double object occupancy or more. The trap may be configured to trap an additional object after a first object is removed from the trap. The trap may be adjacent thereto the partition. The trap may be adjacent thereto more than one partition. The path, the trap, and the partition may be operatively connected, such as fluidically connected such as to permit move of fluid, or one or more objects between them. A trap and a partition may be fluidically connected by a channel. The device may comprise a magnetic material formed in a shape, such as a magnetic track. A magnetic track may be positioned between a trap and a partition, along a channel, or a combination thereof. The magnetic track may be positioned in a different layer than the trap and partition, such as directly below or above. The device may comprise a partition, a channel, a trap, or a combination thereof to include structural resonance features. In some cases, a partition, a channel, a trap, or a combination thereof, may include varying widths, such as a partition having a cone-shape. The device may also comprise one or more valves, one or more sensors. The trap may be a hydrodynamic trap, a bubble trap, an optical trap, a trident trap, a physical barrier trap, a magnetic trap, an acoustic trap, a laser trap, or any combination thereof. An object or a plurality of objects may be introduced into the device, such as into a path. An object may be a cell, a bead, a liquid droplet, an embryo or fragment thereof, an organism or fragment thereof, or any combination thereof. The device may comprise an electrical conductor. The electrical conductor may produce a magnetic field. The electrical conductor may comprise one or more materials such as gold, silver, platinum, copper, or any combination thereof.

A surface or a portion of a surface of a path, a trap, a partition, a channel, or any combination thereof may comprise a coating or a surface modification. For example, a portion may be at least about 20%, 30%, 40%, 50%, 60%, 70%, 80%, 90% a surface area. A portion may be a bottom surface of a path, a trap, a partition, a channel, or any combination thereof. A portion may be a bottom surface and a side surface of a path, a trap, a partition, a channel, or any combination thereof. A portion may be a portion of a partition that is fluidically farthest from a trap. A coating may comprise a polyethylene glycol, a poly[oligo(ethylene glycol) methyl ether methacrylate], a zwitterionic polymer comprising carboxybetaine or sulfobetaine, a polytetrafluoroethylene or other fluoropolymer, or any combination thereof. A surface of a trap, a path, a channel, a partition, or any combination thereof, may comprise a polyethylene glycol, a poly[oligo(ethylene glycol) methyl ether methacrylate], a zwitterionic polymer comprising carboxybetaine or sulfobetaine, a polytetrafluoroethylene or other fluoropolymer, or any combination thereof. A coating may comprise collagen, fibronectin, laminin, chitosan, alginate, agarose, methylcellulose, poly-D-lysine, poly-L-lysine, a hydrogel, any combination thereof, or any other coating suitable for culturing adherent cells.

A device or a system may comprise one or more sensors. A sensor may be an optical sensor, an electrochemical sensor, an optoelectronic sensor, a piezoelectric sensor, a capacitance sensor, a magnetic sensor, a biosensor, a chemical sensor, a pressure sensor, or other. One or more sensors may measure a temperature, a pH, a volume of a liquid, a concentration of a compound, a change in a concentration of a compound, or any combination thereof. One or more measurements may be taken automatically, as directed by a control system. A measurement may be taken after a user initiates the measurement to be taken from a user interface of the control system. One or more measurements may be taken as part of an analysis of an object. One or more measurements may be taken as part of a device maintenance. One or more sensors may measure a concentration of a compound, or a change in a concentration of a compound. The compound may be an ion, a gas, a nutrient or fragment thereof, a buffer, a drug or fragment thereof, a protein or fragment thereof, a ligand or fragment thereof, a hormone or fragment thereof, a cytokine or fragment thereof, a chemokine or fragment thereof, a growth factor or fragment thereof, a carbohydrate or fragment thereof, a lipid or fragment thereof, a nucleic acid or fragment thereof, a cDNA, an siRNA, an shRNA, a microRNA, an sgRNA, an mRNA, a virus or fragment thereof, a retrovirus or fragment thereof, a lentivirus or fragment thereof, a kinase or fragment thereof, an enzyme or fragment thereof, an antibody or fragment thereof, an aptamer or fragment thereof, an antigen or fragment thereof, a micelle, a nanoparticle, a liposome, a microparticle, a lysis buffer, or any combination thereof. The compound may be the ion, and the ion may be $Ca^{2+}$, $Mg^{2+}$, or a combination thereof. The compound may be a gas. The gas may be oxygen, carbon dioxide, or a combination thereof. The compound may be a nutrient, such as glucose or an amino acid. One or more sensors may be disposed within a single partition. Each partition of a plurality of partitions may comprise at least one sensor. A sensor may be disposed at a trap or at a location of a path. A sensor may be disposed at a path inlet to the device. A sensor may be disposed at a path outlet to the device. A sensor may be disposed in a layer of the device that is different from the layer comprising the path, the trap, the channel, the partition, or any combination thereof.

A system may comprise the microfluidic device and a control module. The control module may direct the transfer of the object between the trap and the partition, such as applied a magnetic field to the magnetic track. The control module may individually address a partition, such as moving a single object from a single partition, wherein other partitions containing objects are not moved. The control module may collectively address a plurality of partitions, such as collectively transferring a plurality of objects from their respective traps to adjacent partitions. The control module may automate at least a portion of the method, such as a collective transfer. The control module may automate the entire method. The control module may accept input parameters from a user. The control module may be remotely controlled.

The system may comprise an imaging module. The imaging module may permit a user to visualize one or more traps, partitions, channels, paths, or combinations thereof of a device. The imaging module may measure one or more parameters and deliver the measured one or more parameters to the control module. The imaging module may measure one or more parameters to determine a phenotype, such as a cell phenotype. In some cases, the device may comprise a magnetic material such as a magnetic track, and the system may be operatively connected to a source of magnetic field. The control module may control application of the source of magnetic field to the device. The control module may involve the application an external rotating field to a portion of a microfluidic device, such as to a partition. The control module may control an external magnetic source to apply a magnetic field to the device or a portion of the device such as a partition.

The control module may maintain one or more parameters within a device. For example, a control module may direct a supply of heat from at least one heating element to the microfluidic device such that a set temperature is matched. The set temperature may be input to the control module by a user. A control module may direct a flow in a path, such that the flow may be ON when populating a plurality of traps, and the flow may be turned OFF during a transferring.

A method may comprise organizing a plurality of first objects into partitions of a device and organizing a plurality of second objects into partitions of the device. The first object in a partition may bind, conjugate, attach, or otherwise become associated with a second object in a partition. The association between the first object and the second object may be reversible. The first object and second object associated with one another may be collectively removed from a partition such that the association remains. After a first object and a second object are associated together, a first object or second object may be lysed, such as a first cell or a second cell. In some cases, a cell and a bead are associated together and after the association, the cell may be lysed. Components of the cell lysate may be reverse transcribed after a cell lysis. In some cases, a cell and a bead are associated together and after the association, sequence by synthesis is performed within a partition having the cell-bead association. In some cases, a surface of the partition may comprise capture oligonucleotides patterned on the surface, such as a bottom surface of the partition. In this case, a cell may be lysed and reverse transcribed RNA from the cell onto the capture oligonucleotide sequence patterned on the surface.

In some cases, before or after a cell and bead are associated together, a compound such as a drug or salt thereof or a vehicle control may be added to the partition containing the cell-bead association. The method may determine a drug-resistant cell in a plurality of cells. The method may collect a drug-resistant cell in a plurality of cells for further analysis. The method may identify a therapeutic compound effective for treating, for cure a disease or condition or reducing a side effect of a disease or condition or drug therapy. The disease or condition may be a cancer. The disease or condition may be an immunological disease, an infectious disease, a neurological disease, or a combination thereof.

The methods provided herein may be automated. The methods may be partially automated such as automation of the transferring. The control module may direct the automated method. Greater than about 10 cells may be organized in partitions in parallel. Greater than about 10 cells may be analyzed in situ within respective partitions in parallel. Greater than about 100 cells may be organized in partitions in parallel. Greater than about 100 cells may be analyzed in situ within respective partitions in parallel. Greater than about 1,000 cells may be organized in partitions in parallel. Greater than about 1,000 cells may be analyzed in situ within respective partitions in parallel. Greater than about 2,000 cells may be organized in partitions in parallel. Greater than about 2,000 cells may be analyzed in situ within respective partitions in parallel.

In some cases, an object may be a bead and the bead may be associated with a molecule that adheres to a membrane of a virus particle, such as an outer membrane. Associating a bead having the molecule with a cell may determine a level of virus particle in a partition or a level of virus particle being secreted by the cell to which the bead is associated. In some cases, the molecule associated with the bead, may be conjugated to the bead. In some cases, the molecule captures one or more virus particles secreted by the cell to which the bead is associated, captures one or more virus particles secreted by one or more cells within a same partition as the cell to which the bead is associated, captures one or more virus particles secreted by one or more cells adjacent to the cell to which the bead is associated, or any combination thereof.

A first set of objects may be organized into partitions, such that a single first object is located in a single partition. A second set of objects may be organized into the same partitions, such that a second object joins a first object located in the single partition. The first and second object may be the same, such as a same type of cell, to form a homogeneous set. The first and second object may be different, such as a cell and a bead, to form a heterogeneous set. The heterogeneous set may comprise two different cell types. For example, the heterogeneous set may comprise two different immune cells. In this case, the method may be used to analyze immunological interactions. The heterogeneous set of two or more cells may comprise immune cells, cancer cells, or a combination thereof. In this case, the method may be used to study immune surveillance or immunotherapies. The heterogeneous set of two or more cells may comprise neuron cells, muscle cells, or a combination thereof. In this case, the method may be used to study the formation of neuromuscular junctions. The heterogeneous set of two or more cells may comprise neuron cells, glial cells, astrocytes, or any combination thereof. In this case, the method may be used to study neuronal signaling and/or drug-dependence. The heterogeneous set of two or more cells may comprise tumor cells, endothelial cells, epithelial cells, macrophages, neutrophils, NK cells, fibroblasts, stromal cells, smooth muscle cells, adipocytes, or any combination thereof. In this case, the method may be used to study a tumor microenvironment. The homogeneous set or the heterogeneous set of two or more cells may comprise a pair of adherent cells. In this case, adhesion between the pair of adherent cells may be studied. The heterogeneous set of two or more cells may comprise an immune cell and a pathogen. In this case, an interaction between the immune cell and the pathogen is analyzed. The heterogeneous set of two or more cells may comprise a leukocyte and an endothelial cell. In this case, an interaction between the leukocyte and the endothelial cell may be analyzed. The heterogeneous set of two or more cells may comprise a pair of cells. In this case, the pair of cells may be used to analyze a tight junction, a gap junction, a junction involving direct contact between membranes of the pair of cells, or any combination thereof.

FIG. 1 shows an illustration of a two-step transfer process using a microfluidic device as shown in (FIG. 1a). First, one or more cells may enter a path as shown in (FIG. 1b), may be hydrodynamically trapped in obstacles disposed in the flow stream as shown in (FIG. 1c), and then may be transferred into adjacent partitions using magnetic force as shown in (FIG. 1d). This process may be repeated for a second cell that is the same or different than the first, or may be repeated with a different object such as a bead, as shown in FIG. 1e-g.

Figure 2:
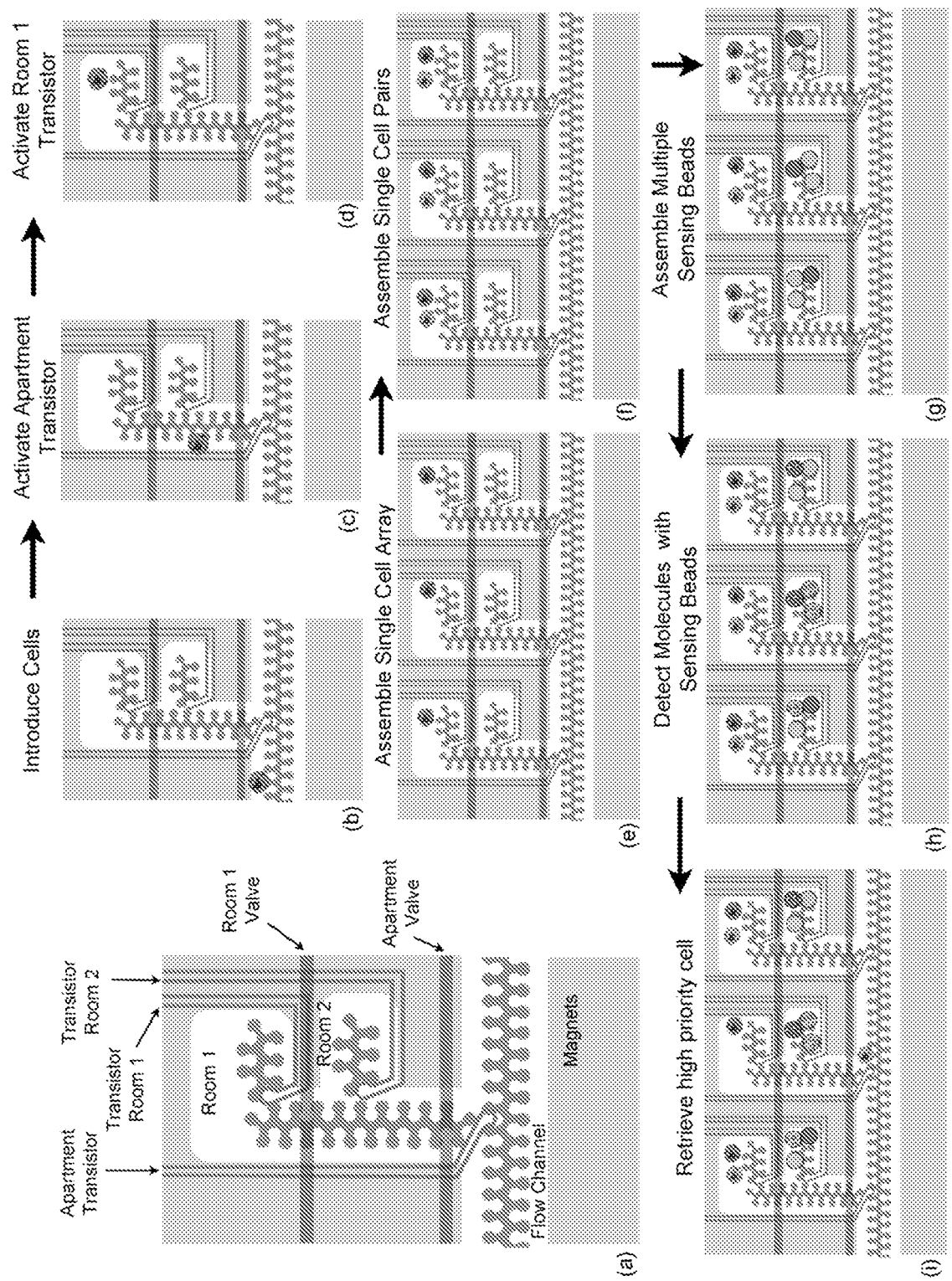
FIG. 2a-i shows an alternative two-step transfer process, which employs a different type of trap.

FIG. 2a shows an alternative embodiment two-step transfer process illustrated in FIG. 1, which uses a different type of hydrodynamic trap. An object such as a cell may be introduced into a path (FIG. 2b), a partition transistor may be activated (FIG. 2c), a room transistor may be activated (FIG. 2d). Multiple cells may be collectively transferred into partitions to assemble single cell arrays (FIG. 2e). Additional objects, such as cells or beads may be subsequently collectively transferred into the partitions having the cells, to assemble single cell pairs (FIG. 2f). Additional objects, such as sensing beads, may be transferred to partitions adjacent to a partition housing one or more cells (FIG. 2g). Detection of molecules secreted by one or more cells may be detected by the sensing beads (FIG. 2h). One or more cells, such as high priority cells, or cells of interest may be collectively or selectively retrieved from their respective partitions (FIG. 2i).

Figure 3:
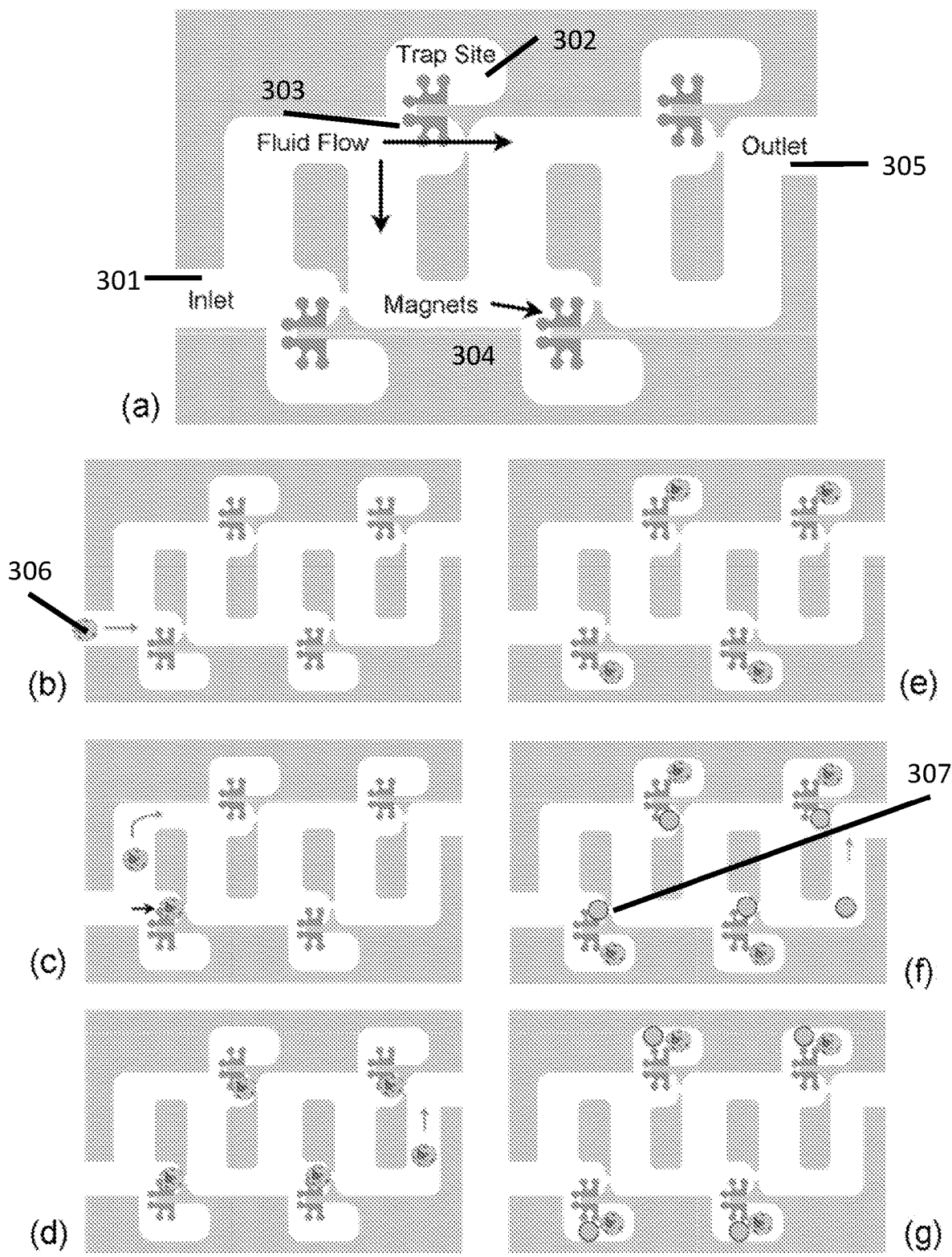
FIG. 3a-g shows an alternative two-step transfer process, which employs a different type of trap.

FIG. 3 shows another embodiment two-step transfer process illustrated in FIG. 1, which uses a different type of hydrodynamic trap as shown in FIG. 3a. Objects may enter a path 301 and travel along the travel until becoming trapped in a hydrodynamic trap 303. Magnetic tracks 304 may transfer objects such as a magnetically labeled bead or cell from the trap into a partition 302 adjacent thereto the trap. One or more objects may also be collectively or selectively removed from the partition and collected at an outlet 305. A first object such as a first cell 306 may enter a path, such as a microfluidic flow channel as shown in FIG. 3b. The first cell may be trapped in a hydrodynamic trap as shown in FIG. 3c, whereas a second object, such as a second cell may pass the first trap and travel further along the path to a second available trap, as shown in FIG. 3d. Objects may enter the flow path until all available traps are loaded with an object. All of the trapped objects may then be transferred into respective partitions that are adjacent thereto each of the traps, as shown in FIG. 3e. The traps may then be available to trapped additional objects such as cells or beads 307 as shown in FIG. 3f. After which, those traps objects may also be collectively transferred into the same partitions as shown in FIG. 3g.

Figure 4:
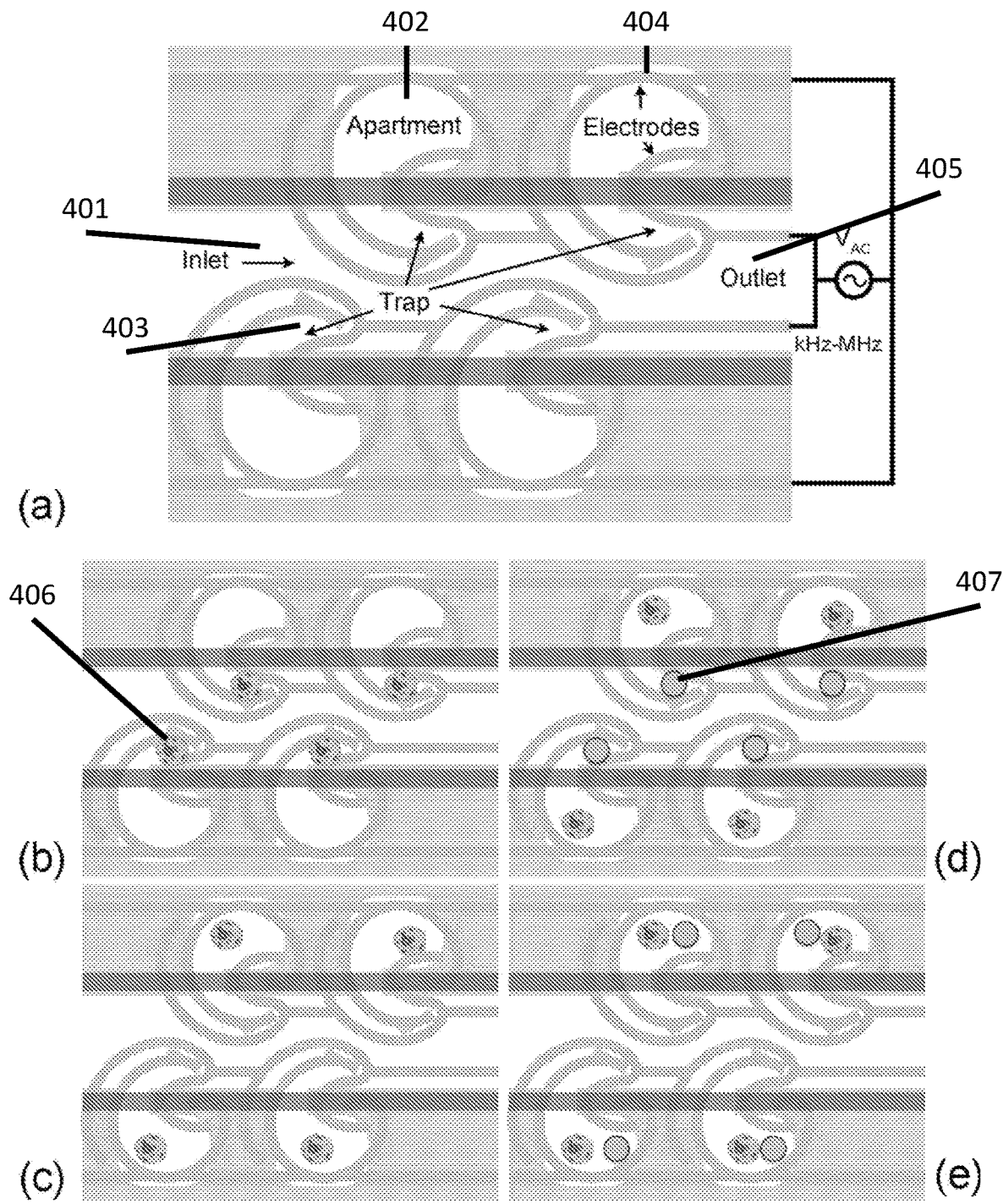
FIG. 4a-e shows a two-step transfer process to first hydrodynamically trap objects in traps disposed in a flow path, and then transfer the trapped object into a partition using electric field induced motion.

FIG. 4 illustrates a two-step transfer process. Objects may enter a path 401 and travel along the travel until becoming trapped in a hydrodynamic trap 403. An electric field induced force 404 may transfer objects from the trap into a partition 402 adjacent thereto the trap. One or more objects may also be collectively or selectively removed from the partition and collected at an outlet 405 as shown in FIG. 4a. First, objects 406 are hydrodynamically trapped in obstacles disposed in the flow stream (FIG. 4b), and then transfer into the partitions using the electric field induced force (FIG. 4c). The same two step transfer process may be repeated for a different object, such as a different cell or a bead 407, as shown in FIG. 4d-e.

Figure 5:
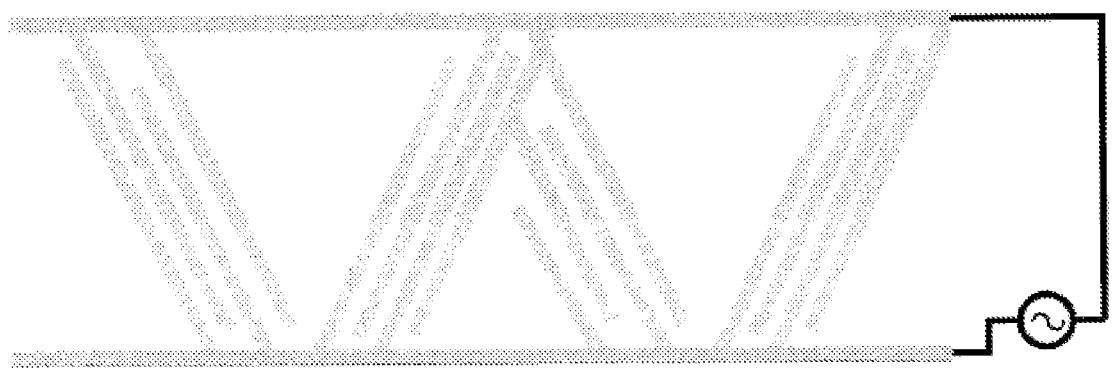
FIG. 5 shows an alternative electric field induced transferring geometry with an arrow format to direct cells into a section of a partition.

FIG. 5 demonstrates an alternative electric field induced transferring geometry. Similar to the embodiment of FIG. 4, this geometry uses arrow format to direct cells into the field minimum of the apartment.

Figure 6:
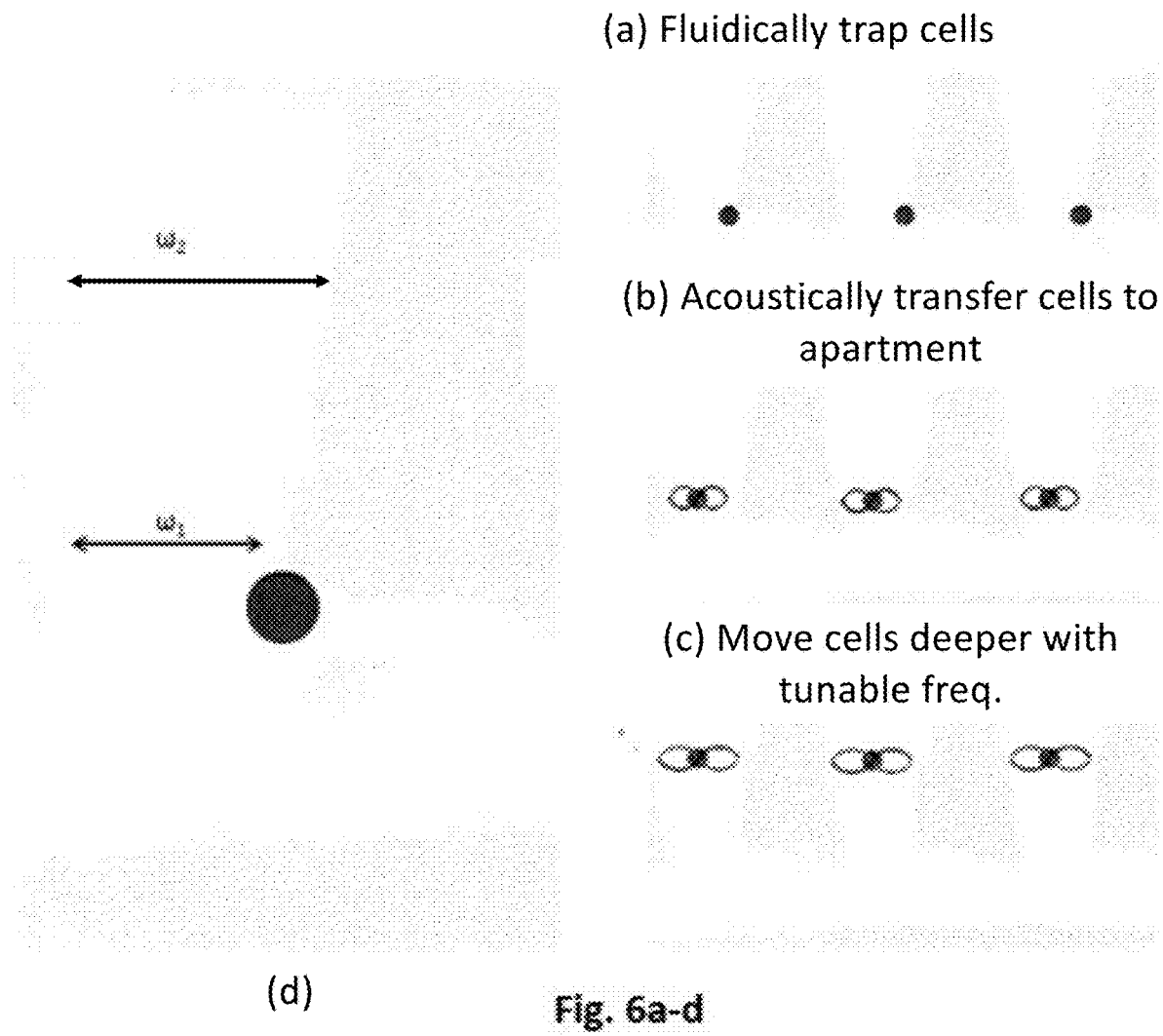
FIG. 6a-d shows a two-step transfer process to first trap objects in traps disposed in a flow stream, and then transfer the trapped object into a partition using a standing acoustic wave.

FIG. 6 illustrates a two-step transfer process to first hydrodynamically trap object in obstacles disposed in the flow stream (FIG. 6a), and then transfer the trapped object into the partitions using a standing acoustic wave (FIG. 6b). The apartment is designed to have gradually increasing width to allow the position of the focal point to be tuned with the acoustic frequency. For demonstration purposes, w1 is a frequency resonant with the entrance of the apartment, which is used to transfer the cell from the hydrodynamic trap into the apartment. If the acoustic frequency is adjusted to w2, which is resonant with a location further in the interior of the apartment, the cell can be moved into the apartment's interior. A smooth transition of the cell location can be achieved by smoothly adjusting the frequency from w1 to w2 (FIG. 6c-d).

Figure 7:
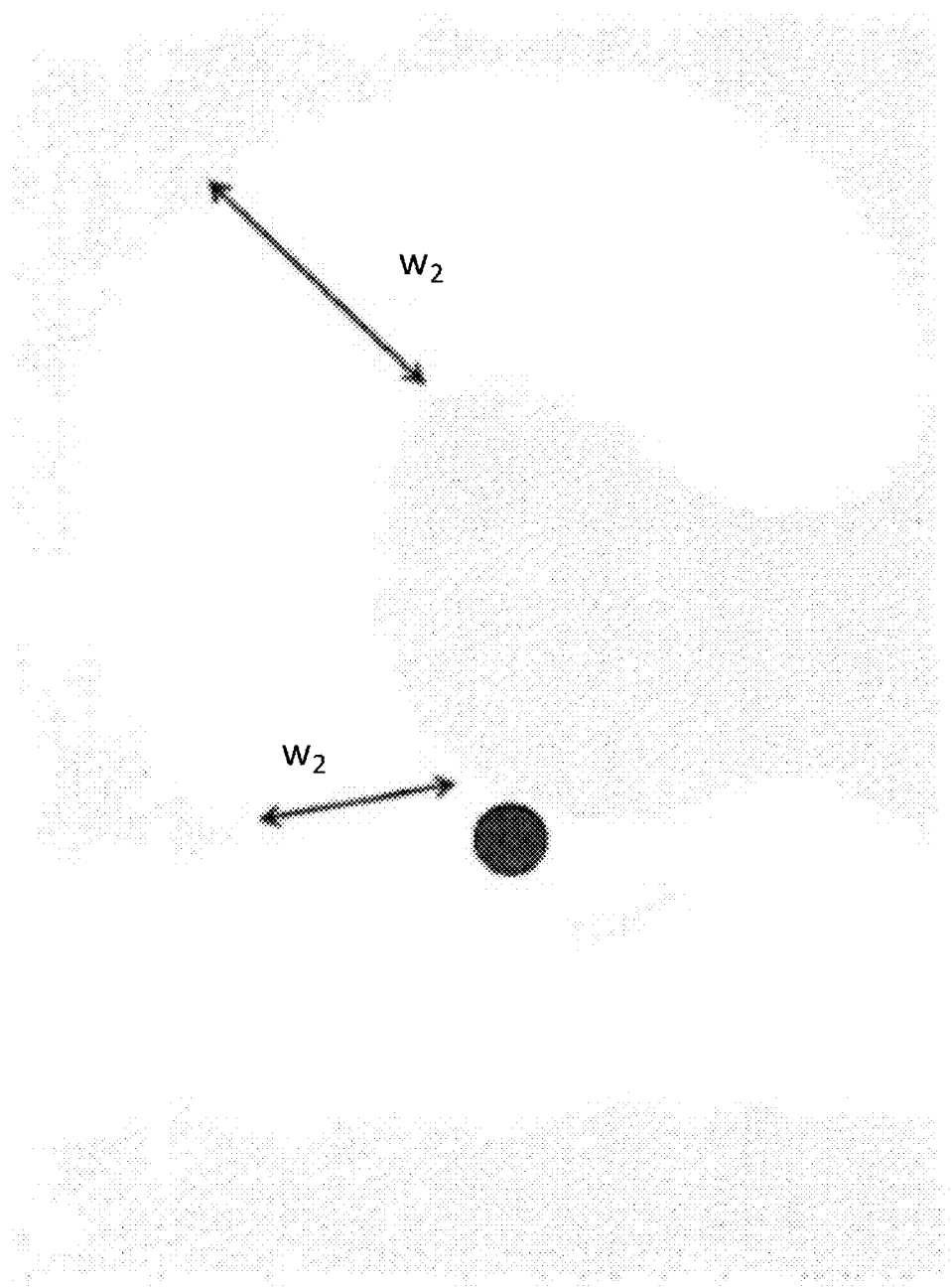
FIG. 7 shows an alternative acoustic transferring geometry to FIG. 6.

FIG. 7 illustrates an alternative acoustic transferring geometry is shown. Similar to the embodiment of FIG. 6, this geometry has gradually increasing apartment width, but instead is designed with a curved geometry to provide for better hydrodynamic shielding of the trapped cells.

Figure 9A:
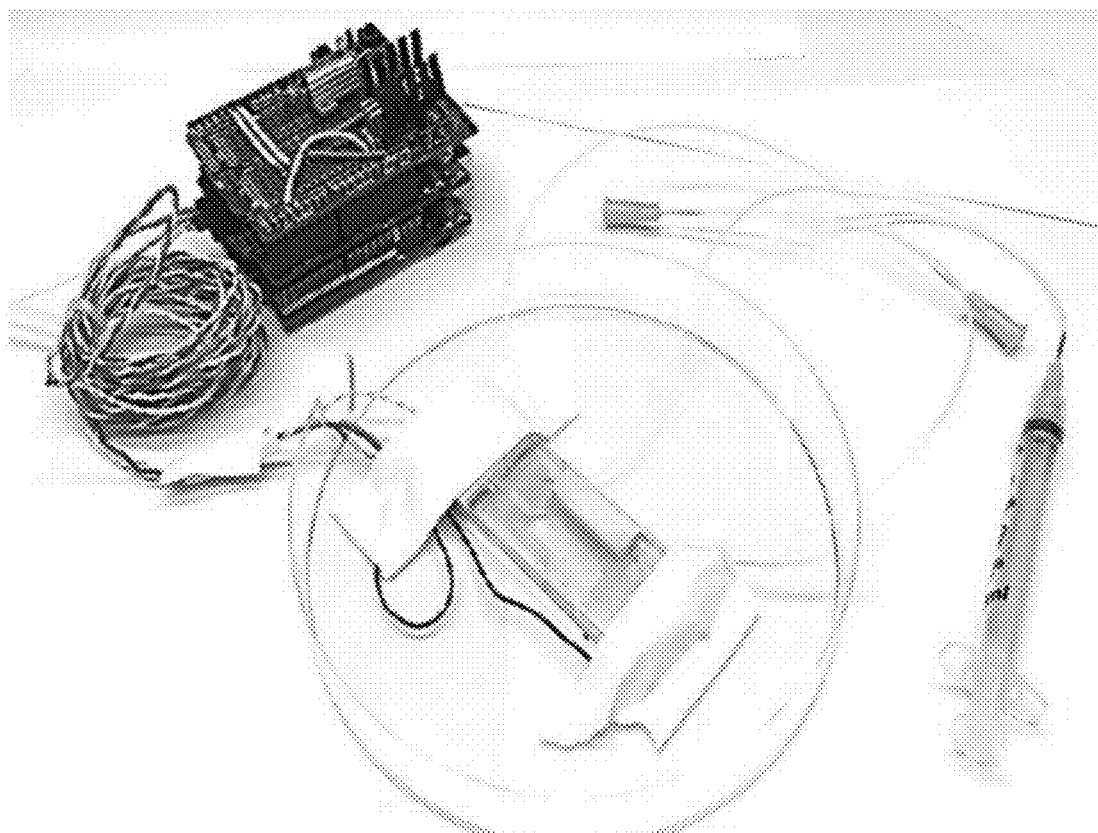
FIG. 9a shows temperature control maintained on a microfluidic chip.
Figure 9B:
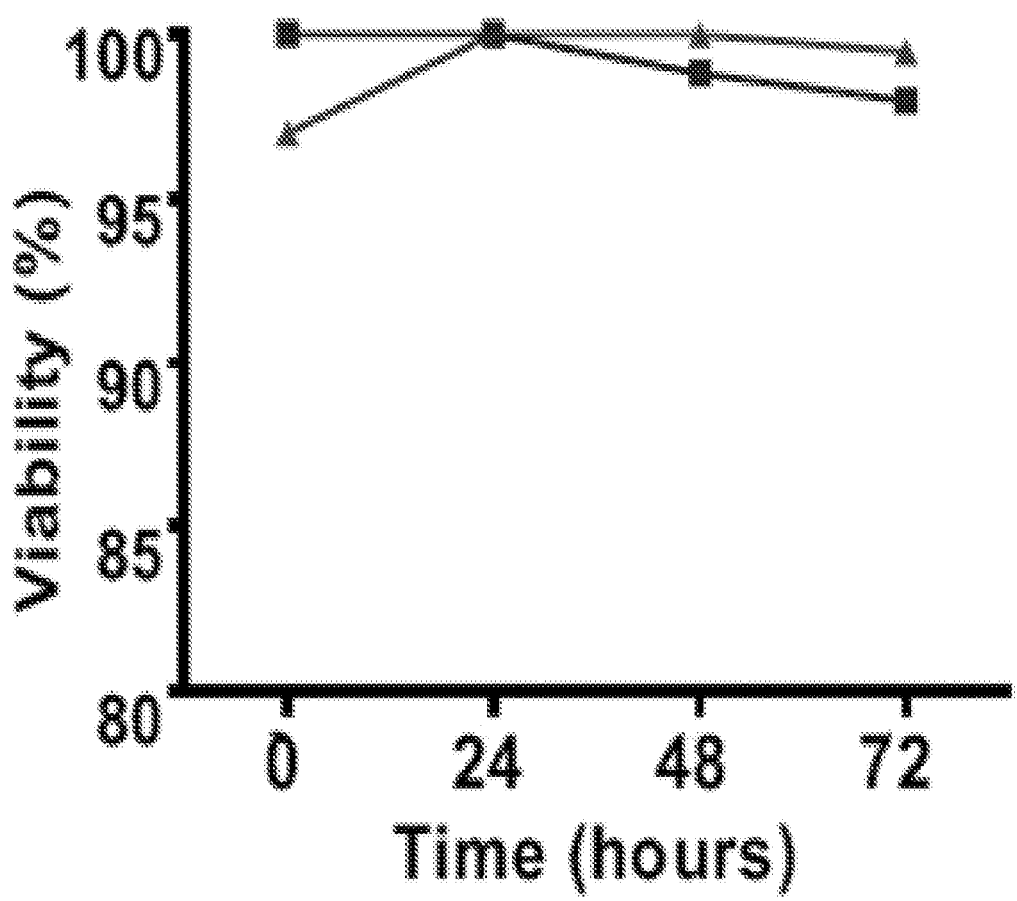
FIG. 9b shows short-term incubator studies showing cell viability past 72 hours.

FIG. 9a-b illustrates data for preliminary cell viability studies conducted in sealed PDMS chambers maintained at 37° C., with gas exchange mediated by diffusion of CO2 through the PDMS membrane. Short-term incubator studies indicate that cells remain viable past 24 hours. Viability was assessed with Cytox staining kit at 6-hour intervals.

Figure 11A:
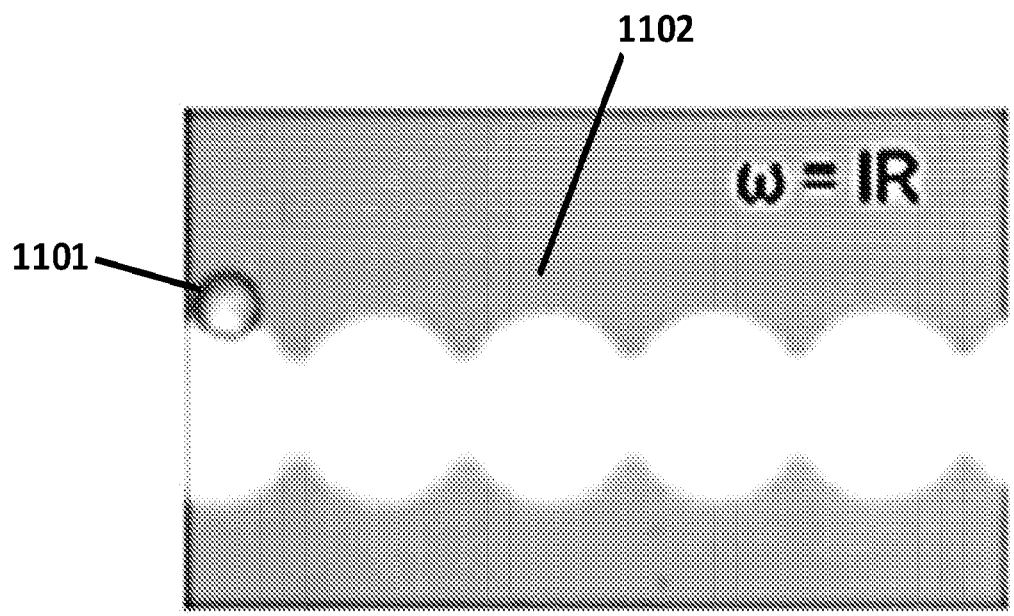
FIG. 11a-e shows integrated magnetic circuits used to organize single cells into arrays.
Figure 11B:
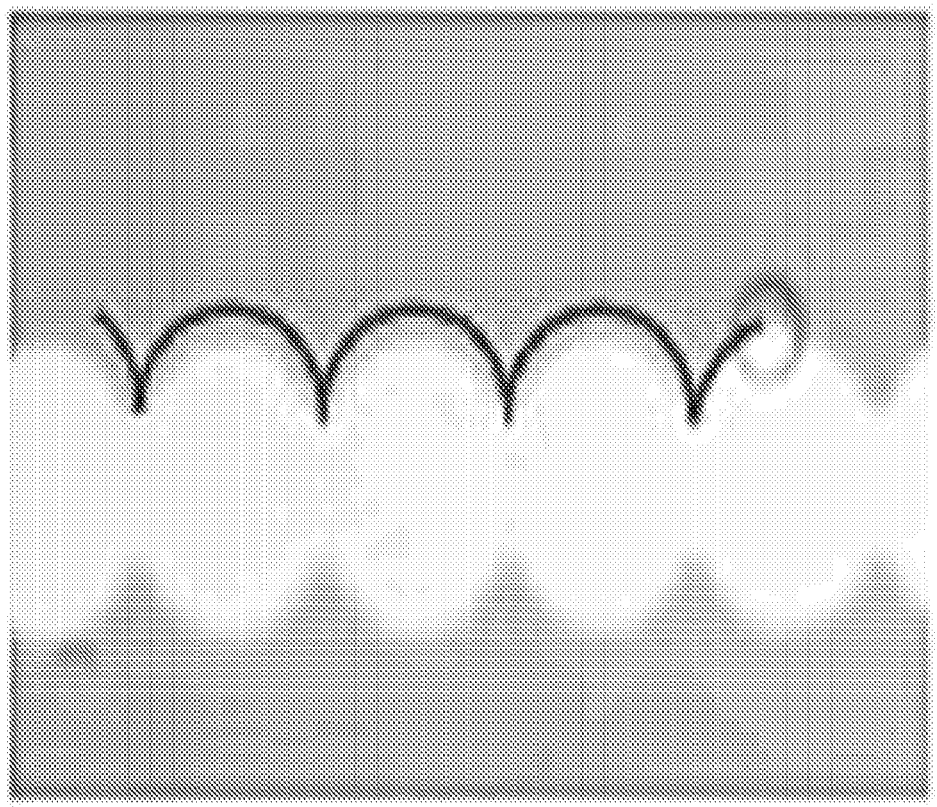

FIG. 11a-b illustrates one of the basic components (i.e. a "conductor") of a magnetophoretic single cell memory device. CD4$^+$ T cells may be labeled with magnetic nanoparticles (Stem Cell nanoparticles, 200 nm diameter, CD2$^+$ antigen) and may be moved in a rotating magnetic field along linear tracks of $Ni_{81}Fe_{19}$ patterned magnetic films. The path followed by the magnetically-labeled cells is indicated by the grey line in the lower part of the figure. Cell speed may be proportional to the driving frequency, ω, which may be the equivalent of Ohm's law for matter, ω=IR. As illustrated in FIG. 11a-b, the magnetic tracks may constitute magnetophoretic "conductors", where magnetically-susceptible objects may be transported with a mean velocity that may be linear related to the frequency with which the external magnetic field may be modulated.

Figure 11C:
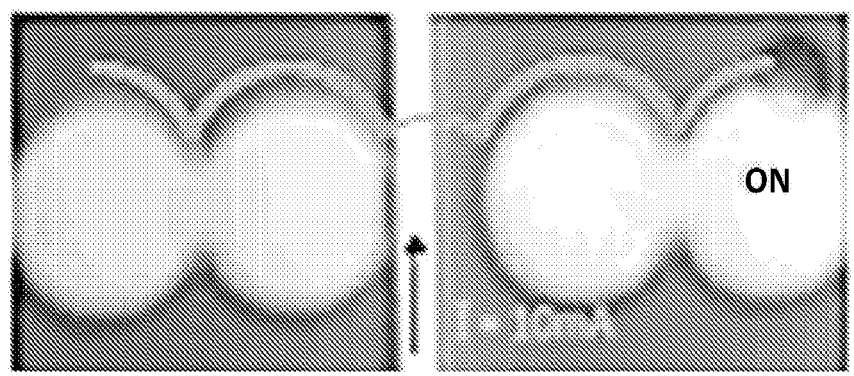
Figure 11D:
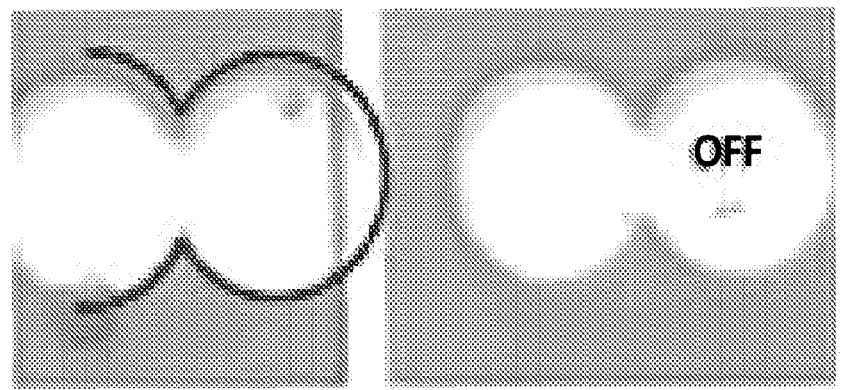

FIG. 11c-d illustrates one non-limiting example of the basic switching component (i.e. a "transistor") of a magnetophoretic single cell memory device. Cells can be switched between different tracks by the application of electrical current to the gate. When the gate current is ON, the cells may be transferred across the gap (light grey line), whereas the cells may not be transferred when the gate current is OFF (dark grey line).

Figure 11E:
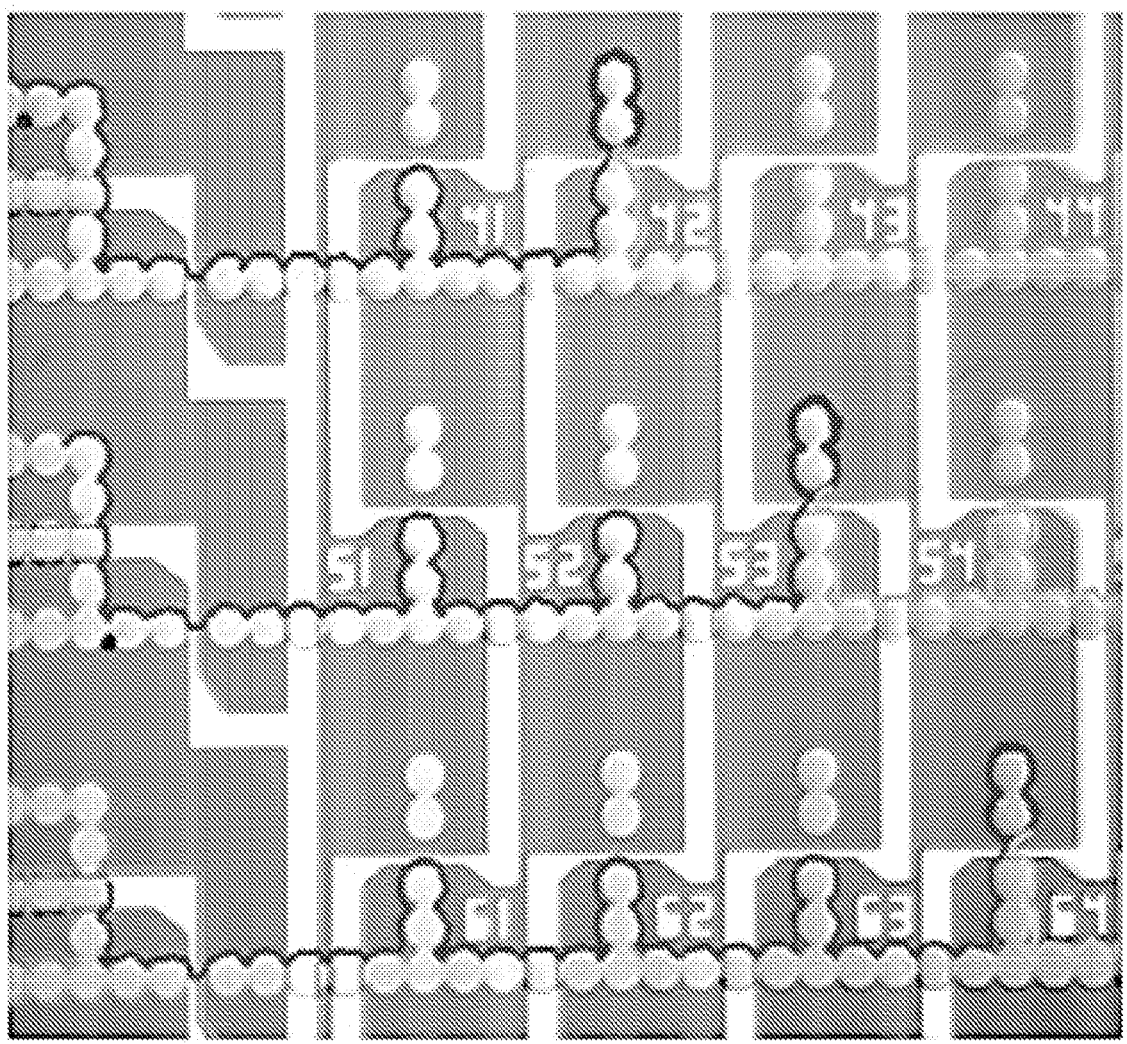

FIG. 11e illustrates the importing and exporting of single magnetic beads into multiplexed magnetophoretic arrays. Magnetic beads with 2.8-μm diameter may be imported into the "42", "53", and "64" microchambers of the array, with trajectories shown as dark grey lines. After assembly, the beads can be removed with the trajectories shown as light grey lines.

Figure 13:
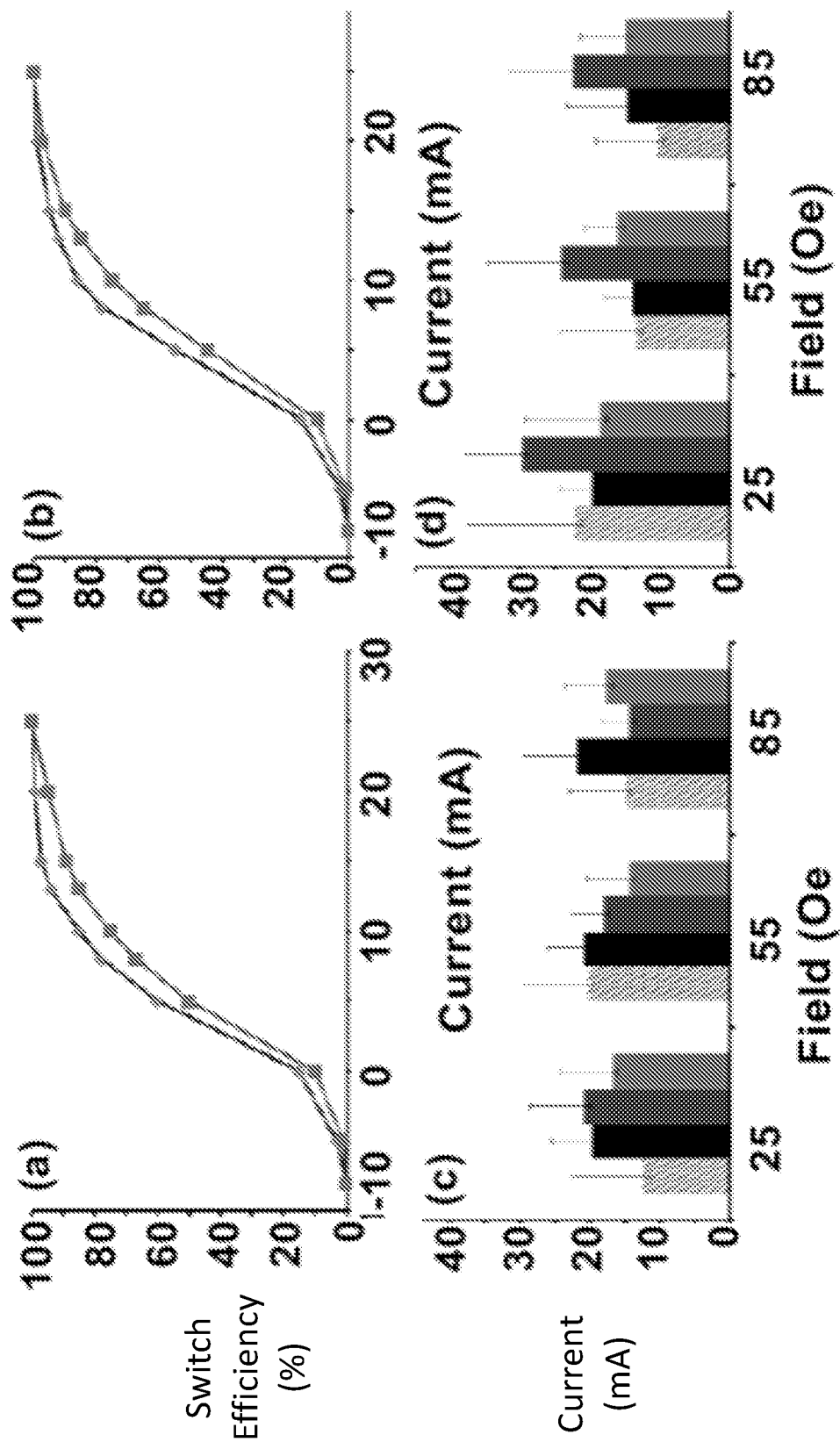
FIG. 13a-d shows a switching efficiency in an attractive mode (a, c) and a switching efficiency in a repulsive mode (b, d) for a magnetophoretic transistor.

FIG. 13a-d show data for "transistor" switching efficiency for magnetically-labeled CD4$^+$ T cells. Switching efficiency for operating frequencies of 0.2 Hz (squares) and 0.5 Hz (triangles) in FIG. 13a (repulsive mode), and FIG. 13b (attractive mode), with an in-plane rotating magnetic field operating at 45 Oe. Switching thresholds for various transistor geometries are shown in FIG. 13c (repulsive mode) and FIG. 13d (attractive mode).

Figure 12:
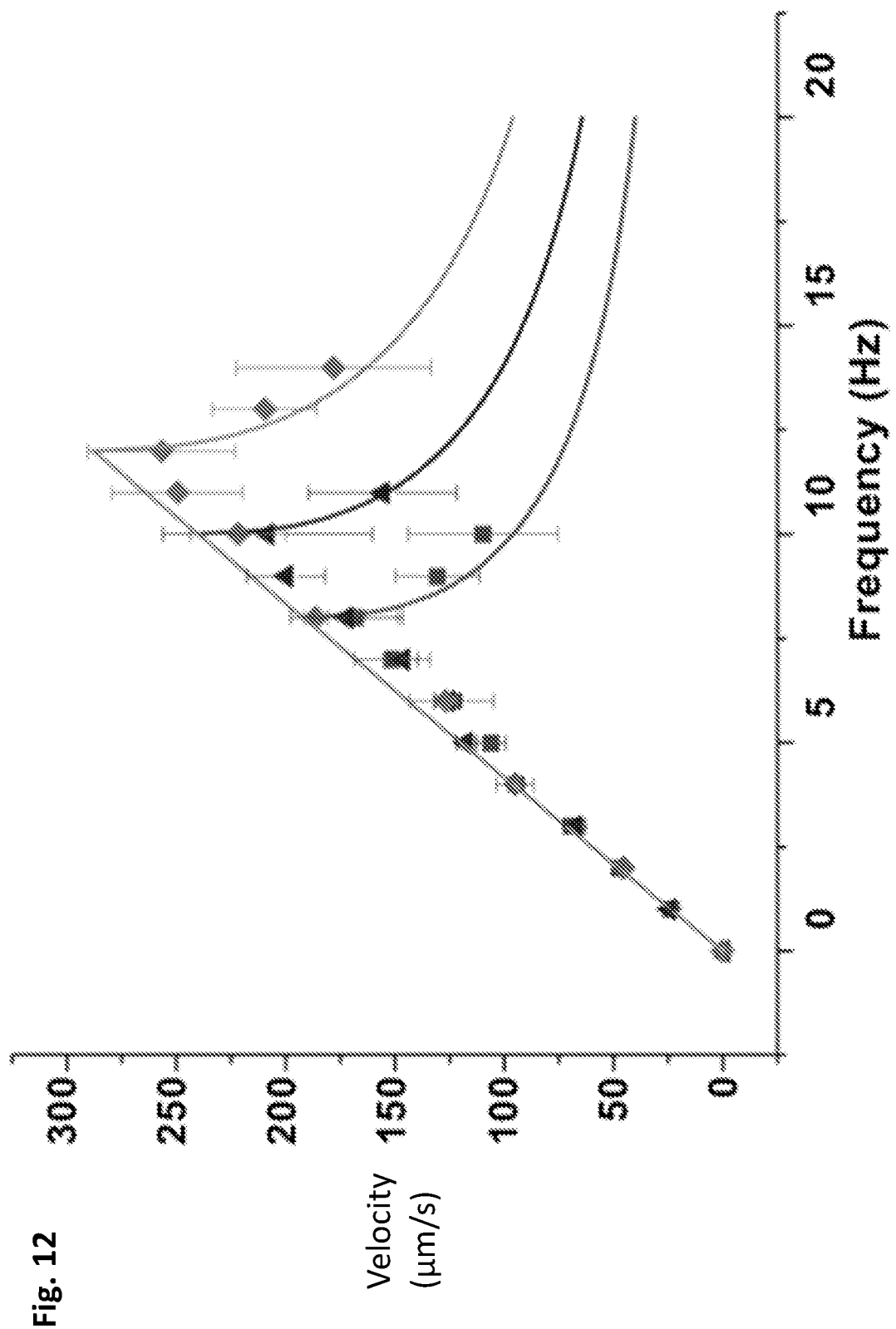
FIG. 12 shows a velocity versus a frequency for a magnetophoretic conductor.

FIG. 12 shows the linear relationship between velocity and frequency below 10 Hz is equivalent to Ohm's law for electronic circuits. The red, blue and green curves and points represent rotating field strengths of 50 Oe, 100 Oe, and 150 Oe, respectively.

Figure 14:
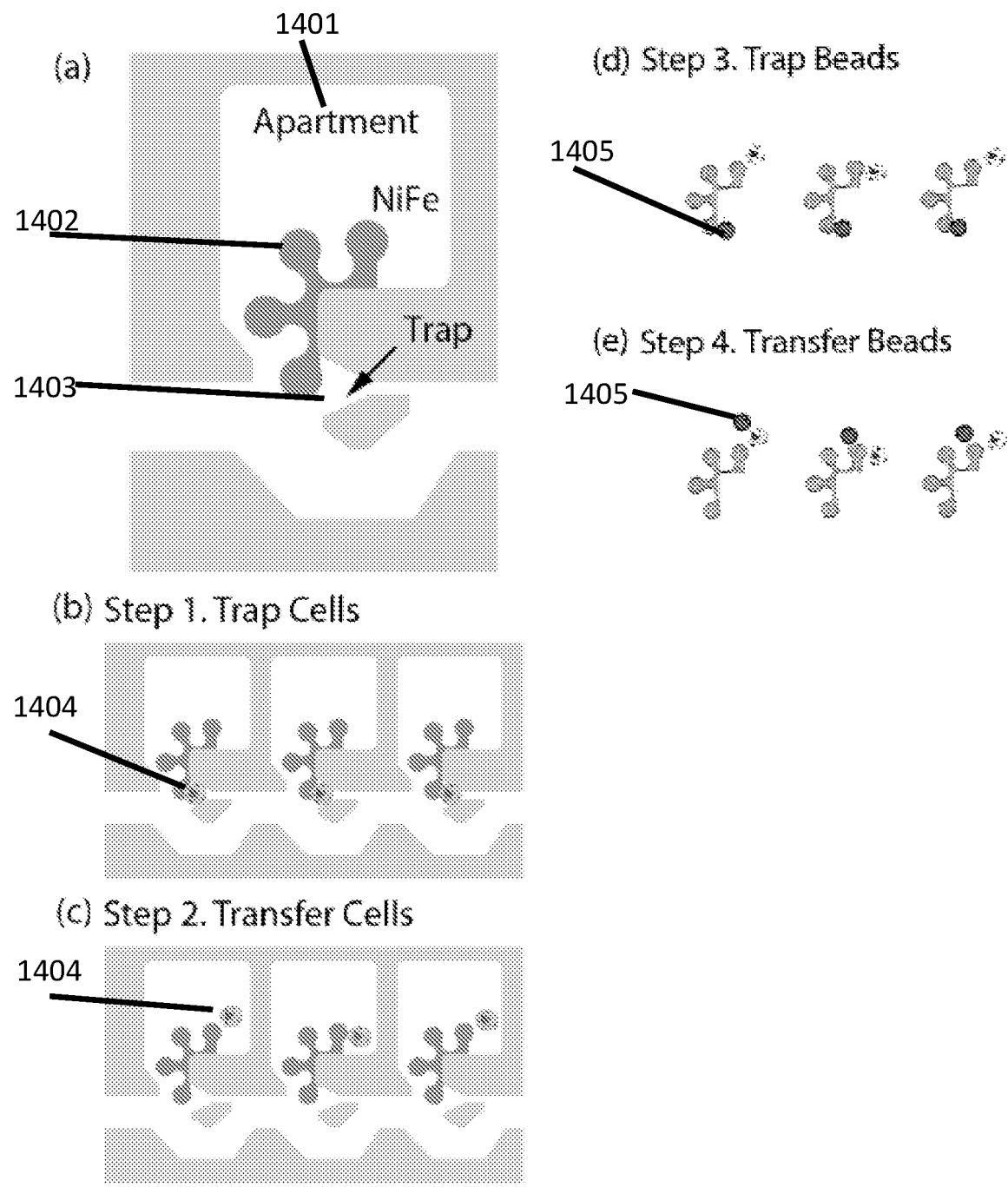
FIG. 14a-e shows a two-step method for organizing a single cell array.

FIG. 14a shows an alternative embodiment wherein the microfluidic chip comprises a trap 1403, a partition such as an apartment 1401 adjacent thereto the trap, a track 1402 such as a metallic track positions between the trap and the partition. In some cases, an object such as a cell 1404 may be introduced into a path of the device after which the object becomes trapped (FIG. 14b) and subsequently transferred into the partition (FIG. 14c). Additional steps may include trapping other additional cells or beads and transferring those addition objects into the partitions adjacent thereto (FIG. 14d-e).

Figure 16:
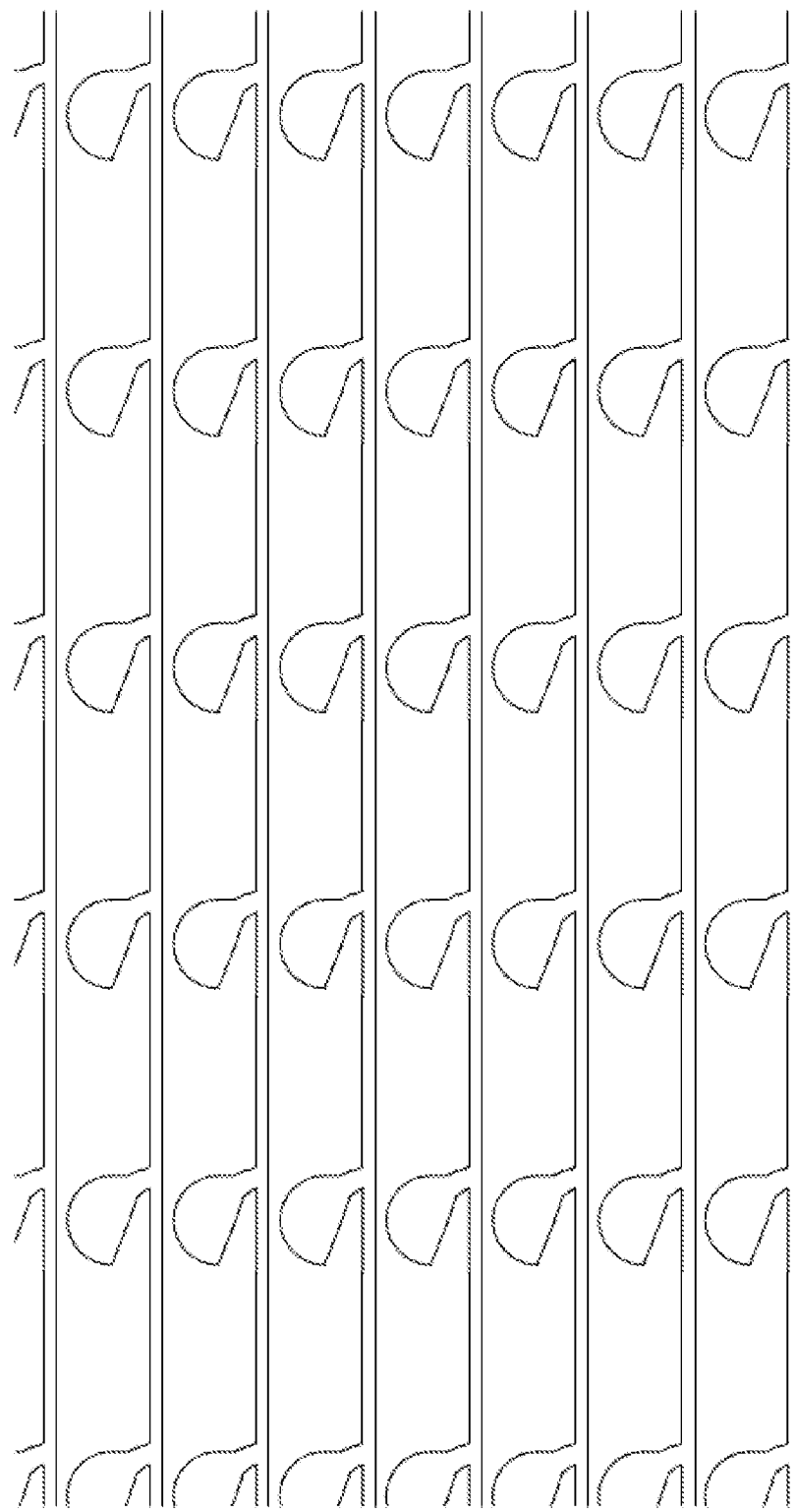
FIG. 16 shows one example of a partition, in which the position of the object can be adjusted by changing the frequency of an acoustic wave.

FIG. 16 shows one embodiment of a partition, in which the object's position can be changed by adjusting the acoustic frequency.

Figure 17:
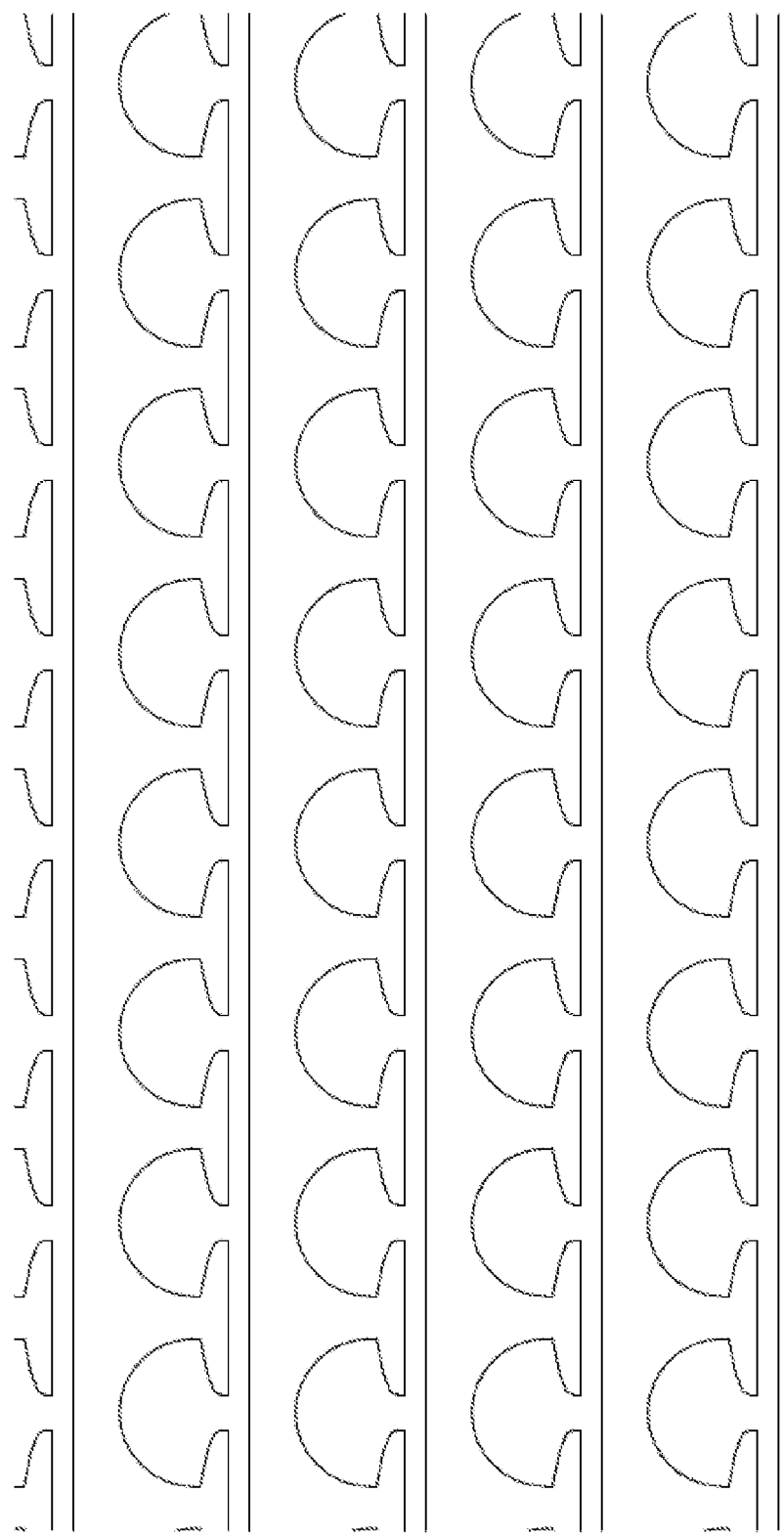
FIG. 17 shows one example of a partition, in which the position of the object can be adjusted by changing the frequency of an acoustic wave.

FIG. 17 shows one embodiment of a partition, in which the object's position can be changed by adjusting the acoustic frequency.

Figure 20:
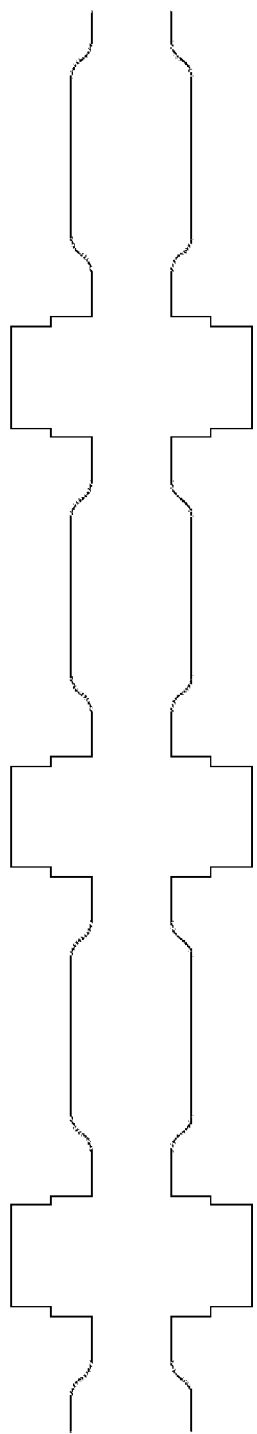
FIG. 20 shows one example of a partition, in which the position of the object can be adjusted by changing the frequency of an acoustic wave.

FIG. 20 shows one embodiment of a partition, in which the object's position can be changed by adjusting the acoustic frequency.

Figure 33A:
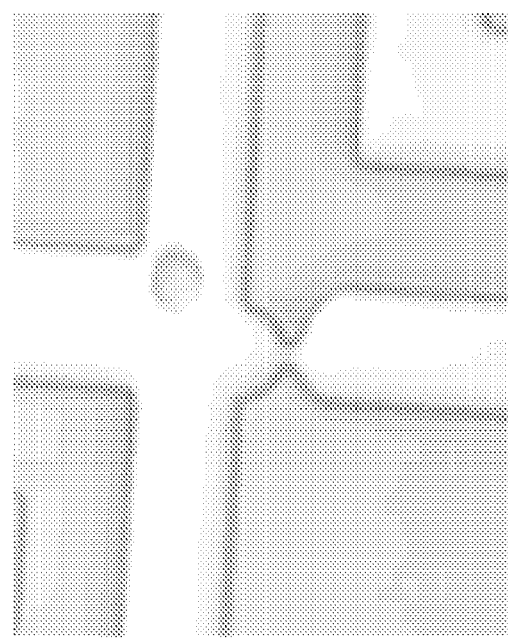
FIG. 33a-d shows a series of images in which a cell is able to squeeze through the hydrodynamic trap.
Figure 33B:
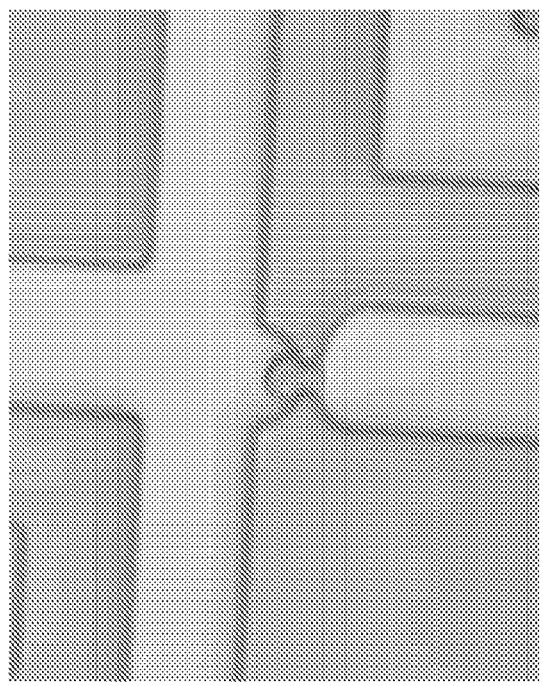
Figure 33C:
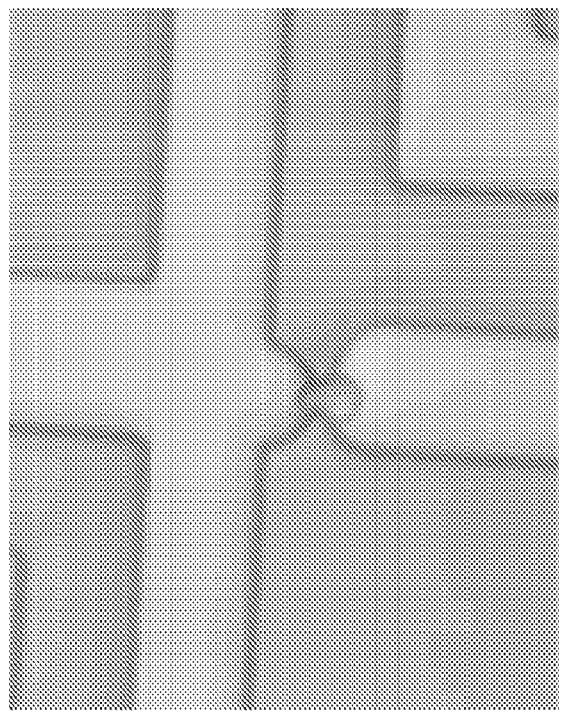
Figure 33D:
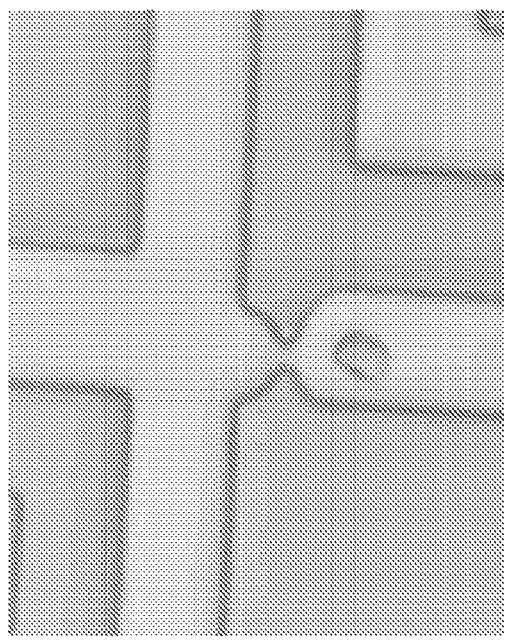

FIG. 33a-b shows an example of a hydrodynamic trap that is too wide, and allows a cell to squeeze through the gap. The cell is exposed to the flow field of the trap (FIG. 33a) and then becomes trapped (FIG. 33b), becomes squeezes in the trap (FIG. 33c) and finally exits the trap on the other side (FIG. 33d).

Figure 34:
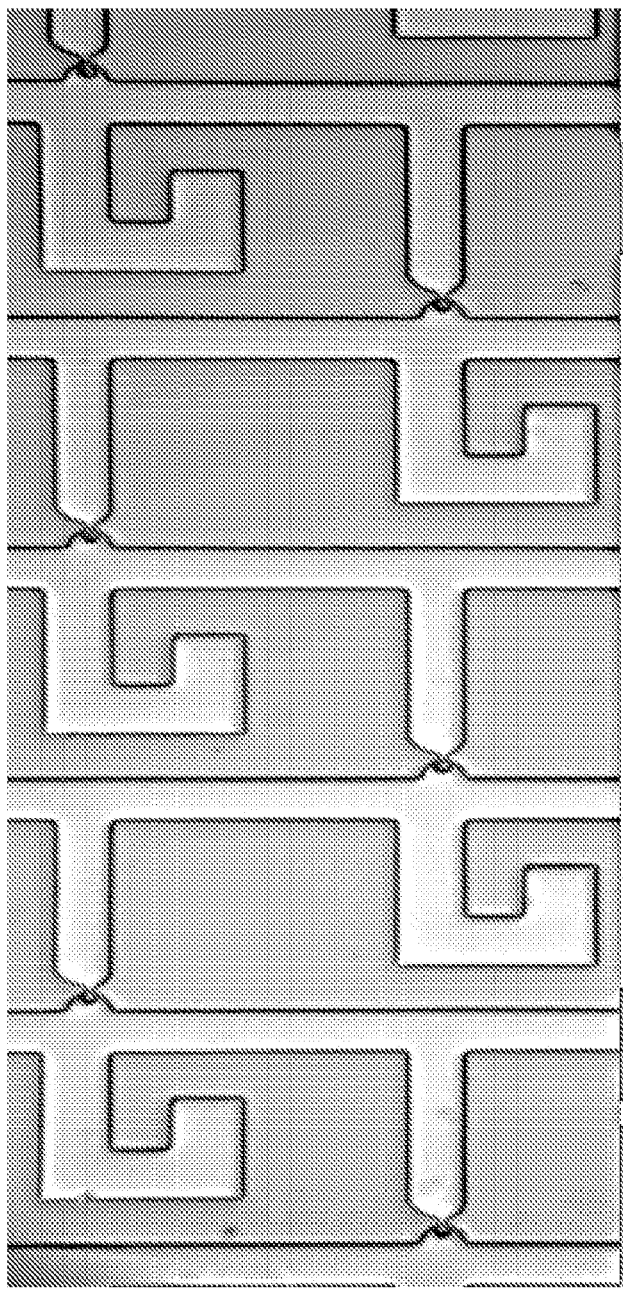
FIG. 34 shows multiple beads trapped in individual traps.

FIG. 34 shows an example of an array of hydrodynamic traps that capture single beads.

Figure 15:
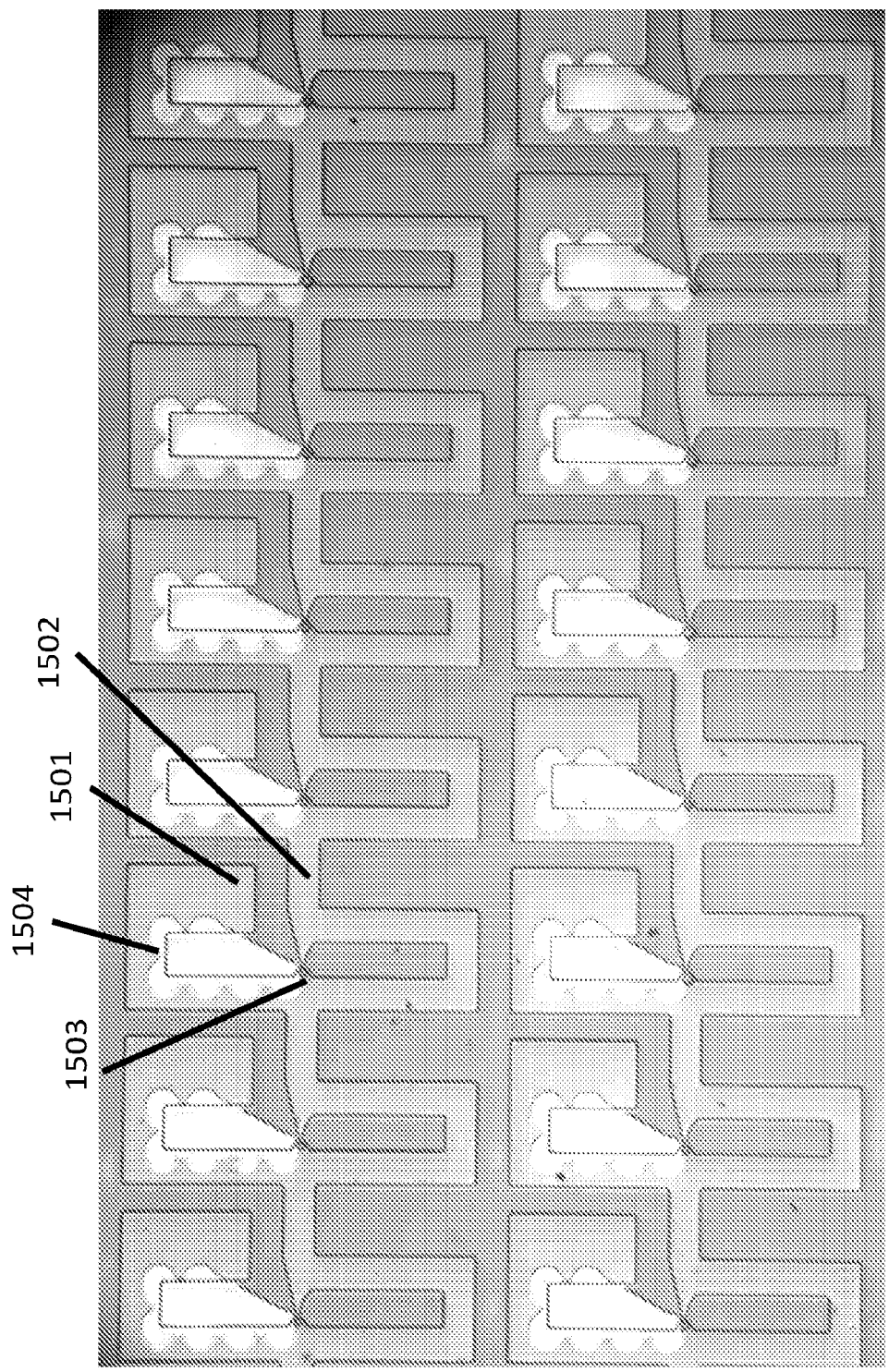
FIG. 15 shows two rows on a microfluidic device of apartments and adjacent traps in series fluidically connected by a path.
Figure 18:
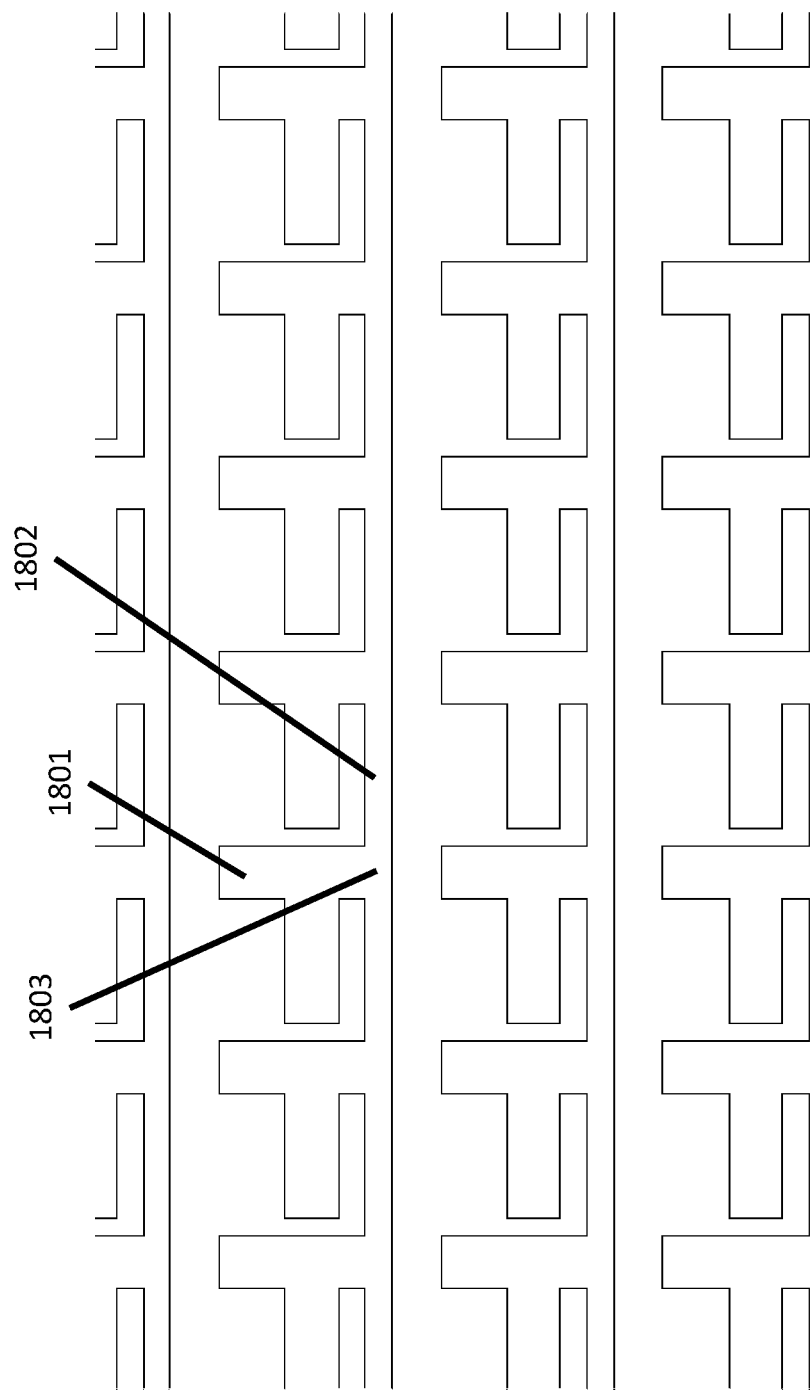
FIG. 18 shows an example of partitions and adjacent traps in series fluidically connected by a path.
Figure 19:
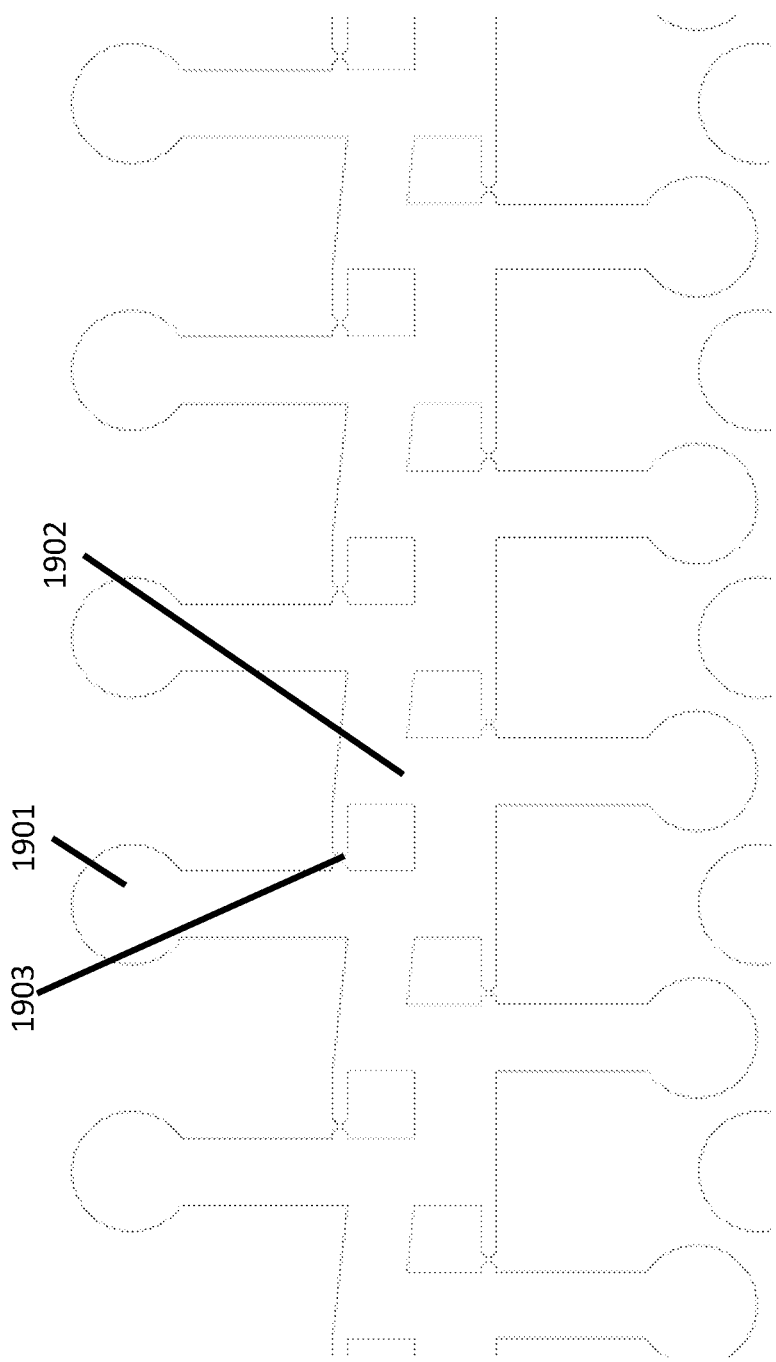
FIG. 19 shows an example of apartments and adjacent traps in series fluidically connected by a path.
Figure 21:
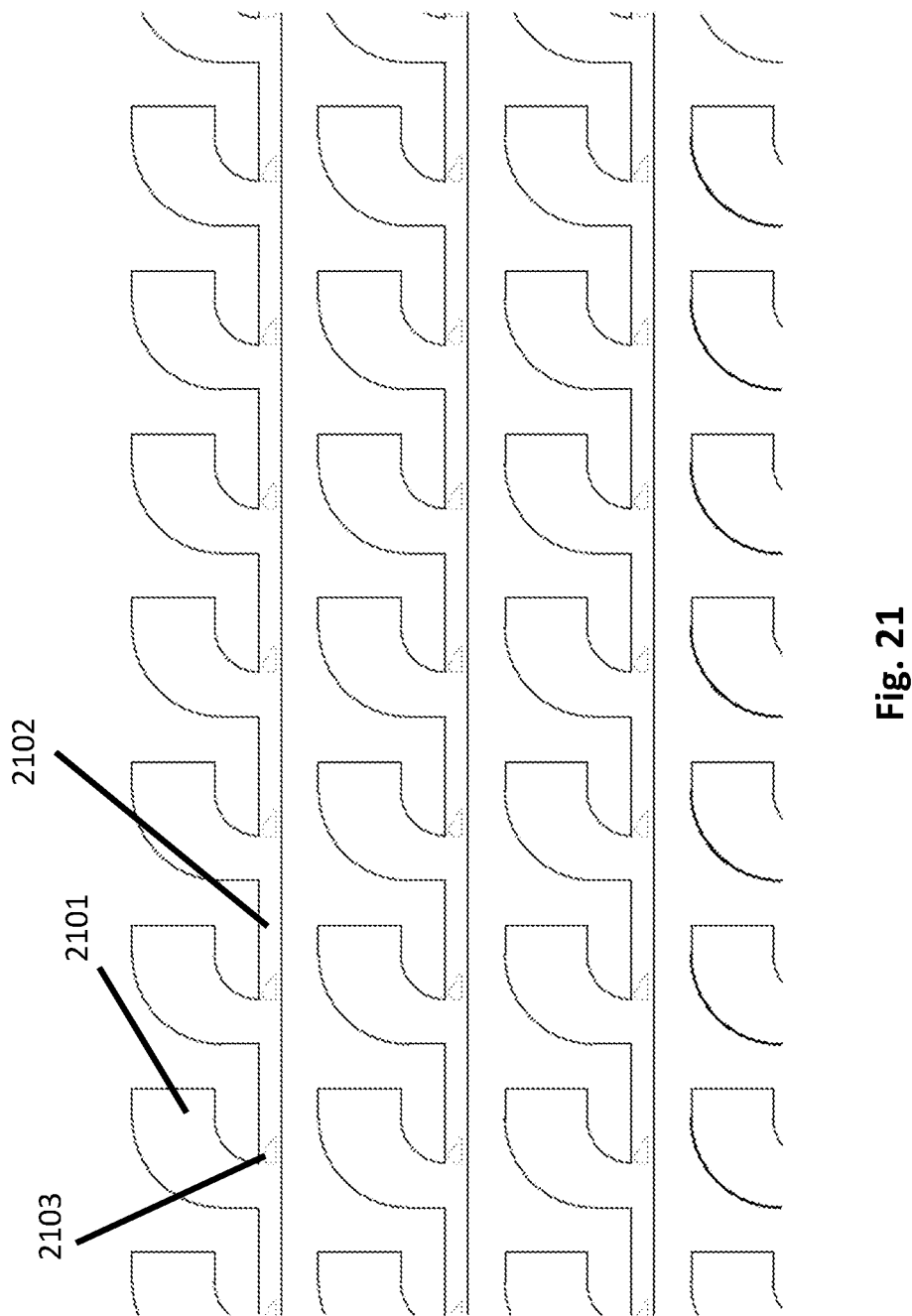
FIG. 21 shows an example of apartments and adjacent traps in series fluidically connected by a path.
Figure 32A:
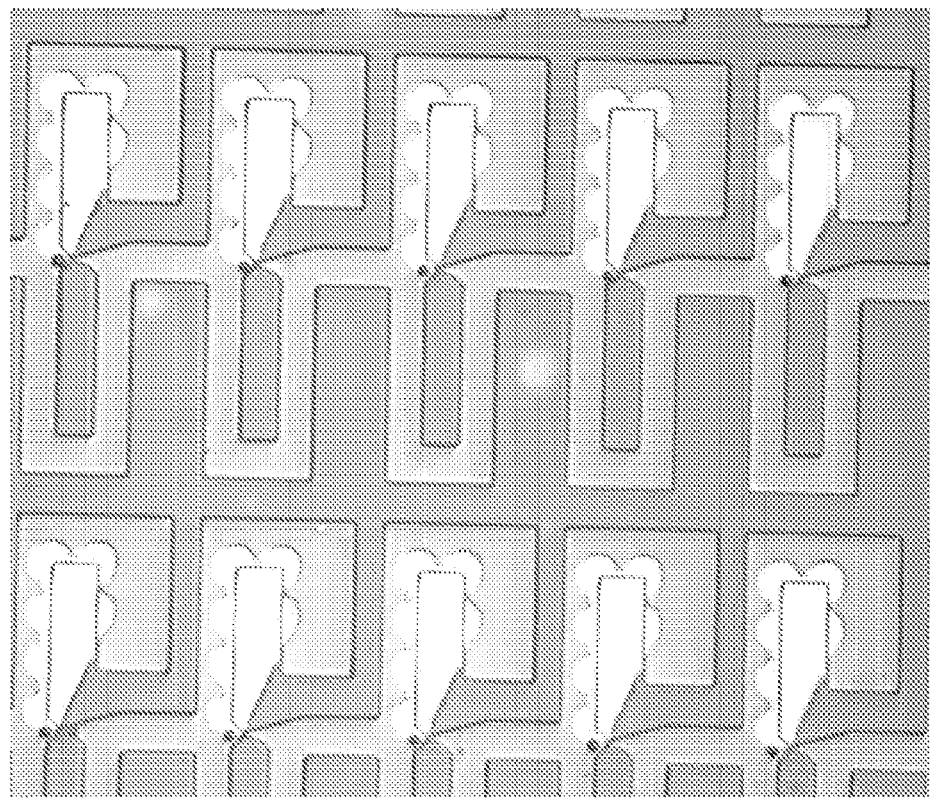
FIG. 32a-d shows (a) multiple beads trapped in individual fluidic traps, and (b) and (c) traveling along respective tracks, and arriving into individual partitions in (d).
Figure 32B:
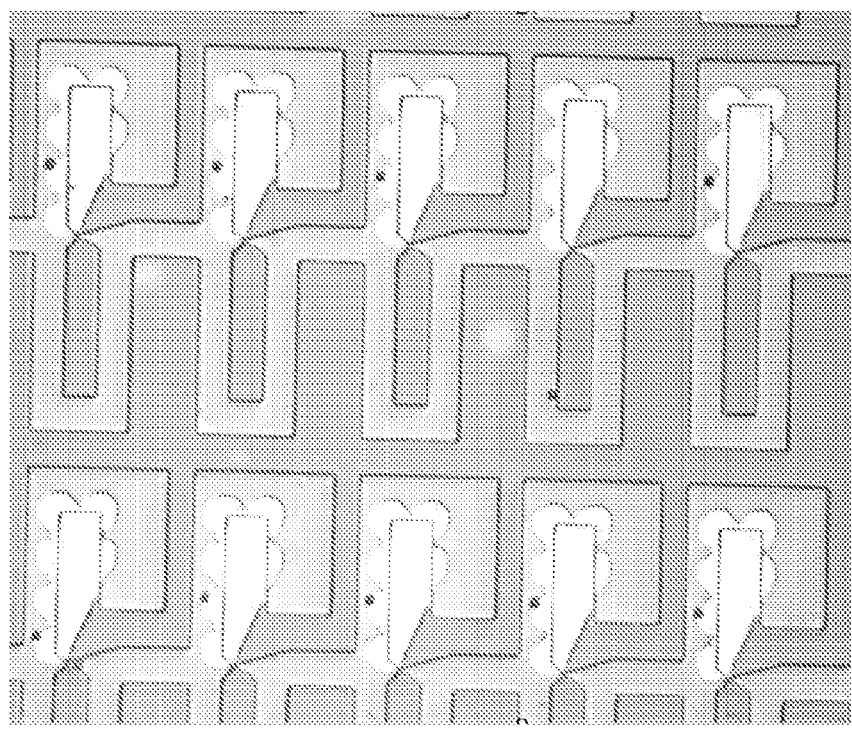
Figure 32C:
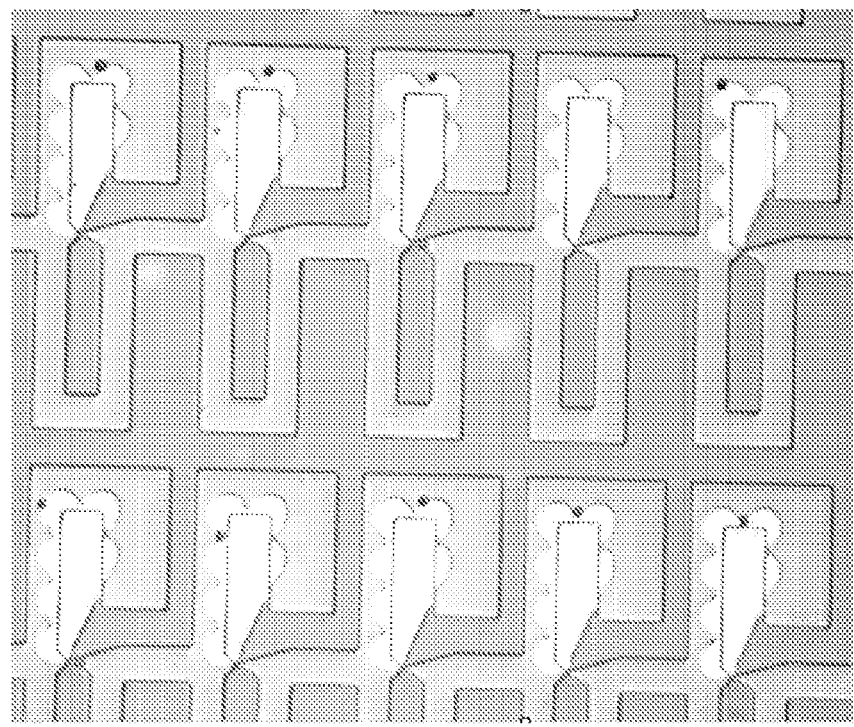
Figure 32D:
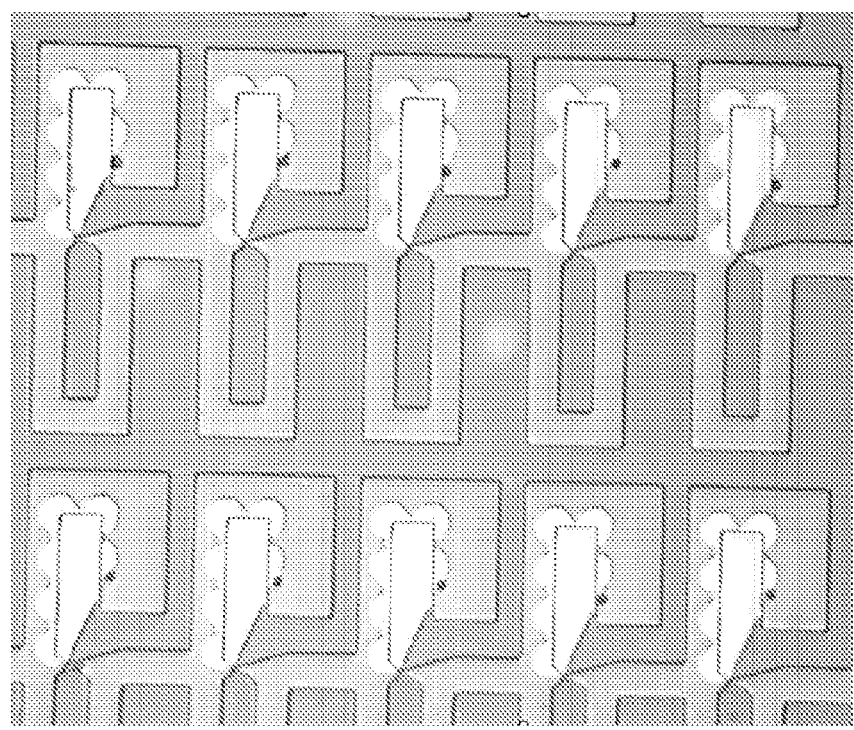

Shown in FIG. 15, is an array of partitions fluidically connected by a path 1502, each partition 1501 of which has a trap 1503 adjacent thereto. In FIG. 15, each of the traps is populated with a single cell. The single cell or another object that is trapped, such as a bead, may be transferred into the adjacent partition employing a magnetic track 1504. FIG. 32a-d shows individual images of a time lapse moving showing a series of magnetic beads trapped in a trap (FIG. 32a), the beads of which may be transferred into the adjacent partition as shown in FIG. 32b-d. FIG. 18 shows an alternative embodiment having a path 1802, a trap 1803, and a partition 1801 adjacent thereto the trap. FIG. 19 shows an alternative embodiment having a path 1902, a trap 1903, and a partition 1901 adjacent thereto the trap. FIG. 21 shows an alternative embodiment having a path 2102, a trap 2103, and a partition 2101 adjacent thereto the trap.

Figure 22:
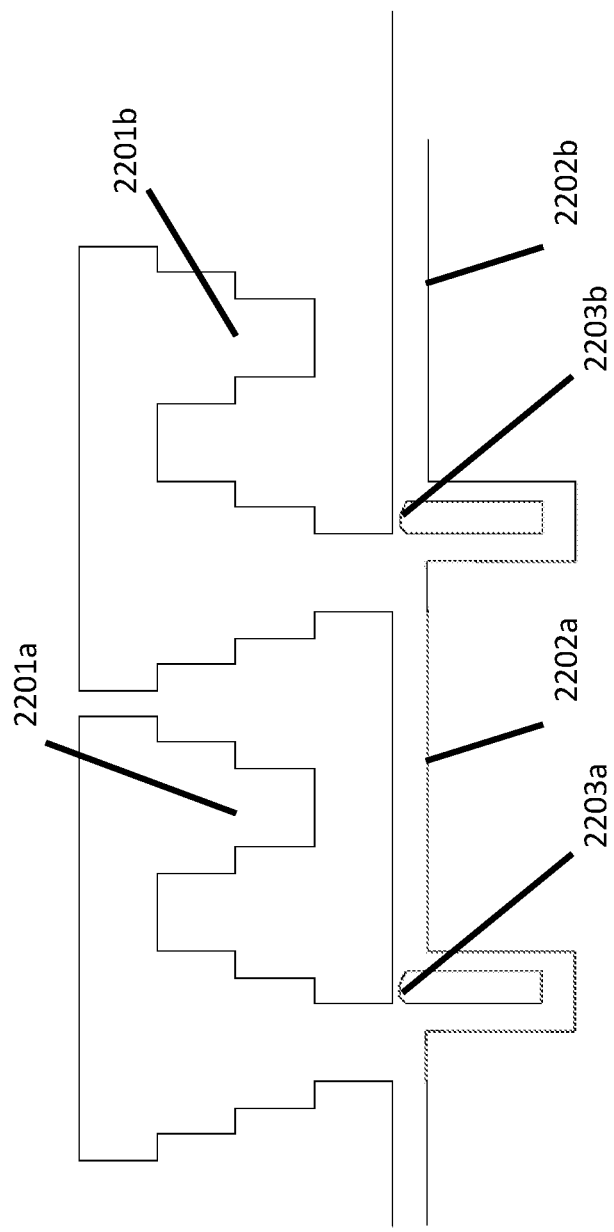
FIG. 22 shows an example of two apartments and adjacent traps in series fluidically connected by a path.
Figure 23:
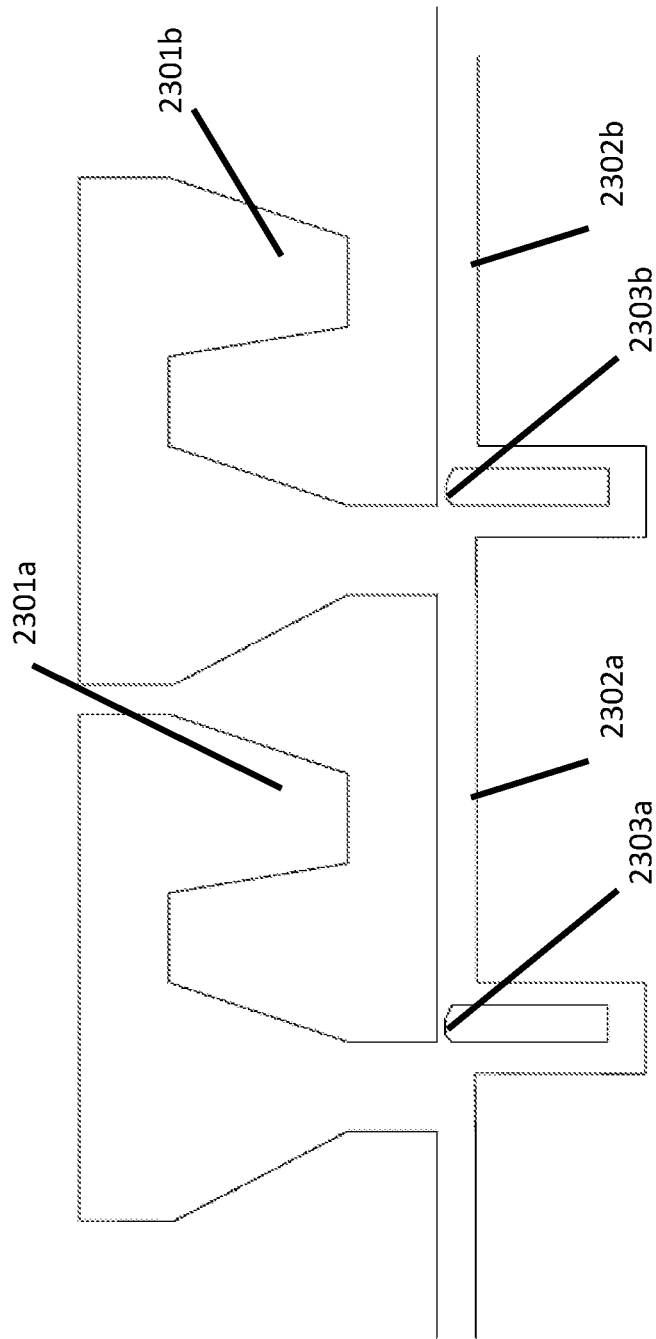
FIG. 23 shows an example of two apartments and adjacent traps in series fluidically connected by a path.

FIG. 22 and FIG. 23 show an alternative embodiment in which a shape of a partition may be optimized for acoustic transfer of an object into and within a partition. FIG. 22 shows a path (2202a-b), a trap (2203a-b), and a tiered partition of segmented and reduced widths (2201a-b). FIG. 23 shows a path (2302a-b), a trap (2303a-b), and a gradually narrowed width of a partition (2301a-b). The change in shape of the partition may permit or optimize an acoustic transfer of an object into a partition and/or acoustic transfer of an object to a different location within the partition.

Figure 31A:
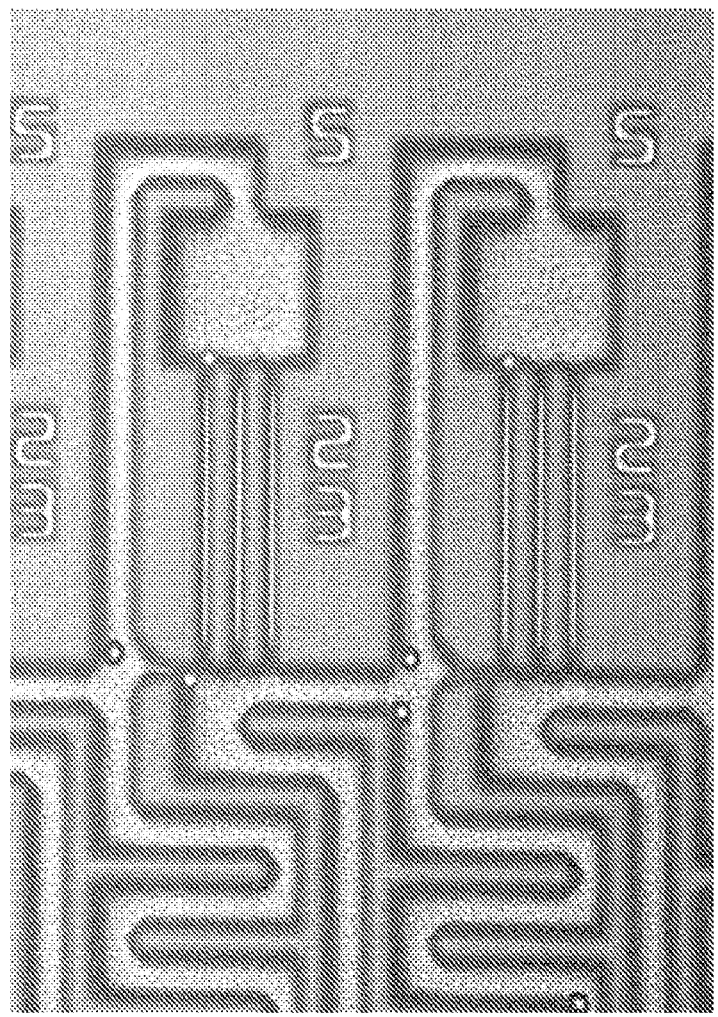
FIG. 31a-c shows still images of two objects being transferred into their respective partitions.
Figure 31B:
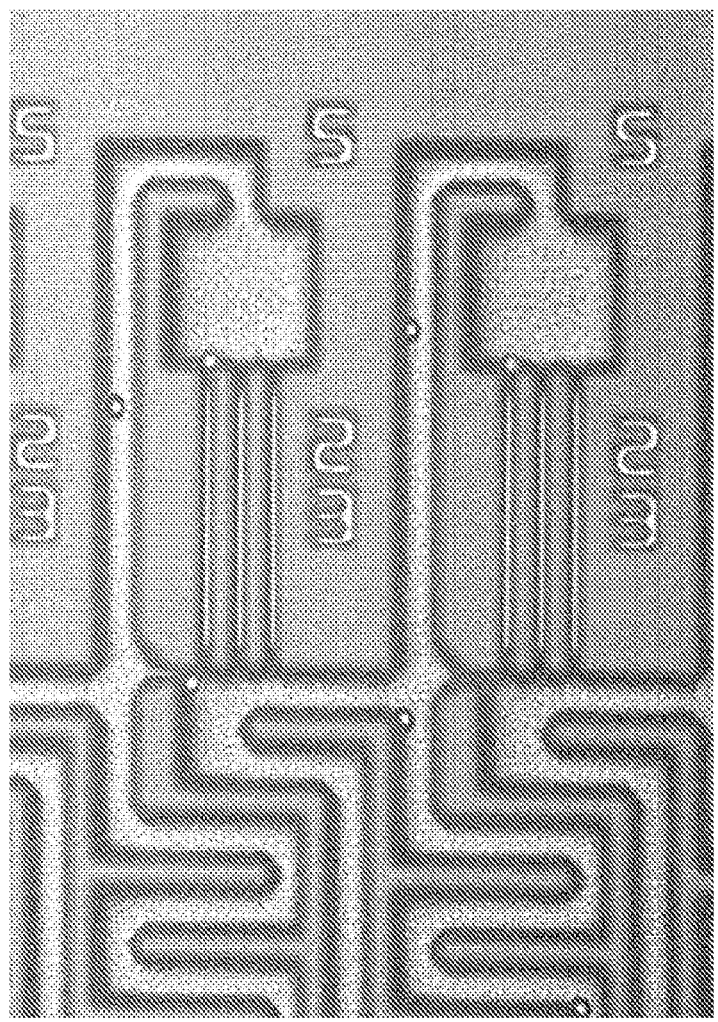
Figure 31C:
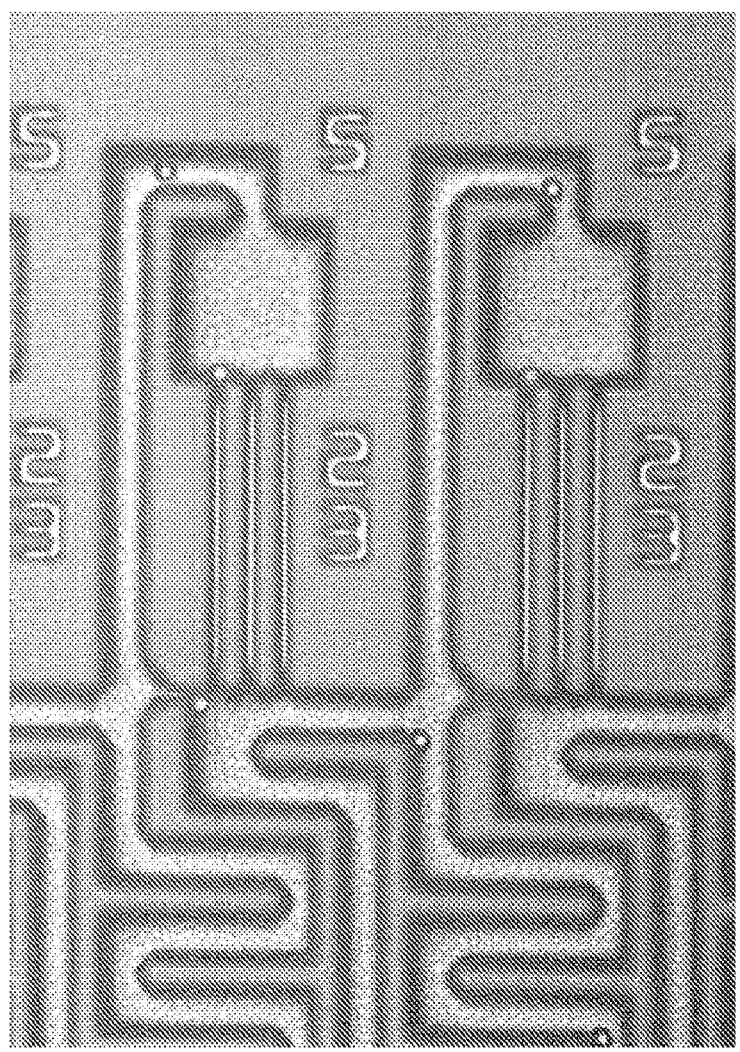

FIG. 31a-c shows a series of sequential still images showing an object, moving into a partition using an acoustic mechanism to transfer the object from the trap into the partition.

Figure 35:
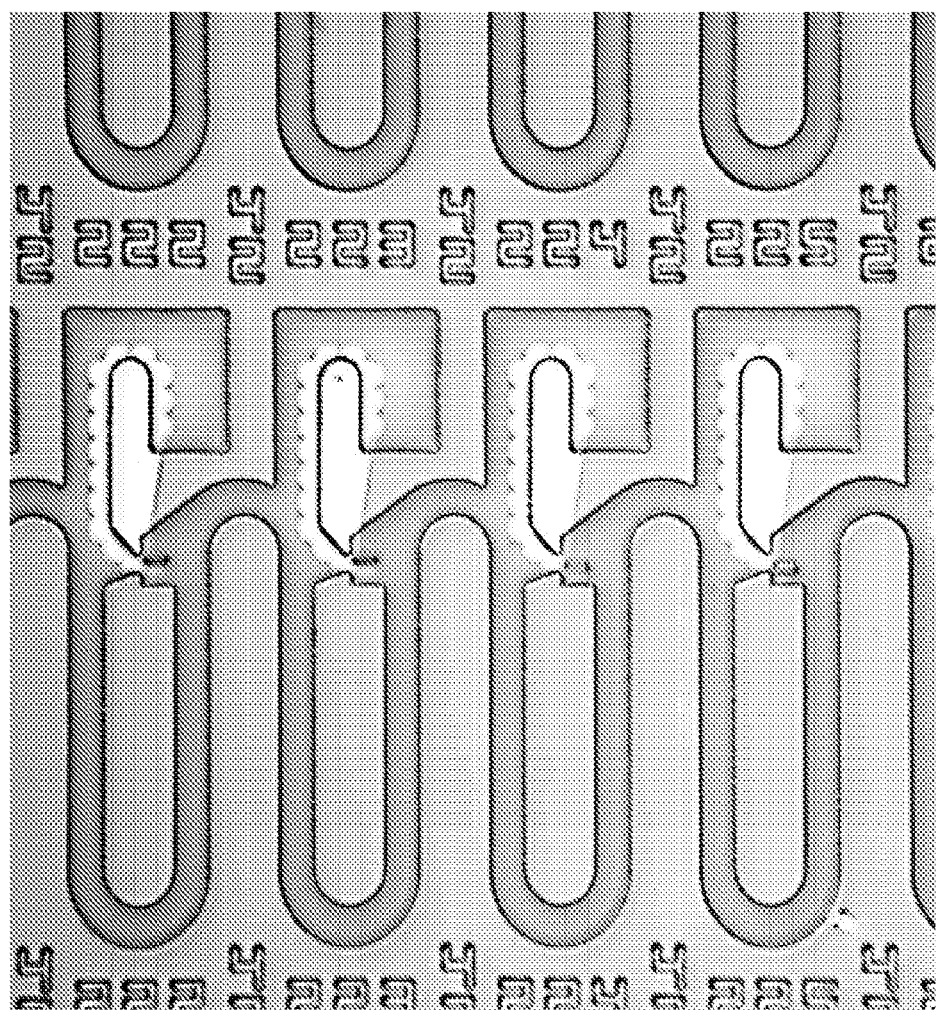
FIG. 35 shows a series of magnetic and fluidic traps.
Figure 36A:
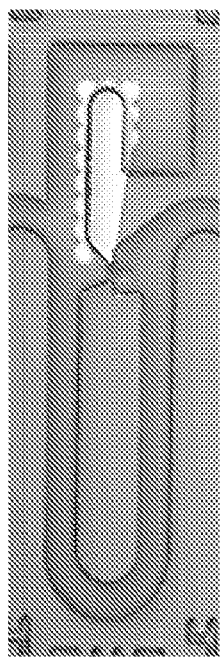
FIG. 36a-h shows shape variations of an individual magnetic and fluidic trapping unit, including the trap, partition, and path.
Figure 36B:
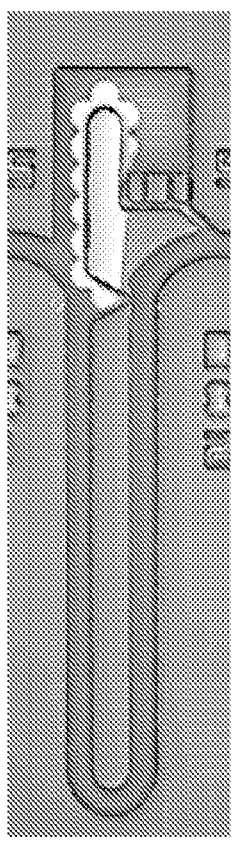
Figure 36C:
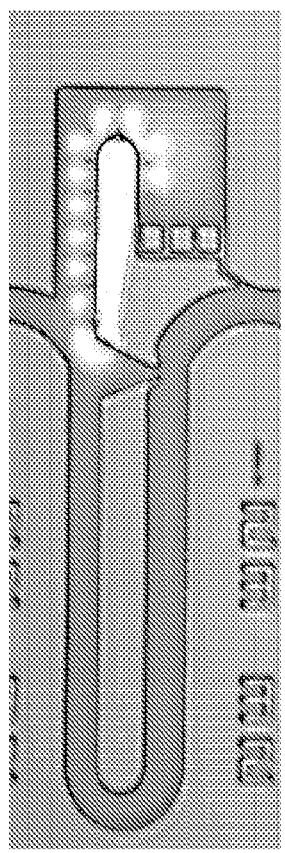
Figure 36D:
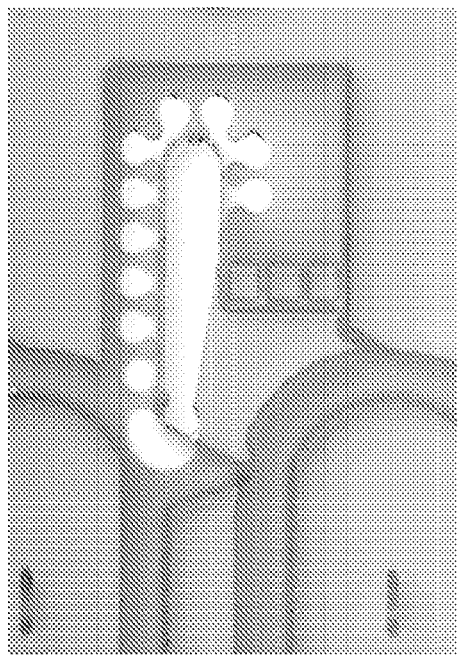
Figure 36E:
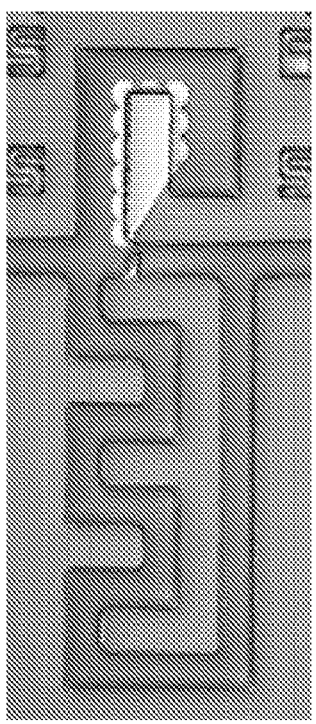
Figure 36F:
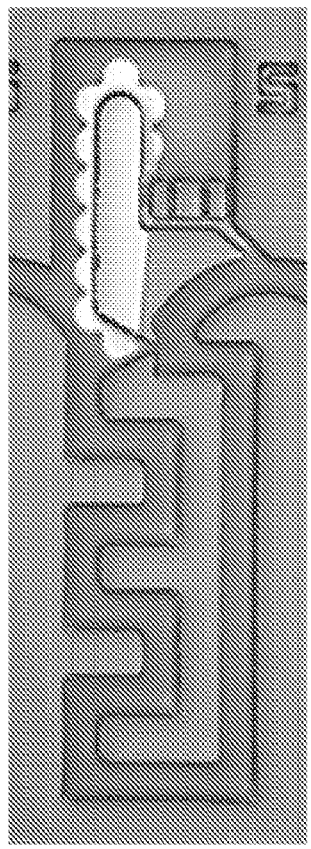
Figure 36G:
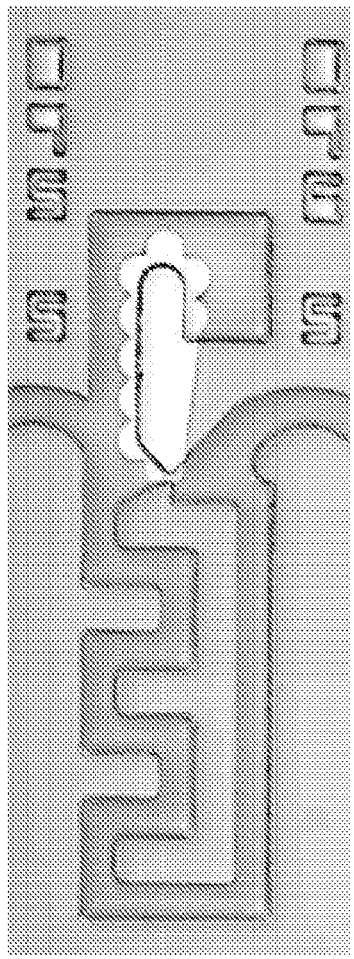
Figure 36H:
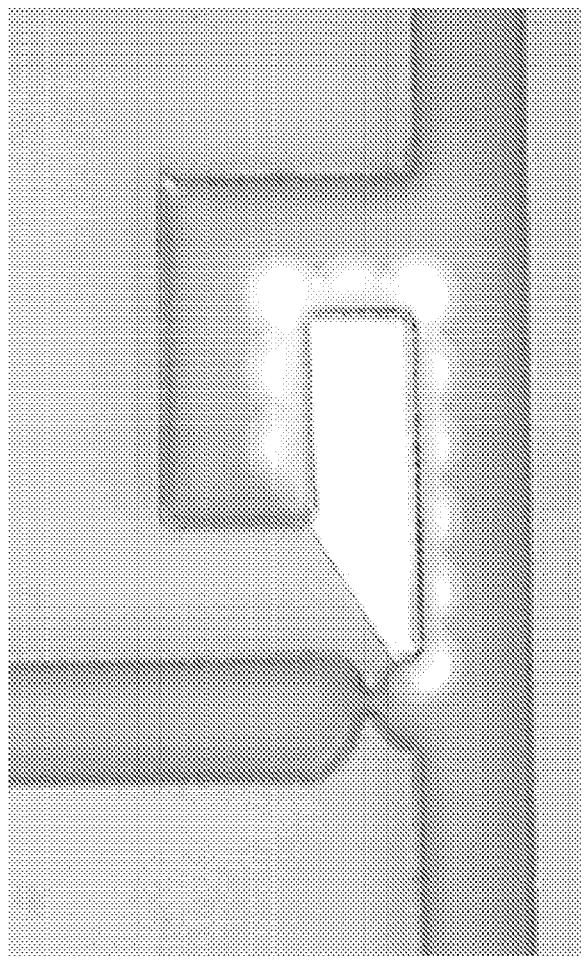
Figure 37A:
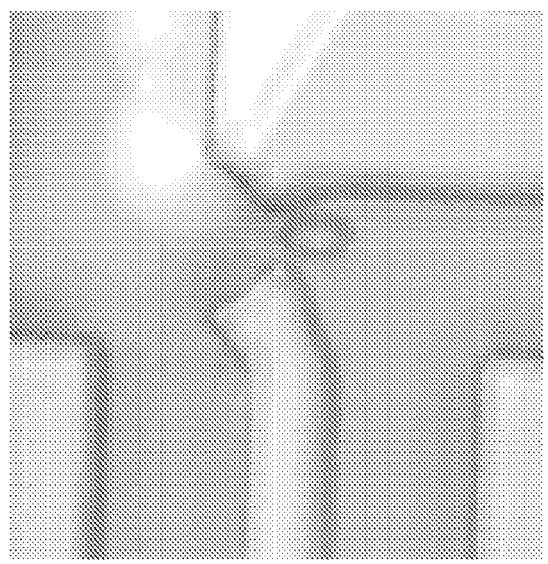
FIG. 37a-e shows shape variations of a magnetic and fluidic trap.
Figure 37B:
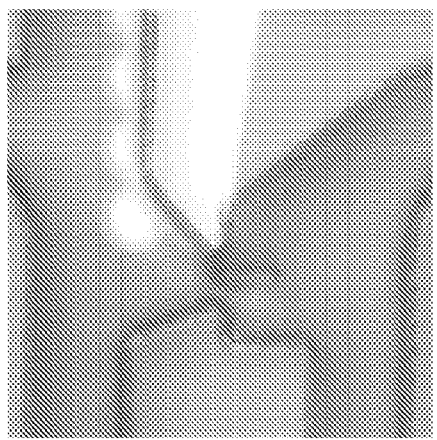
Figure 37C:
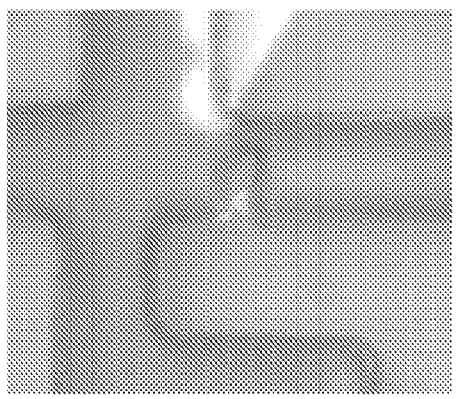
Figure 37D:
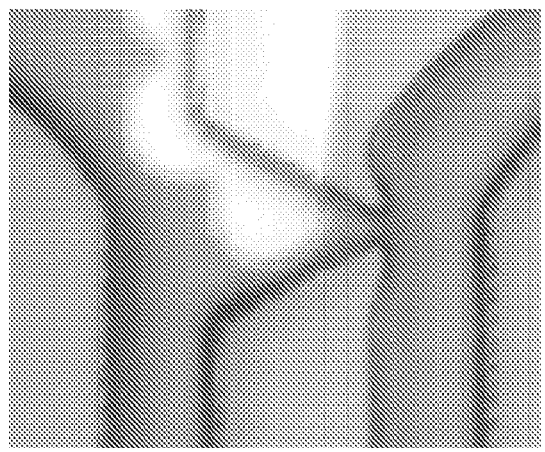
Figure 37E:
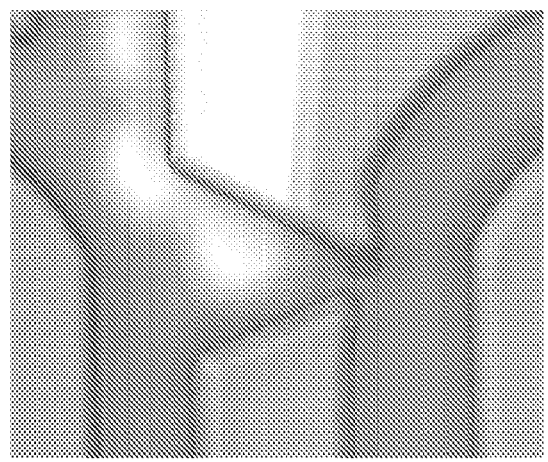

FIG. 35 shows a series of partitions with a hydrodynamic trap adjacent thereto each of the partitions with a magnetic track positions between each trap and adjacent partition. FIG. 36a-h show alternative embodiments for the shape of individual trap/partition/path units. The path may vary in shape. The track positioned between the trap and partition may vary in shape. The partition may vary in shape and may be fluidically connected to a portion of the path. The magnetic pattern may vary in shape. The trap may vary in shape as also shown in FIG. 37a-e.

Figure 38A:
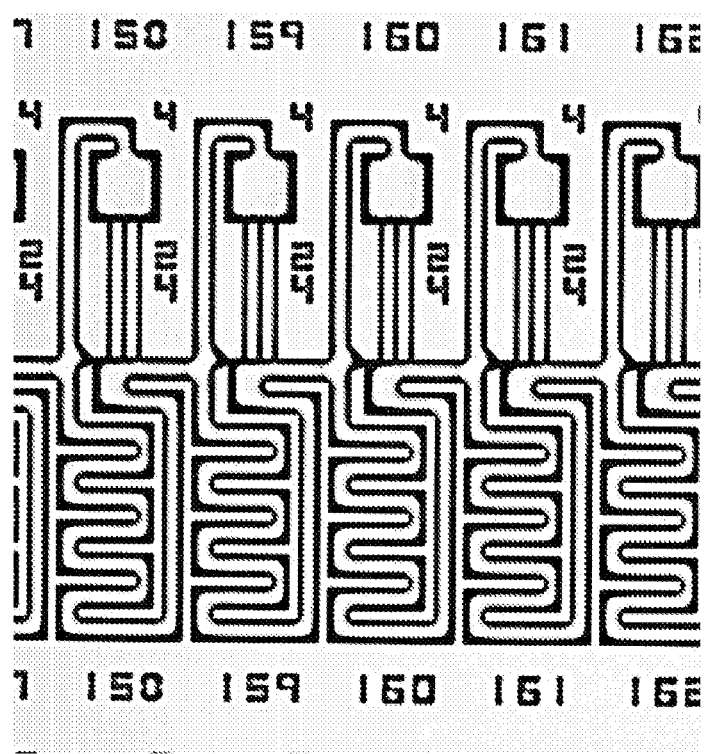
FIG. 38a-c shows an acoustic trapping array including the trap, partition, and path, with a close-up of the trap shown in (c).
Figure 38B:
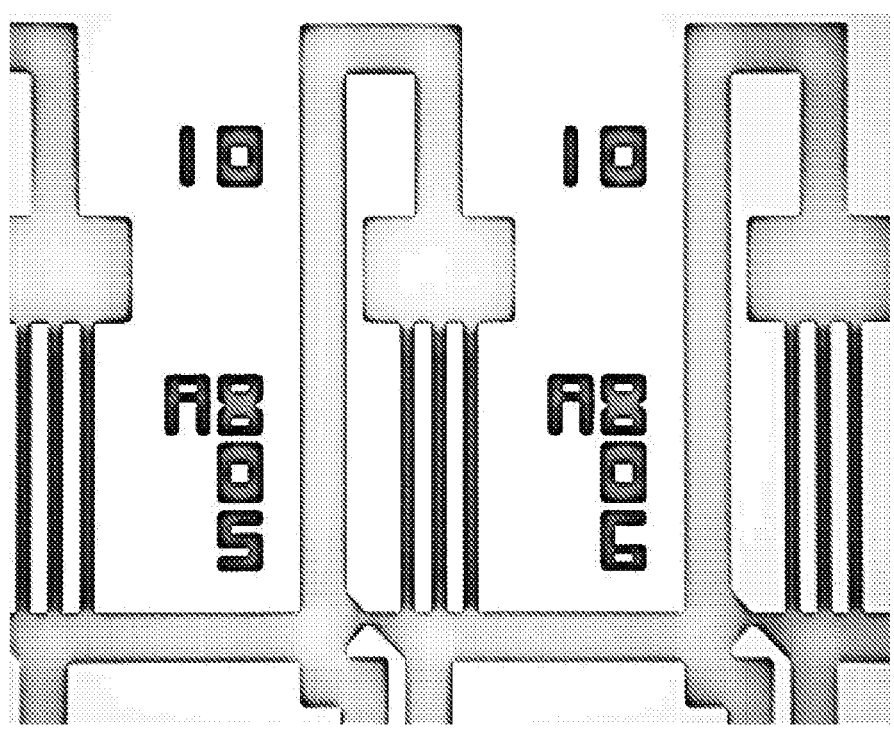
Figure 38C:
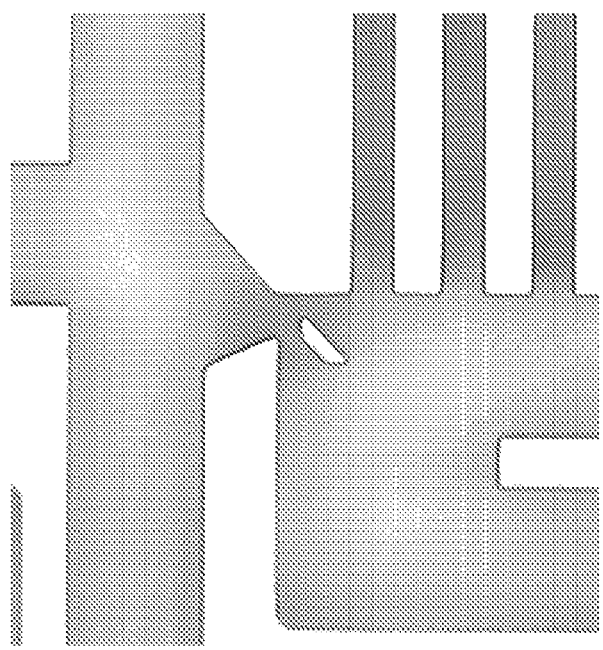

FIG. 38a and FIG. 38b shows a series of partitions with a trap adjacent thereto each of the partitions in which an object is moved between the trap and adjacent partition by an acoustic tuning. A close up of the trap is shown in FIG. 38c. The partition may be fluidically connected to the path.

Figure 39:
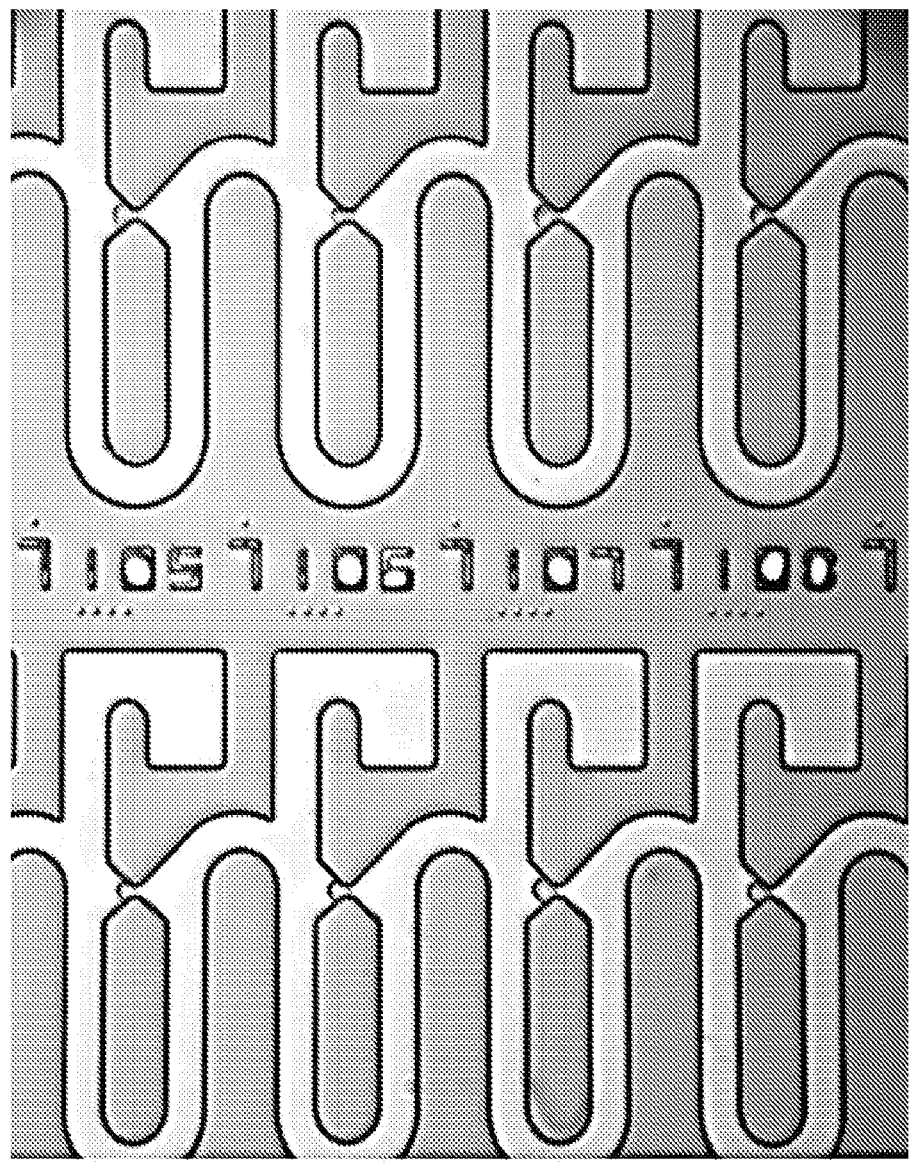
FIG. 39 shows a series of cell trapped in a series of fluidic traps.

FIG. 39 shows an alternative embodiment of individual cells trapped in a series of traps. Each trap having a partition adjacent thereto.

Figure 25:
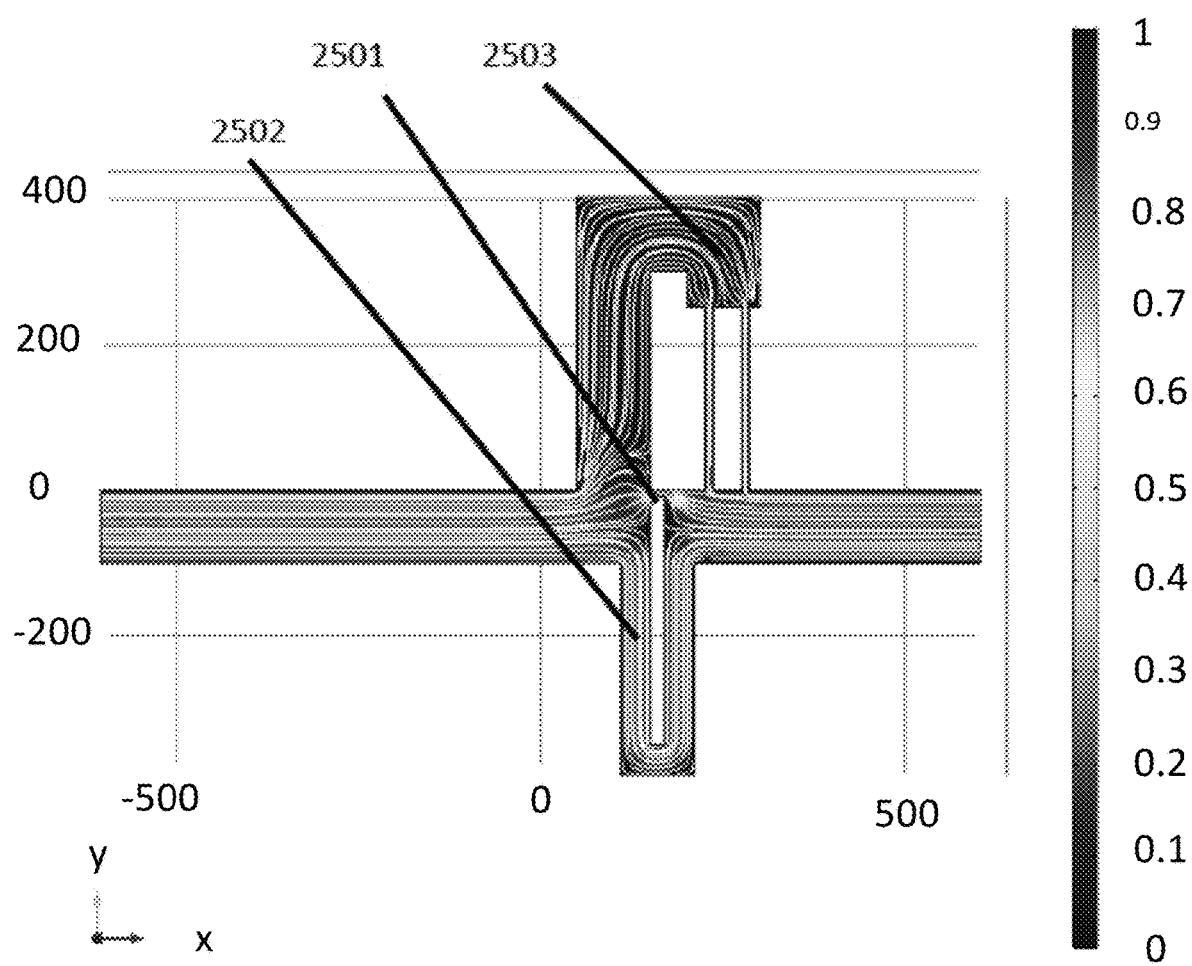

Shown in FIG. 25, is a microfluidic channel allowing fluid to flow through three distinct paths. The path of lowest resistance may be through the hydrodynamic trap region (2501), which has the highest volumetric flow rate, $Q_1$. The path of second lowest resistance is around the bypass channel (below the trap, 2502), and has the second highest volumetric flow rate, $Q_2$. The path of highest resistance is through the partition (above the trap, 2503) and has the lowest volumetric flow rate, $Q_3$. The conditions are designed such that $Q_1 > Q_2 \gg Q_3$ which is chosen so that the cell/bead may be captured first by the hydrodynamic trap. Once the trap is occupied with a single cell/bead, the next most likely path may be through the bypass channel (below, 2502). The fluidic network may be designed such that virtually no cells/beads will move into the partition based on hydrodynamic forces alone.

Figure 26:
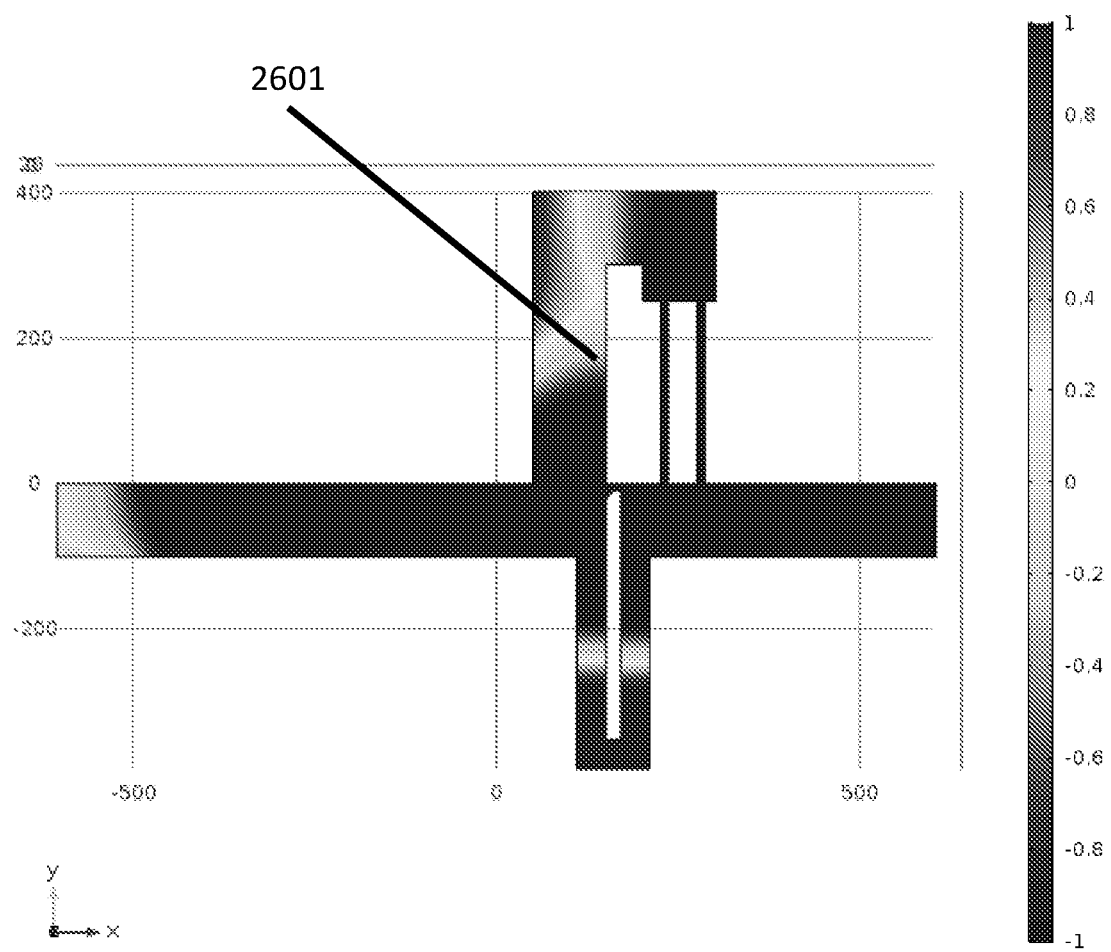

Once the cells are trapped, the fluid flow may be turned off, at which point it may be possible to move the cell/bead a short distance into the partition by an acoustic mechanism or magnetic mechanism, etc., past the location depicted in FIG. 26 by the 2601. If the cell/bead makes it past this location, then it may be carried into the interior of the partition once the fluid flow is re-established. This can be achieved by turning on an acoustic field, which may create a standing wave and push the cell/bead into the anti-node, which is halfway into the partition. Or it can be achieved with magnetic tracks. The purpose of this flow trifurcation may be to allow the fluid to carry the cells/beads into the interior of the traps, and may help prevent them from sticking on the walls of the partition, especially when the partition has a long entry way as shown.

A fluid flow may split into a parallel network of three flow streams with flow rates, $Q_1$, $Q_2$, and $Q_3$, as shown in FIG. 27a. Due to continuity of mass, the fluid flows are related as:

$$Q_{in} = Q_1 + Q_2 + Q_3$$

For laminar fluid flow, the relationship between flow rate and pressure drop is given by:

$$\Delta P = P_{in} - P_{out} = Q_{in} R_{eq} = Q_1 R_1 \pm Q_2 R_2 + Q_3 R_3$$

where the hydrodynamic resistances of each flow stream are given by $R_1$, $R_2$, and $R_3$, respectively. The first flow resistor may correspond to the fluid trap, $R_1$, may exist in either a high resistance state when the trap may be occupied by an object, or a low resistance state when the trap may be unoccupied. The second resistor may correspond to the bypass channel, $R_2$, and may remain constant in time. The third resistor may correspond to flow through the partition, and may be adjusted to have the largest resistance in order to produce the weakest flow rate and thereby prevent objects from being unintentionally transferred into the partition without an external non-fluidic force. All channels may have the same heights, h, but have different widths, $w_1$ (2701), $w_2$ (2702), and $w_3$, and different lengths $L_1$, $L_2$, and $L_3$, as shown in FIG. 27b.

As one specific example, a microfluidic channel may have height, h=20 μm, and the width of the trapping region is $w_1$=3 μm, which is small enough to capture a single cell in the fluid trap. The bypass channel may have a width $w_2$=20 μm to allow unimpeded flow of the cells to the next fluid trap. Optimizing the trap to be efficient at capturing single cells may require that:

$$\frac{R_2}{R_1} \gg 1$$

Using the expression for flow resistance through a rectangular pipe, this ratio is $$\frac{R_2}{R_1} = \left(\frac{L_2}{L_1}\right)\left(\frac{w_1}{w_2}\right)^3\left(\frac{h_1}{h_2}\right)\frac{(1-0.63w_1/h_1)}{(1-0.63w_2/h_2)} \gg 1$$

in which the channel width may be assumed to be the smallest dimension. Assuming the geometric constraints of the above example, this ratio is:

$$\frac{R_2}{R_1} \approx \frac{L_2}{120L_1} \gg 1$$

which may indicate that in order to become efficient at capturing single objects, the fluid bypass channel may ideally be several hundred times longer than the length of the fluid trap. A typical example may be designed such that the length of the bypass channel would be around $L_2$=500-1000 μm, whereas the fluid trap may have a length of $L_1$=3 μm or smaller. The equivalent flow resistance through the single fluid trap may be on the order of:

$$R_{eq} \approx 10^{13} - 10^{14} \frac{Ns}{m^5}$$

An N×M array of these trapping elements may be constructed by arranging each row with N elements connected in series, and then arranging M of these rows connected in parallel. The equivalent hydrodynamic resistance of the entire array may be:

$$R_{array} = R_{eq}\left(\frac{N}{M}\right)$$

So long as non-fluidic forces are absent, the cells may not enter the partition. However, if the cells are moved by a non-fluidic force to a position past the stagnation point, then the cells may be carried by the flow rate $Q_3$ into the interior of the partition and trapped within. The two step transfer approach therefore may involve first capturing the cells in the fluidic traps, and then using an additional force to transfer the cells past the stagnation point to a location where fluid flow may move them to their final destination within the interior of the partition.

Figure 28A:
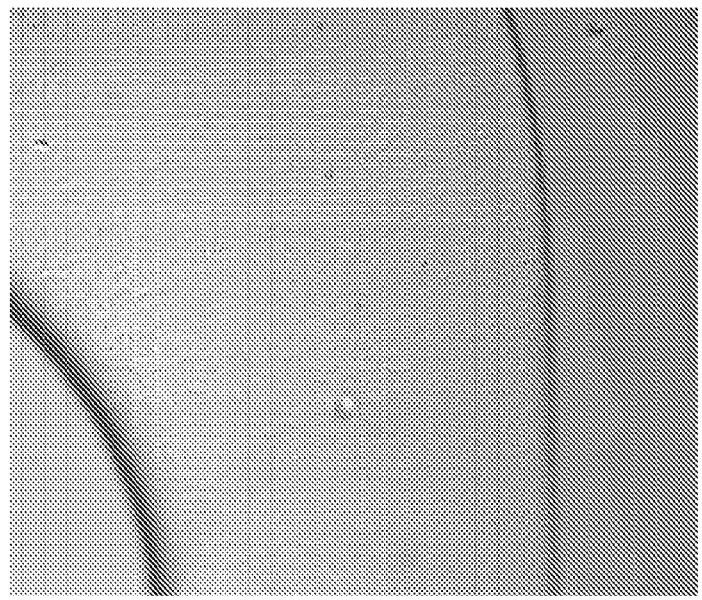
FIG. 28a-c shows a bead moving from one section of a partition in (a) to a different section in (b) and back to the same section in (c).
Figure 28B:
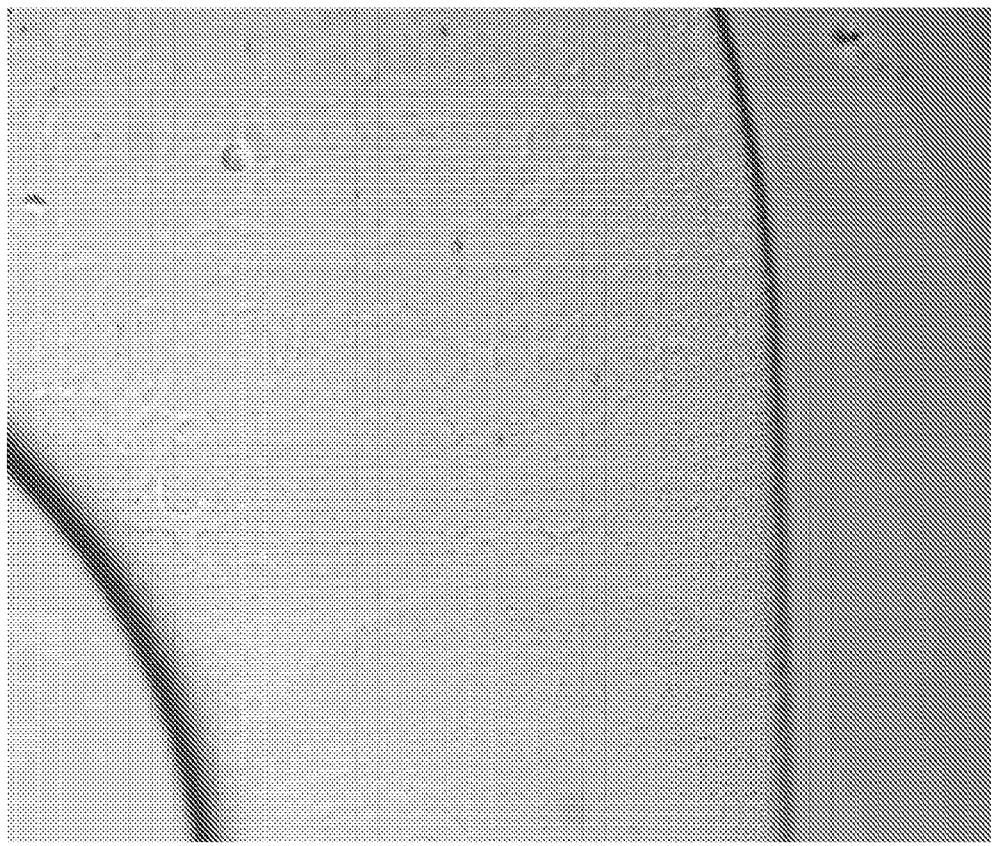
Figure 28C:
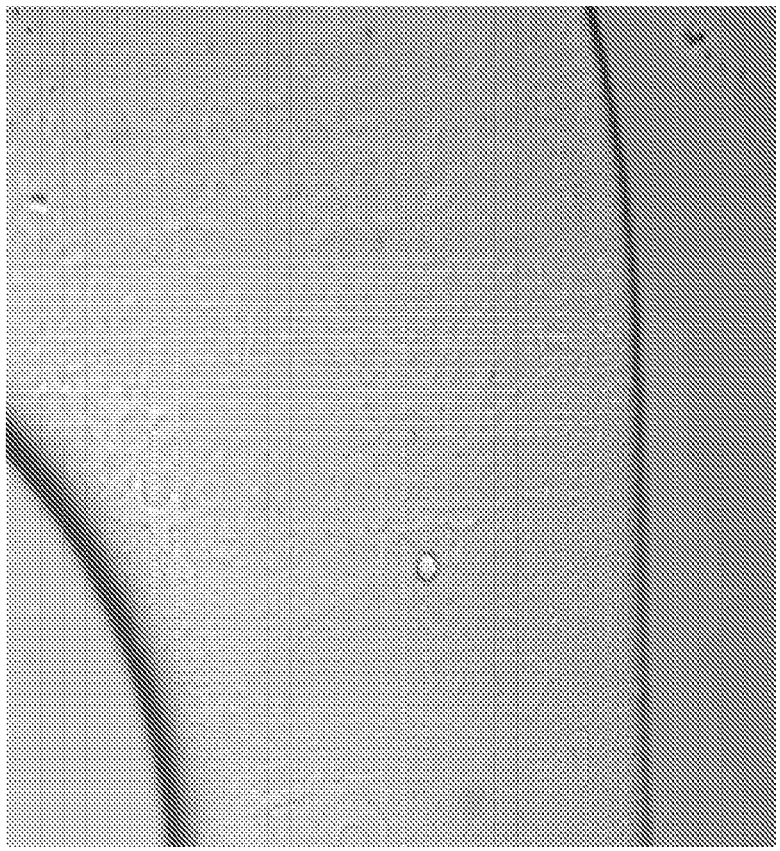
Figure 29A:
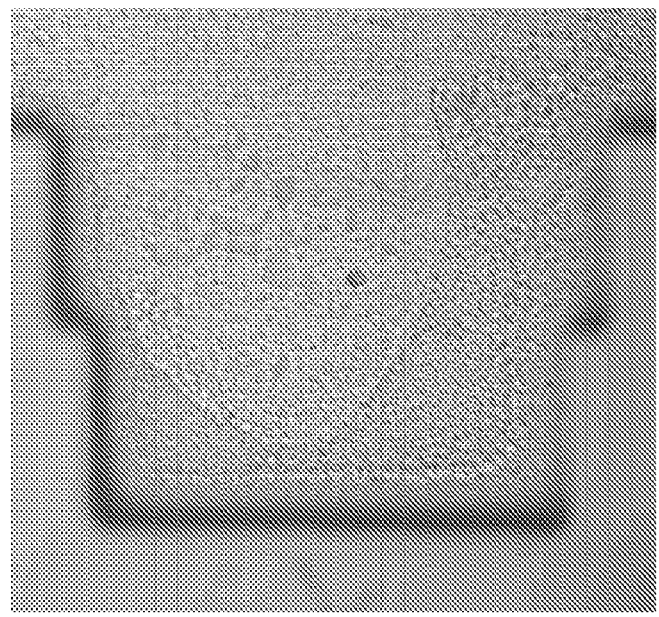
FIG. 29a-c shows a bead moving from one section of a partition in (a) to a different section in (b) and back to the same section in (c).
Figure 29B:
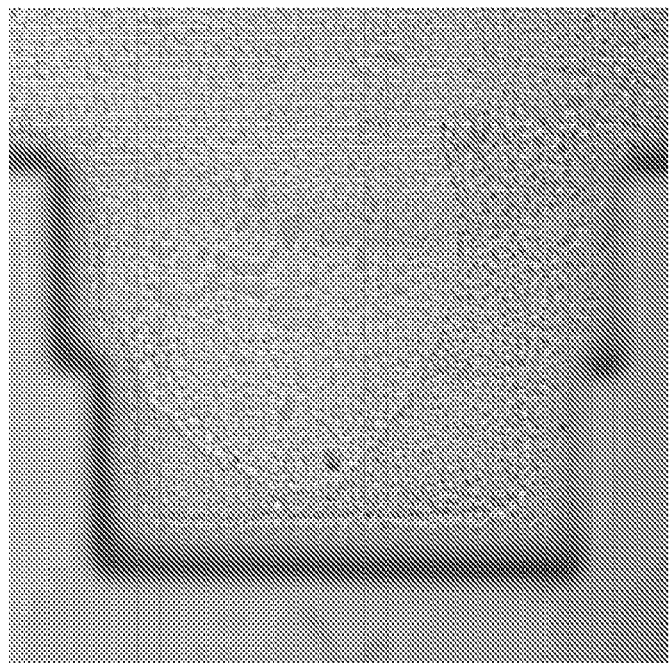
Figure 29C:
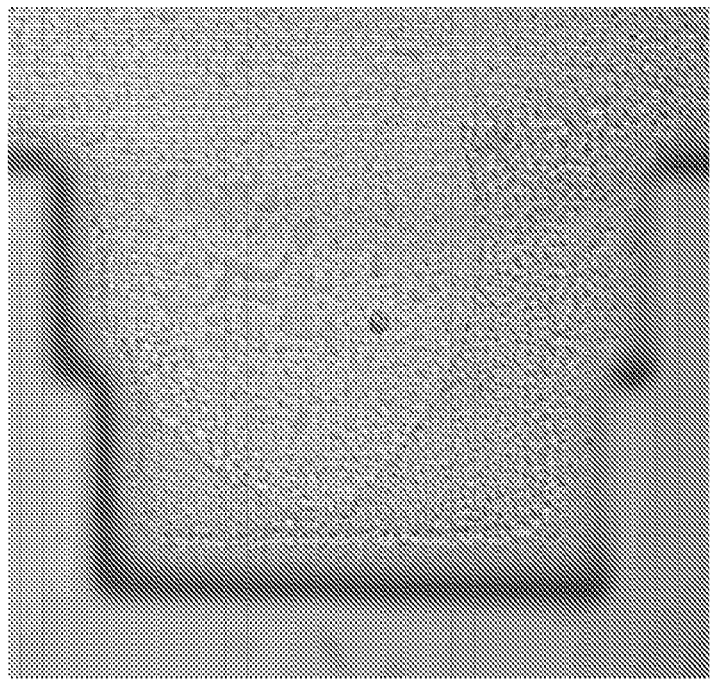

In some cases, an acoustic mechanism may transfer an object from a trap to an adjacent partition or move an object within a partition. Local resonances in an acoustic chamber may be manipulated to move the object, such as cells or beads, between different nodes, as shown in FIG. 29a-c. A bead may be trapped in a lower position at 2.85 MHz (FIG. 29a), and moves to an upper position at 2.95 MHz (FIG. 29b) and moves back to the lower position at 2.85 MHz (FIG. 29c). An object may be transferred between two locations by switching between two different frequencies. Another example of moving an object between two different locations using an acoustic mechanism is shown in FIG. 28a-c.

Figure 40A:
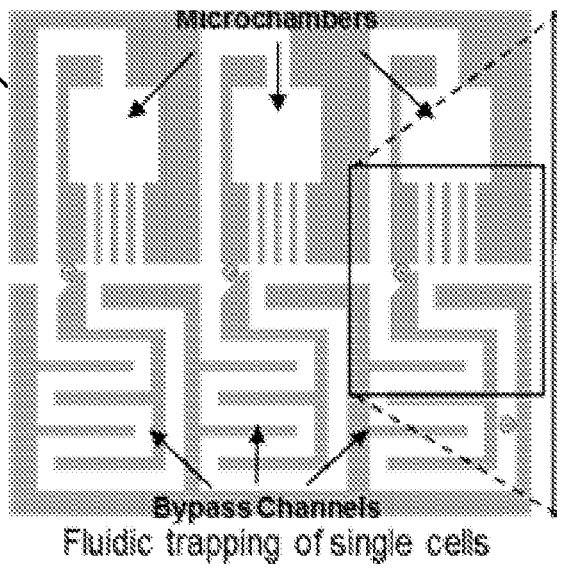
FIG. 40a-d shows capture of cells in fluidic traps and acoustic transfer into adjacent partitions.
Figure 40B:
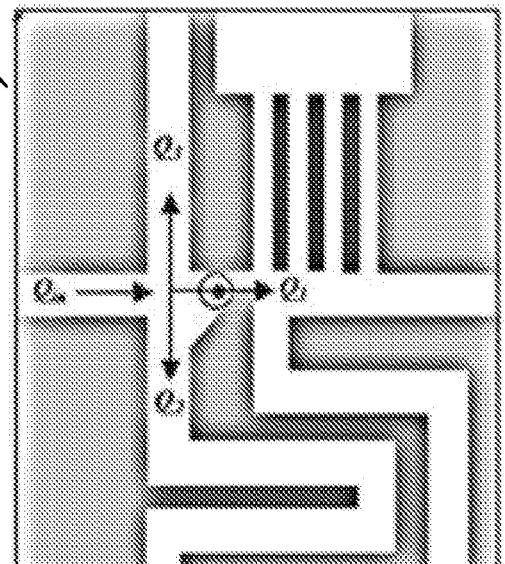
Figure 40C:
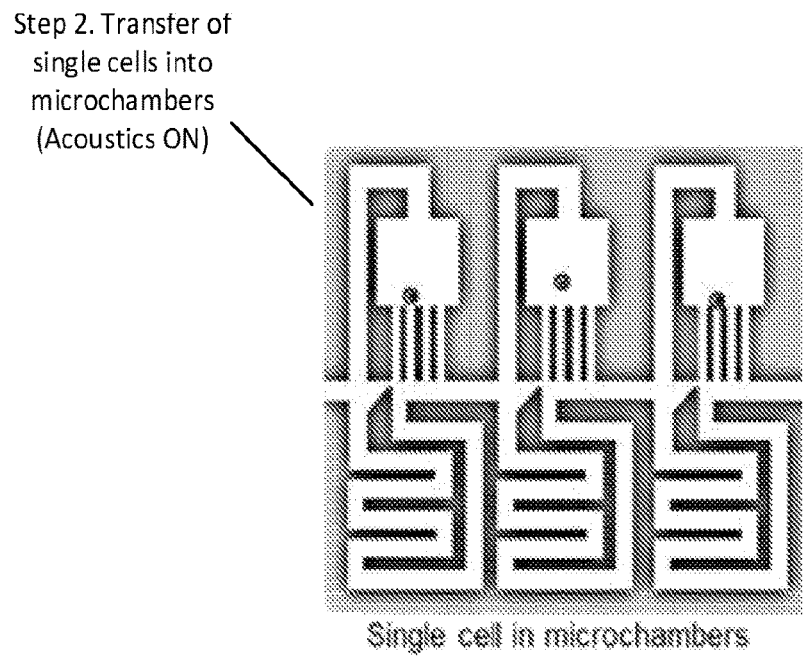
Figure 40D:
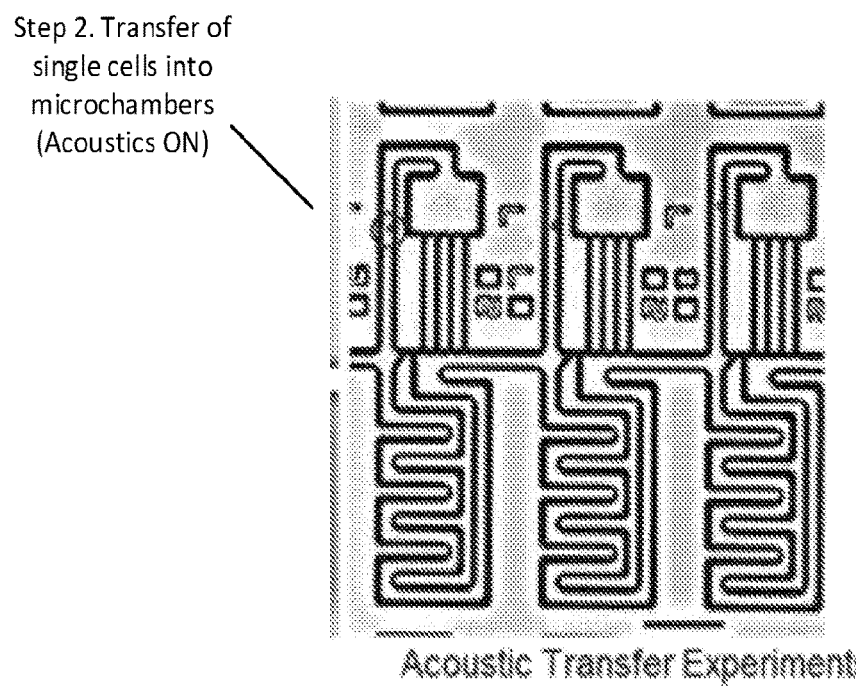

FIG. 40a-d shows an overview of an acoustofluidic trapping process. As shown in FIG. 40a, a cell may be captured in a fluidic trap. The trapping may occur by tuning the volumetric flow rates at a microfluidic trifurcation, as shown in FIG. 40b. The flow rates of each channel as show in FIG. 40b may be $Q_{in}=Q_1+Q_2+Q_3$. The highest flow rate may be $Q_1$, through the fluid trap, which may capture the cell. Once a cell may occupy the trap, remaining cells may move through a bypass channel. The bypass channel may have a second highest flow rate, $Q_2$. The fluidic structure may be designed such that the path into the partition may have the lowest flow rate $Q_3$. In this case, no cell may be moved into an adjacent partition when the acoustics are turned off or not activated. When an acoustic wave is activated or turned on, the acoustic wave may be employed to transfer a cell into an adjacent partition, such as transfer a cell into an adjacent partition with high efficiency, as shown in FIG. 40c. An experimental demonstration of cells moved into adjacent partitions is shown in FIG. 40d, where one cell is circled. The scale bar=100 um. A plurality of partitions may have a single object occupancy from a single transfer. In some cases, about 75% of the plurality of partitions may have single object occupancy from a single transfer. For example, each object of a plurality of objects may be collectively transferred into an adjacent partition such that about 75% of the partitions of a plurality of partitions are occupied after the transfer. In some cases, about 60% of the plurality of partitions may have single object occupancy from a single transfer. In some cases, about 65% of the plurality of partitions may have single object occupancy from a single transfer. In some cases, about 70% of the plurality of partitions may have single object occupancy from a single transfer. In some cases, about 75% of the plurality of partitions may have single object occupancy from a single transfer. In some cases, about 80% of the plurality of partitions may have single object occupancy from a single transfer. In some cases, about 85% of the plurality of partitions may have single object occupancy from a single transfer. In some cases, about 90% of the plurality of partitions may have single object occupancy from a single transfer. In some cases, at least about 60% of the plurality of partitions may have single object occupancy from a single transfer. In some cases, at least about 65% of the plurality of partitions may have single object occupancy from a single transfer. In some cases, at least about 70% of the plurality of partitions may have single object occupancy from a single transfer. In some cases, at least about 75% of the plurality of partitions may have single object occupancy from a single transfer. In some cases, at least about 80% of the plurality of partitions may have single object occupancy from a single transfer. In some cases, at least about 85% of the plurality of partitions may have single object occupancy from a single transfer. In some cases, at least about 90% of the plurality of partitions may have single object occupancy from a single transfer.

When a stimulus from an acoustic source is applied to a partition, a frequency of the acoustic source may be constant, may be variable or adjustable such as by a user or a controller of a system. In some cases, a frequency of an acoustic source may be about: 1.00, 1.25, 1.50, 1.75, 2.00, 2.25, 2.50, 2.75, 2.80, 2.85, 2.90, 2.95, 3.00, 3.05, 3.10, 3.25, or 3.5 MHz. In some cases, a frequency of an acoustic source may be about 1.00 MHz. In some cases, a frequency of an acoustic source may be about 1.25 MHz. In some cases, a frequency of an acoustic source may be about 1.50 MHz. In some cases, a frequency of an acoustic source may be about 1.75 MHz. In some cases, a frequency of an acoustic source may be about 2.00 MHz. In some cases, a frequency of an acoustic source may be about 2.25 MHz. In some cases, a frequency of an acoustic source may be about 2.50 MHz. In some cases, a frequency of an acoustic source may be about 2.75 MHz. In some cases, a frequency of an acoustic source may be about 2.80 MHz. In some cases, a frequency of an acoustic source may be about 2.85 MHz. In some cases, a frequency of an acoustic source may be about 2.90 MHz. In some cases, a frequency of an acoustic source may be about 3.00 MHz. In some cases, a frequency of an acoustic source may be about 3.05 MHz. In some cases, a frequency of an acoustic source may be about 3.10 MHz. In some cases, a frequency of an acoustic source may be about 3.15 MHz. In some cases, a frequency of an acoustic source may be from about 1.00 MHz to about 3.50 MHz. In some cases, a frequency of an acoustic source may be from about 2.50 MHz to about 3.25 MHz. In some cases, a frequency of an acoustic source may be from about 2.70 MHz to about 3.10 MHz.

Figure 43:
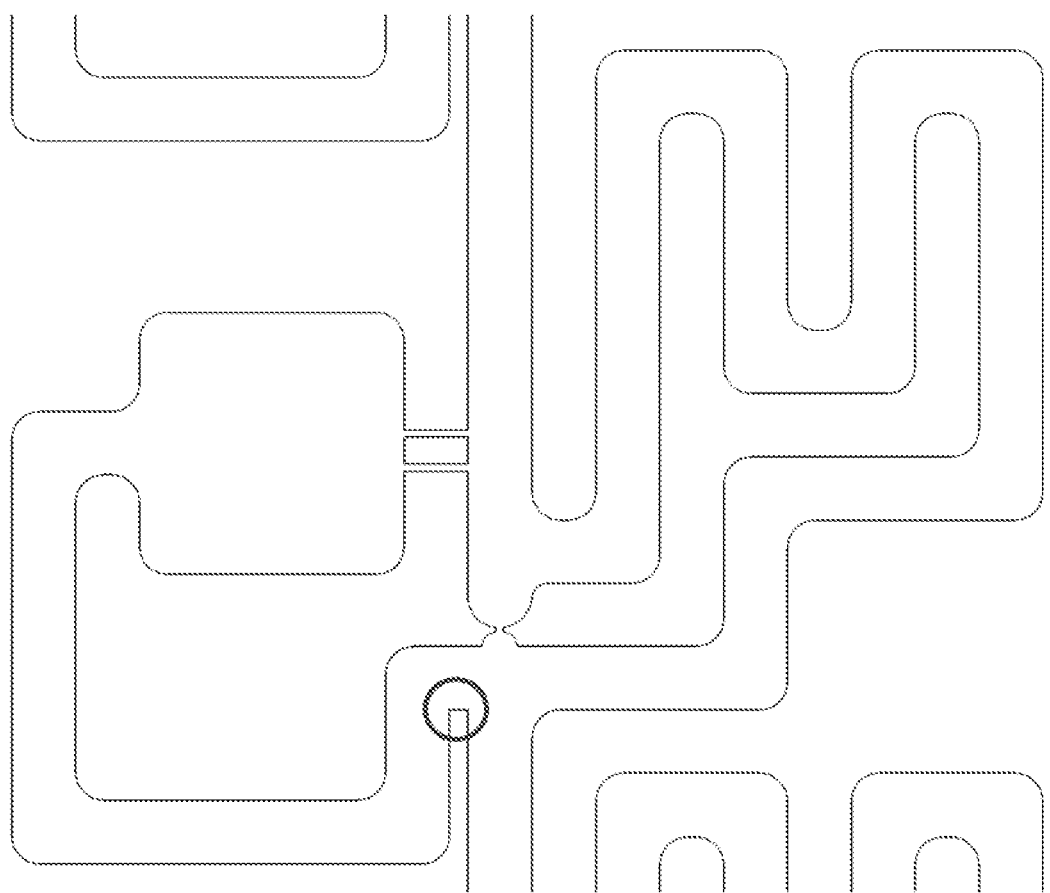
FIG. 43 shows a microfluidic channel design configured to use acoustic streaming to capture objects at the beam-like structure, which can then be transferred into the partition with a combination of acoustic signal and hydrodynamic flow.

FIG. 43 shows a microfluidic channel design. The structural element circled in FIG. 43 may be designed or modified to induce strong acoustic streaming near corners, such as sharp corners or beam-like structures, of the device. The induced fluid vortices (induced by this structural feature) may be employed to attract objects, such as cells, and may enable objects to be pushed into a flow stream that may be connected to a downstream partition.

Figure 44:
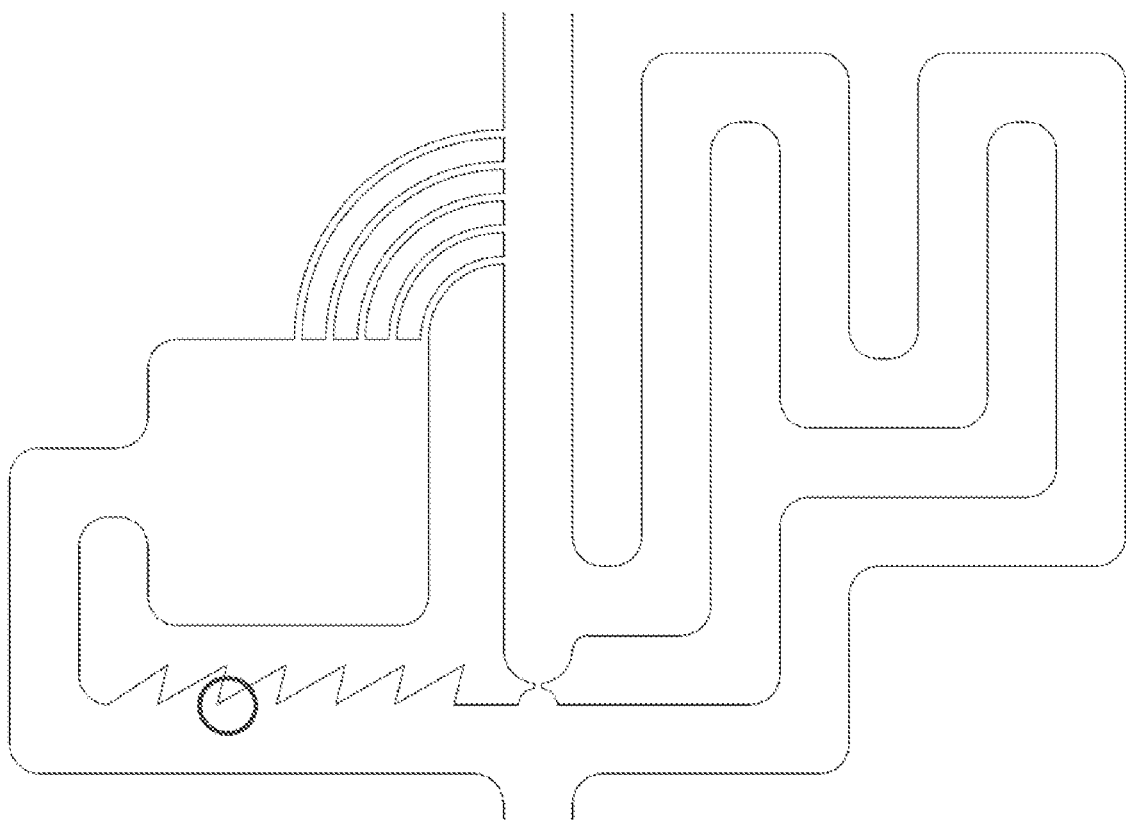
FIG. 44 shows a microfluidic channel design configured to use acoustic streaming to capture objects at sharp edges, which can then be transferred into the partition with a combination of acoustic signal and hydrodynamic flow.
Figure 45:
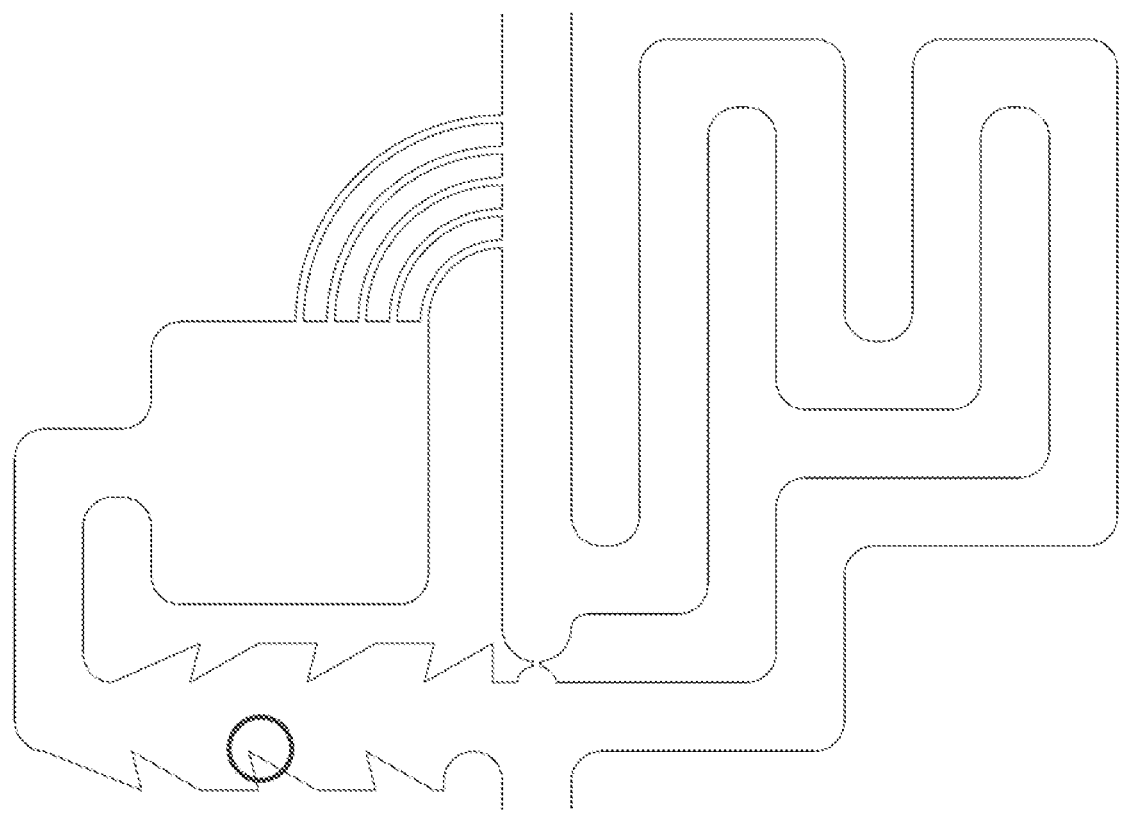
FIG. 45 shows a microfluidic channel design configured to induce bulk fluid flow into the partition based on acoustic streaming.

FIG. 44 shows a microfluidic channel design. The sharp edge circled in FIG. 44 may be a structural element designed or modified to induce steady state fluid flow, and thereby transfer objects, such as cells, into a flow stream connected to a downstream partition. FIG. 45 shows a microfluidic channel design. The edge, such as a sharp edge, circled in FIG. 45 may be a structural element designed or modified to induce steady state fluid flow, and thereby transfer objects into a flow stream connected to a downstream partition. Steady state fluid flow may be laminar flow or a fluid flow having fluid properties that do not change over time.

Figure 46:
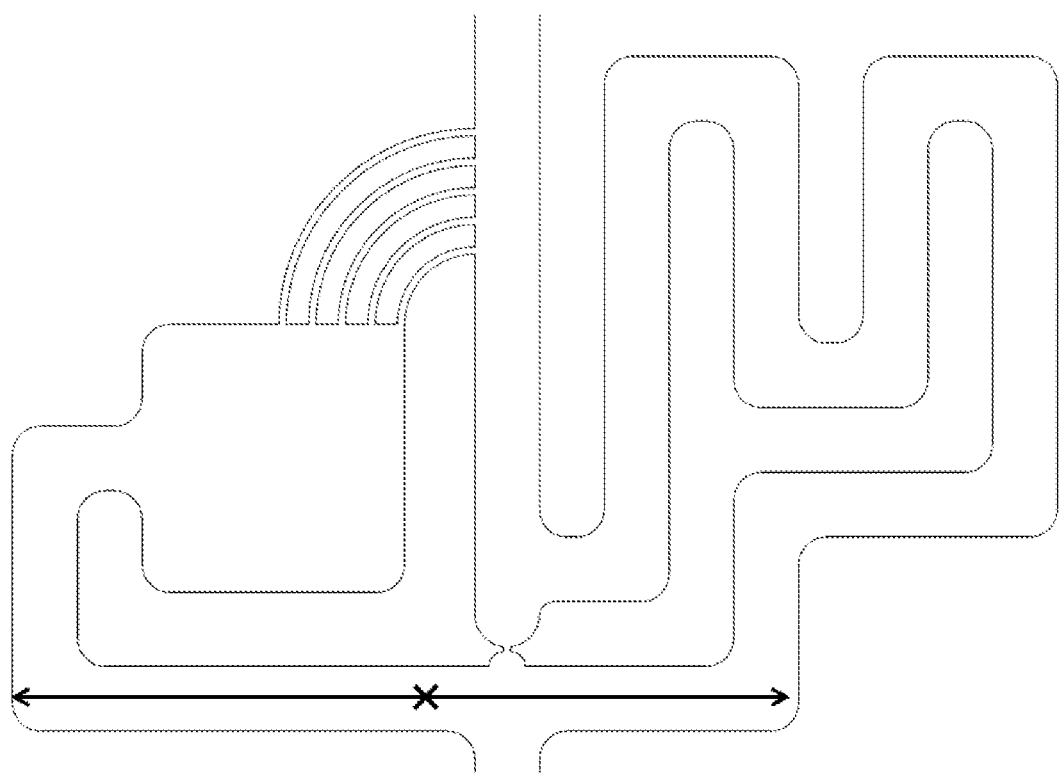
FIG. 46 shows a microfluidic channel design that may be used to establish an acoustic standing wave with a half wavelength that may be matched with the entrance to the partition (and depicted by the double arrow) and configured to transfer objects from the hydrodynamic trap towards the position denoted by the X, which can then be transferred into the partition with hydrodynamic flow.

FIG. 46 shows a microfluidic channel design. The arrow depicts a structural dimension which may be modified and designed to resonate with a standing wave. Objects, such as cells, may be attracted to an anti-node, depicted by the X, which may be located in the flow path fluidically connected to a downstream partition.

In some cases, acoustic transfer of an object may occur by providing a standing acoustic wave. In some cases, acoustic transfer of an object may occur by providing acoustic streaming. Acoustic streaming is a second order hydrodynamic effect, in which an oscillatory excitation may be converted into a steady state vortex flow. This hydrodynamic effect of steady state vortex flow may be most pronounced near certain types of structural elements such as sharp corners, such as is shown in FIG. 42c. Thus, strategic placement and number of these structural elements may be employed to establish desired flow patterns such as a steady state hydrodynamic flow in a device to advantageously push an object, such as a cell, into a flow stream that may be connected through a partition.

Designing different structural elements within a device and applying an acoustic streaming to the device may produce fluidic streams having different flow profiles. For example, positioning, number, and/or shape of different structural elements of a device in combination with application of acoustic streaming may influence a fluid flow direction within a path or channel of a device, a speed or velocity of fluid flow, a type of fluid flow (laminar or turbulent), or any combination thereof. A structural feature, such as a corner positioned within a path of the device in combination with application of acoustic streaming, may cause turbulent flow, eddie currents, or vortexing flow. A structural feature, such as an edge positioned within a path of the device in combination with application of acoustic streaming may modify or adjust the laminar flow profile. Acoustic streaming may comprise Rayleigh streaming and/or Schlichting streaming.

A frequency of an acoustic source may be from about 1 kHz to about 1000 kHz. A frequency of an acoustic source may be from about 1 kHz to about 10 kHz. A frequency of an acoustic source may be from about 10 kHz to about 100 kHz. A frequency of an acoustic source may be from about 100 kHz to about 10000 kHz. A frequency of an acoustic source may be from about 600 kHz to about 1000 kHz. A frequency of an acoustic source may be from about 700 kHz to about 850 kHz. A frequency of an acoustic source may be from about 750 kHz to about 900 kHz. A frequency of an acoustic source may comprise an acoustic wavelength that may be larger than any structural feature of a device.

In cases where acoustic streaming may be employed to transfer an object, placement of structural features (such as sharp corners or angular corners) may be important to create a fluidic vortex at a particular location within the device. Placement of structural features to create fluidic vortex under acoustic streaming may create a fluidic force to drive an object along a particular direction within a channel or to a particular position within a device, such as within a partition. A sharp corner may be a corner having about a 90 degree. A sharp corner may be a corner having from about a 40 degree angle and a 90 degree angle. A sharp corner may be a corner having from about a 45 degree angle and a 90 degree angle. A sharp corner may be a corner having from about a 50 degree angle and a 90 degree angle. A sharp corner may be a corner having from about a 55 degree angle and a 90 degree angle. A sharp corner may be a corner having from about a 60 degree angle and a 90 degree angle. A sharp corner may be a corner having from about a 65 degree angle and a 90 degree angle. A sharp corner may be a corner having from about a 70 degree angle and a 90 degree angle. A sharp corner may be a corner having from about a 75 degree angle and a 90 degree angle. A sharp corner may be a corner having from about a 80 degree angle and a 90 degree angle. One or more sharp corners positioned adjacent to one another may form a saw tooth pattern, or an array of beam-like structures.

In some cases, a frequency may produce a standing wave. In some cases, a frequency may not produce a standing wave. In such cases, the transfer of an object may be based on acoustic streaming in which structural resonances in the channels of a device may be excited, similar to vibrating beams. The vibrations may induce fluid vortices that may be prominently observed near sharp structural elements, such as shown in FIG. 42c.

In some cases, a channel positioned between a partition and a trap may comprise one or more structural elements that act in combination with acoustic streaming to direct an object along a path, channel, or partition. A channel may comprise one or more corners, one or more edges, or a combination thereof. A channel may comprise a saw tooth pattern of edges. A channel may comprise 1, 2, 3, 4, 5, 6, 7, 8, or more corners. A channel may comprise 1, 2, 3, 4, 5, 6, 7, 8 or more edges. A corner may comprise an edge comprising about a 90 degree angle. An edge may comprise less than about a 90 degree angle.

Figure 24:
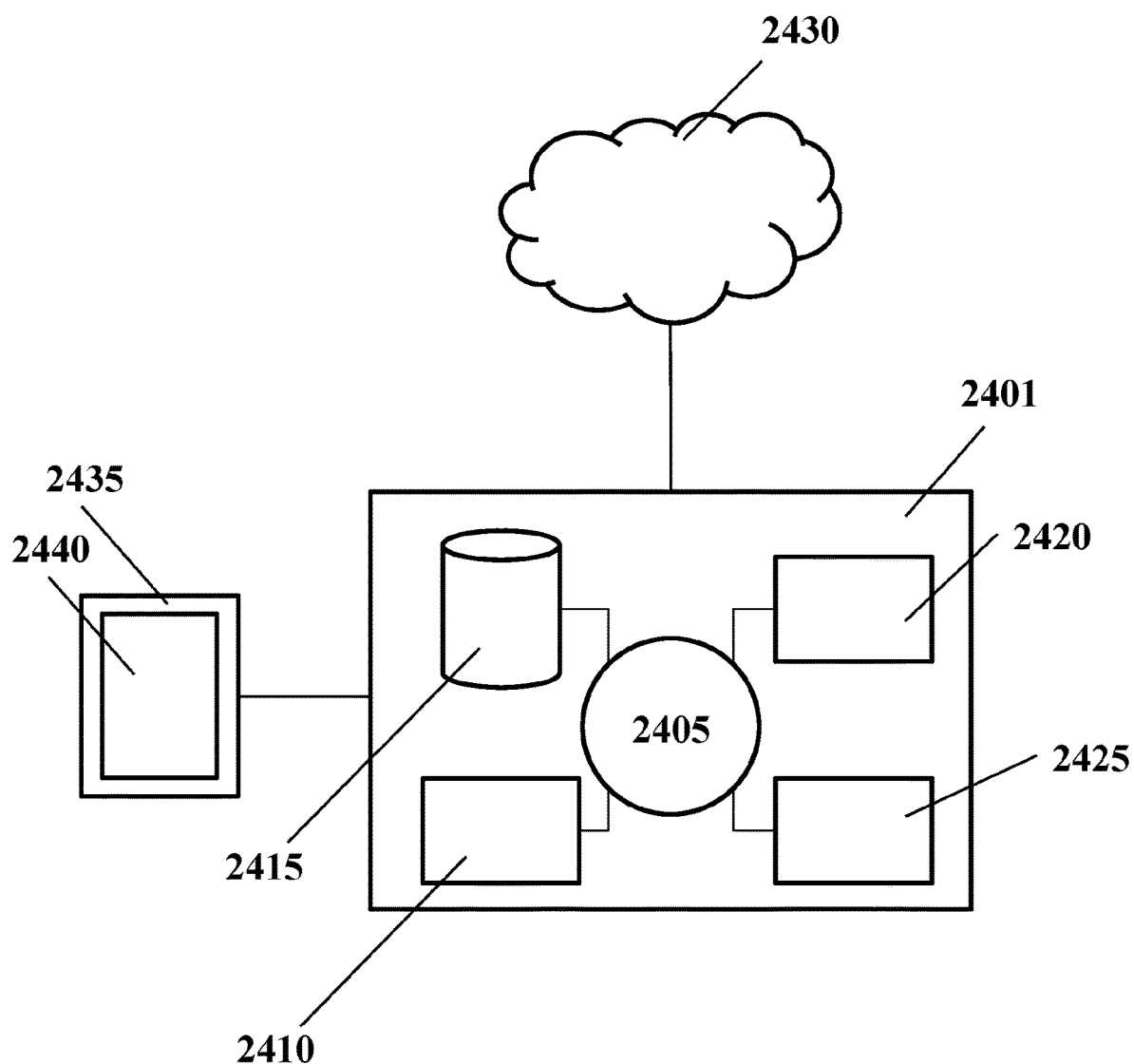
FIG. 24 shows a computer control system that is programmed or otherwise configured to implement methods provided herein.

The present disclosure provides computer control systems that are programmed to implement methods of the disclosure. FIG. 24 shows a computer system 2401 that is programmed or otherwise configured to instruct components of the devices and systems provided herein, such as the valves, pumps, sensors, or components operatively connects to the devices and systems provided herein such as microscopes, cameras, heaters, magnetic fields, or acoustic fields. The computer system 2401 can regulate various aspects of trapping and transferring objects into partitions of the present disclosure, such as, for example, controlling magnetic or acoustic fields, controlling a flow (such as on/off or flow rate) in a path adjacent thereto a partition, or controlling a temperature of a partition. The computer system 2401 can be an electronic device of a user or a computer system that is remotely located with respect to the electronic device. The electronic device can be a mobile electronic device.

The computer system 2401 includes a central processing unit (CPU, also "processor" and "computer processor" herein) 2405, which can be a single core or multi core processor, or a plurality of processors for parallel processing. The computer system 2401 also includes memory or memory location 2410 (e.g., random-access memory, read-only memory, flash memory), electronic storage unit 2415 (e.g., hard disk), communication interface 2420 (e.g., network adapter) for communicating with one or more other systems, and peripheral devices 2425, such as cache, other memory, data storage and/or electronic display adapters. The memory 2410, storage unit 2415, interface 2420 and peripheral devices 2425 are in communication with the CPU 2405 through a communication bus (solid lines), such as a motherboard. The storage unit 2415 can be a data storage unit (or data repository) for storing data. The computer system 2401 can be operatively coupled to a computer network ("network") 2430 with the aid of the communication interface 2420. The network 2430 can be the Internet, an internet and/or extranet, or an intranet and/or extranet that is in communication with the Internet. The network 2430 in some cases is a telecommunication and/or data network. The network 2430 can include one or more computer servers, which can enable distributed computing, such as cloud computing. The network 2430, in some cases with the aid of the computer system 2401, can implement a peer-to-peer network, which may enable devices coupled to the computer system 2401 to behave as a client or a server.

The CPU 2405 can execute a sequence of machine-readable instructions, which can be embodied in a program or software. The instructions may be stored in a memory location, such as the memory 2410. The instructions can be directed to the CPU 2405, which can subsequently program or otherwise configure the CPU 2405 to implement methods of the present disclosure. Examples of operations performed by the CPU 2405 can include fetch, decode, execute, and writeback.

The CPU 2405 can be part of a circuit, such as an integrated circuit. One or more other components of the system 2401 can be included in the circuit. In some cases, the circuit is an application specific integrated circuit (ASIC).

The storage unit 2415 can store files, such as drivers, libraries and saved programs. The storage unit 2415 can store user data, e.g., user preferences and user programs. The computer system 2401 in some cases can include one or more additional data storage units that are external to the computer system 2401, such as located on a remote server that is in communication with the computer system 2401 through an intranet or the Internet.

The computer system 2401 can communicate with one or more remote computer systems through the network 2430. For instance, the computer system 2401 can communicate with a remote computer system of a user (e.g., portable PC, tablet PC, Smart phones). Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 2401 via the network 2430.

Methods as described herein can be implemented by way of machine (e.g., computer processor) executable code stored on an electronic storage location of the computer system 2401, such as, for example, on the memory 2410 or electronic storage unit 2415. The machine executable or machine readable code can be provided in the form of software. During use, the code can be executed by the processor 2405. In some cases, the code can be retrieved from the storage unit 2415 and stored on the memory 2410 for ready access by the processor 2405. In some situations, the electronic storage unit 2415 can be precluded, and machine-executable instructions are stored on memory 2410.

The code can be pre-compiled and configured for use with a machine having a processer adapted to execute the code, or can be compiled during runtime. The code can be supplied in a programming language that can be selected to enable the code to execute in a pre-compiled or as-compiled fashion.

Aspects of the systems and methods provided herein, such as the computer system 2401, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 2401 can include or be in communication with an electronic display 2435 that comprises a user interface (UI) 2440 for providing, for example, an output from a sensor, an output from a camera or a microscope operatively connected to the device or system provided herein. Examples of UI's include, without limitation, a graphical user interface (GUI) and web-based user interface.

Methods and systems of the present disclosure can be implemented by way of one or more algorithms. An algorithm can be implemented by way of software upon execution by the central processing unit 2405. The algorithm can, for example, maintain a culture parameter at a set value (such as a constant temperature within a partition), can introduce a substance (such as a drug or lysis buffer) into one or more partitions at a specific time or during a specific sequence, determine or commute a biological result obtained from a sensor, can automate at least in part the devices or systems provided herein.

Quantities

A hydrodynamic resistance of a hydrodynamic trap may be about $10^{15}$ Netwons*second per meter^5 (Ns/m$^5$). A hydrodynamic resistance of a hydrodynamic trap may be about $0.01 \times 10^{15}$ Ns/m$^5$. A hydrodynamic resistance of a hydrodynamic trap may be about $0.1 \times 10^{15}$ Ns/m$^5$. A hydrodynamic resistance of a hydrodynamic trap may be about $1 \times 10^{15}$ Ns/m$^5$. A hydrodynamic resistance of a hydrodynamic trap may be about $5 \times 10^{15}$ Ns/m$^5$. A hydrodynamic resistance of a hydrodynamic trap may be about $10 \times 10^{15}$ Ns/m$^5$. A hydrodynamic resistance of a hydrodynamic trap may be about $50 \times 10^{15}$ Ns/m$^5$. A hydrodynamic resistance of a hydrodynamic trap may be about $100 \times 10^{15}$ Ns/m$^5$.

A width of a partition may be about 20 micrometers (um). A width of a partition may be about 30 um. A width of a partition may be about 30 um. A width of a partition may be about 40 um. A width of a partition may be about 50 um. A width of a partition may be about 60 um. A width of a partition may be about 70 um. A width of a partition may be about 80 um. A width of a partition may be about 90 um. A width of a partition may be about 100 um. A width of a partition may be about 125 um. A width of a partition may be about 150 um. A width of a partition may be about 175 um. A width of a partition may be about 200 um. A width of a partition may be about 225 um. A width of a partition may be about 250 um.

A width of a partition may be from about 20 um to about 200 um. A width of a partition may be from about 10 um to about 100 um. A width of a partition may be from about 10 um to about 500 um. A width of a partition may be from about 20 um to about 100 um. A width of a partition may be from about 10 um to about 60 um. A width of a partition may be at least about 20 um. A width of a partition may be less than about 200 um. A width of a partition may be less than about 150 um. A width of a partition may be less than about 100 um.

A volume of a partition may be about 10 picoliters (pL). A volume of a partition may be about 20 pL. A volume of a partition may be about 30 pL. A volume of a partition may be about 40 pL. A volume of a partition may be about 50 pL. A volume of a partition may be about 60 pL. A volume of a partition may be about 70 pL. A volume of a partition may be about 80 pL. A volume of a partition may be about 90 pL. A volume of a partition may be about 100 pL. A volume of a partition may be about 125 pL. A volume of a partition may be about 150 pL.

A volume of a partition may be at least about 10 picoliters (pL). A volume of a partition may be at least about 50 pL. A volume of a partition may be at least about 100 pL. A volume of a partition may be less than about 200 pL. A volume of a partition may be less than about 100 pL. A volume of a partition may be less than about 75 pL. A volume of a partition may be from about 10 pL to about 200 pL. A volume of a partition may be from about 10 pL to about 100 pL. A volume of a partition may be from about 50 pL to about 200 pL. A volume of a partition may be from about 50 pL to about 150 pL. A volume of a partition may be from about 50 pL to about 500 pL. A volume of a partition may be from about 50 pL to about 1000 pL. A volume of a partition may be from about 20 pL to about 500 pL.

A width and a length of a partition may be equivalent to a monolayer of from about 1 to 8 cells. A width and a length of a partition may be equivalent to a monolayer of from about 1 to 10 cells. A width and a length of a partition may be equivalent to a monolayer of from about 1 to 20 cells. A width and a length of a partition may be equivalent to a monolayer of from about 1 to 30 cells. A width and a length of a partition may be equivalent to a monolayer of from about 1 to 40 cells. A width and a length of a partition may be equivalent to a monolayer of from about 1 to 50 cells. A width and a length of a partition may be equivalent to a monolayer of from about 1 to 75 cells. A width and a length of a partition may be equivalent to a monolayer of from about 1 to 100 cells. A width and a length of a partition may be equivalent to a monolayer of from about 1 to 200 cells. A width and a length of a partition may be equivalent to a monolayer of from about 1 to 500 cells. A width and a length of a partition may be equivalent to a monolayer of from about 1 to 1,000 cells.

A width and a length of a partition may be equivalent to a monolayer of less than about 8 cells. A width and a length of a partition may be equivalent to a monolayer of about 8 cells. A width and a length of a partition may be equivalent to a monolayer of less than about 10 cells. A width and a length of a partition may be equivalent to a monolayer of about 10 cells. A width and a length of a partition may be equivalent to a monolayer of less than about 20 cells. A width and a length of a partition may be equivalent to a monolayer of about 20 cells. A width and a length of a partition may be equivalent to a monolayer of less than about 30 cells. A width and a length of a partition may be equivalent to a monolayer of about 30 cells. A width and a length of a partition may be equivalent to a monolayer of less than about 40 cells. A width and a length of a partition may be equivalent to a monolayer of about 40 cells. A width and a length of a partition may be equivalent to a monolayer of less than about 50 cells. A width and a length of a partition may be equivalent to a monolayer of about 50 cells. A width and a length of a partition may be equivalent to a monolayer of less than about 100 cells. A width and a length of a partition may be equivalent to a monolayer of about 100 cells. A width and a length of a partition may be equivalent to a monolayer of less than about 500 cells. A width and a length of a partition may be equivalent to a monolayer of about 500 cells. A width and a length of a partition may be equivalent to a monolayer of less than about 1,000 cells. A width and a length of a partition may be equivalent to a monolayer of about 1,000 cells.

A distance from a trap to a partition adjacent thereto may be about 20 micrometers (um). A distance from a trap to a partition adjacent thereto may be about 30 um. A distance from a trap to a partition adjacent thereto may be about 30 um. A distance from a trap to a partition adjacent thereto may be about 40 um. A distance from a trap to a partition adjacent thereto may be about 50 um. A distance from a trap to a partition adjacent thereto may be about 60 um. A distance from a trap to a partition adjacent thereto may be about 70 um. A distance from a trap to a partition adjacent thereto may be about 80 um. A distance from a trap to a partition adjacent thereto may be about 90 um. A distance from a trap to a partition adjacent thereto may be about 100 um. A distance from a trap to a partition adjacent thereto may be about 125 um. A distance from a trap to a partition adjacent thereto may be about 150 um. A distance from a trap to a partition adjacent thereto may be about 175 um. A distance from a trap to a partition adjacent thereto may be about 200 um. A distance from a trap to a partition adjacent thereto may be about 225 um. A distance from a trap to a partition adjacent thereto may be about 250 um.

A distance from a trap to a partition adjacent thereto may be from about 20 um to about 200 um. A distance from a trap to a partition adjacent thereto may be from about 10 um to about 100 um. A distance from a trap to a partition adjacent thereto may be from about 10 um to about 500 um. A distance from a trap to a partition adjacent thereto may be from about 20 um to about 100 um. A distance from a trap to a partition adjacent thereto may be from about 10 um to about 60 um. A distance from a trap to a partition adjacent thereto may be from about 10 um to about 1,000 um. A distance from a trap to a partition adjacent thereto may be from about 20 um to about 1,000 um. A distance from a trap to a partition adjacent thereto may be from about 10 um to about 500 um. A distance from a trap to a partition adjacent thereto may be at least about 20 um. A distance from a trap to a partition adjacent thereto may be less than about 200 um. A distance from a trap to a partition adjacent thereto may be less than about 150 um. A distance from a trap to a partition adjacent thereto may be less than about 100 um. A distance from a trap to a partition adjacent thereto may be less than about 500 um. A distance from a trap to a partition adjacent thereto may be less than about 1,000 um.

At least about 10 partitions may be populated with at least one object by performing a collective transfer. At least about 50 partitions may be populated with at least one object by performing a collective transfer. At least about 100 partitions may be populated with at least one object by performing a collective transfer. At least about 200 partitions may be populated with at least one object by performing a collective transfer. At least about 300 partitions may be populated with at least one object by performing a collective transfer. At least about 400 partitions may be populated with at least one object by performing a collective transfer. At least about 500 partitions may be populated with at least one object by performing a collective transfer. At least about 1,000 partitions may be populated with at least one object by performing a collective transfer. At least about 1,500 partitions may be populated with at least one object by performing a collective transfer. At least about 2,000 partitions may be populated with at least one object by performing a collective transfer. At least about 3,000 partitions may be populated with at least one object by performing a collective transfer. At least about 4,000 partitions may be populated with at least one object by performing a collective transfer. At least about 5,000 partitions may be populated with at least one object by performing a collective transfer. At least about 10,000 partitions may be populated with at least one object by performing a collective transfer. At least about 15,000 partitions may be populated with at least one object by performing a collective transfer.

At least about 10 objects may be collectively transferred into partitions by performing a collective transfer. At least about 50 objects may be collectively transferred into partitions by performing a collective transfer. At least about 100 objects may be collectively transferred into partitions by performing a collective transfer. At least about 200 objects may be collectively transferred into partitions by performing a collective transfer. At least about 300 objects may be collectively transferred into partitions by performing a collective transfer. At least about 400 objects may be collectively transferred into partitions by performing a collective transfer. At least about 500 objects may be collectively transferred into partitions by performing a collective transfer. At least about 1,000 objects may be collectively transferred into partitions by performing a collective transfer. At least about 1,500 objects may be collectively transferred into partitions by performing a collective transfer. At least about 2,000 objects may be collectively transferred into partitions by performing a collective transfer. At least about 3,000 objects may be collectively transferred into partitions by performing a collective transfer. At least about 4,000 objects may be collectively transferred into partitions by performing a collective transfer. At least about 5,000 objects may be collectively transferred into partitions by performing a collective transfer. At least about 10,000 objects may be collectively transferred into partitions by performing a collective transfer. At least about 15,000 objects may be collectively transferred into partitions by performing a collective transfer.

A plurality of object may be greater than about 10 objects. A plurality of object may be greater than about 50 objects. A plurality of object may be greater than about 100 objects. A plurality of object may be greater than about 500 objects. A plurality of object may be greater than about 1,000 objects. A plurality of object may be greater than about 5,000 objects. A plurality of object may be greater than about 10,000 objects. A plurality of object may be greater than about 20,000 objects. A plurality of object may be greater than about 30,000 objects. A plurality of object may be greater than about 50,000 objects. A plurality of object may be greater than about 50,000 objects. A plurality of object may be greater than about 100,000 objects.

A volume of a partition may accommodate at least about 1 cell doubling. A volume of a partition may accommodate at least about 2 cell doublings. A volume of a partition may accommodate at least about 3 cell doublings. A volume of a partition may accommodate at least about 4 cell doublings. A volume of a partition may accommodate at least about 5 cell doublings. A volume of a partition may accommodate at least about 6 cell doublings. A volume of a partition may accommodate at least about 7 cell doublings. A volume of a partition may accommodate at least about 8 cell doublings. A volume of a partition may accommodate at least about 9 cell doublings. A volume of a partition may accommodate at least about 10 cell doublings. A volume of a partition may accommodate from about 1 cell doubling to about 10 cell doublings. A volume of a partition may accommodate from about 1 cell doubling to about 7 cell doublings. A volume of a partition may accommodate from about 1 cell doubling to about 5 cell doublings. A volume of a partition may accommodate from about 1 cell doubling to about 15 cell doublings.

An object occupancy rate for a plurality of partitions, after a collective transfer, may be about 60%. An object occupancy rate for a plurality of partitions, after a collective transfer, may be greater than about 60%. An object occupancy rate for a plurality of partitions, after a collective transfer, may be about 75%. An object occupancy rate for a plurality of partitions, after a collective transfer, may be greater than about 75%. An object occupancy rate for a plurality of partitions, after a collective transfer, may be about 80%. An object occupancy rate for a plurality of partitions, after a collective transfer, may be greater than about 80%. An object occupancy rate for a plurality of partitions, after a collective transfer, may be about 85%. An object occupancy rate for a plurality of partitions, after a collective transfer, may be greater than about 85%. An object occupancy rate for a plurality of partitions, after a collective transfer, may be about 90%. An object occupancy rate for a plurality of partitions, after a collective transfer, may be greater than about 90%. An object occupancy rate for a plurality of partitions, after a collective transfer, may be about 95%. An object occupancy rate for a plurality of partitions, after a collective transfer, may be greater than about 95%. An object occupancy rate for a plurality of partitions, after a collective transfer, may be about 96%. An object occupancy rate for a plurality of partitions, after a collective transfer, may be greater than about 96%. An object occupancy rate for a plurality of partitions, after a collective transfer, may be about 97%. An object occupancy rate for a plurality of partitions, after a collective transfer, may be greater than about 97%. An object occupancy rate for a plurality of partitions, after a collective transfer, may be about 98%. An object occupancy rate for a plurality of partitions, after a collective transfer, may be greater than about 98%. An object occupancy rate for a plurality of partitions, after a collective transfer, may be about 99%. An object occupancy rate for a plurality of partitions, after a collective transfer, may be greater than about 99%.

A movement of an object, such as a collective transfer to a partition, may have a precision of movement of at least about +/−2.0 micrometers (um). A precision of movement of an object may be at least about +/−1.5 um. A precision of movement of an object may be at least about +/−1.0 um. A precision of movement of an object may be at least about +/−0.5 um. A precision of movement of an object may be at least about +/−0.1 um. A precision of movement of an object may be at least about +/−3.0 um. A precision of movement of an object may be at least about +/−4.0 um. A precision of movement of an object may be at least about +/−5.0 um.

A plurality of traps may comprise about 10 traps. A plurality of traps may comprise greater than about 10 traps. A plurality of traps may comprise about 50 traps. A plurality of traps may comprise greater than about 50 traps. A plurality of traps may comprise about 100 traps. A plurality of traps may comprise greater than about 100 traps. A plurality of traps may comprise about 500 traps. A plurality of traps may comprise greater than about 500 traps. A plurality of traps may comprise about 1,000 traps. A plurality of traps may comprise greater than about 1,000 traps. A plurality of traps may comprise about 5,000 traps. A plurality of traps may comprise greater than about 5,000 traps. A plurality of traps may comprise about 10,000 traps. A plurality of traps may comprise greater than about 10,000 traps. A plurality of traps may comprise about 50,000 traps. A plurality of traps may comprise greater than about 50,000 traps. A plurality of traps may comprise about 100,000 traps. A plurality of traps may comprise greater than about 100,000 traps. There may be one trap for each partition of a microfluidic chip. There may be more than one trap for each partition of a microfluidic chip.

A packing density of partitions on a microfluidic chip may be about 10 partitions per square centimeter ($p/cm^2$) of the microfluidic chip. A packing density of partitions on a microfluidic chip may be greater than about 10 $p/cm^2$ of the microfluidic chip. A packing density of partitions on a microfluidic chip may be about 50 $p/cm^2$ of the microfluidic chip. A packing density of partitions on a microfluidic chip may be greater than about 50 $p/cm^2$ of the microfluidic chip. A packing density of partitions on a microfluidic chip may be about 100 $p/cm^2$ of the microfluidic chip. A packing density of partitions on a microfluidic chip may be greater than about 100 $p/cm^2$ of the microfluidic chip. A packing density of partitions on a microfluidic chip may be about 500 $p/cm^2$ of the microfluidic chip. A packing density of partitions on a microfluidic chip may be greater than about 500 $p/cm^2$ of the microfluidic chip. A packing density of partitions on a microfluidic chip may be about 1000 $p/cm^2$ of the microfluidic chip. A packing density of partitions on a microfluidic chip may be greater than about 1000 $p/cm^2$ of the microfluidic chip. A packing density of partitions on a microfluidic chip may be about 2000 $p/cm^2$ of the microfluidic chip. A packing density of partitions on a microfluidic chip may be greater than about 2000 $p/cm^2$ of the microfluidic chip. A packing density of partitions on a microfluidic chip may be from about 10 $p/cm^2$ to about 2000 $p/cm^2$. A packing density of partitions on a microfluidic chip may be from about 500 $p/cm^2$ to about 1000 $p/cm^2$. A packing density of partitions on a microfluidic chip may be from about 1000 $p/cm^2$ to about 2000 $p/cm^2$.

An outer length and an outer width of a microfluidic chip may be about 12 inches (in) by 12 in. An outer length and an outer width of a microfluidic chip may be less than about 12 in by 12 in. An outer length and an outer width of a microfluidic chip may be about 10 in by 10 in. An outer length and an outer width of a microfluidic chip may be less than about 10 in by 10 in. An outer length and an outer width of a microfluidic chip may be about 8 in by 8 in. An outer length and an outer width of a microfluidic chip may be less than about 8 in by 8 in. An outer length and an outer width of a microfluidic chip may be about 6 in by 6 in. An outer length and an outer width of a microfluidic chip may be less than about 6 in by 6 in. An outer length and an outer width of a microfluidic chip may be about 5 in by 5 in. An outer length and an outer width of a microfluidic chip may be less than about 5 in by 5 in. An outer length and an outer width of a microfluidic chip may be about 4 in by 4 in. An outer length and an outer width of a microfluidic chip may be less than about 4 in by 4 in. An outer length and an outer width of a microfluidic chip may be about 3.5 in by 3.5 in. An outer length and an outer width of a microfluidic chip may be less than about 3.5 in by 3.5 in. An outer length and an outer width of a microfluidic chip may be about 3 in by 3 in. An outer length and an outer width of a microfluidic chip may be less than about 3 in by 3 in. An outer length and an outer width of a microfluidic chip may be about 2.5 in by 2.5 in. An outer length and an outer width of a microfluidic chip may be less than about 2.5 in by 2.5 in. An outer length and an outer width of a microfluidic chip may be about 2 in by 2 in. An outer length and an outer width of a microfluidic chip may be less than about 2 in by 2 in. An outer length and an outer width of a microfluidic chip may be about 1.5 in by 1.5 in. An outer length and an outer width of a microfluidic chip may be less than about 1.5 in by 1.5 in.

A volume of a partition may be equivalent to a volume of at least about 10 cells. A volume of a partition may be equivalent to a volume of at least about 20 cells. A volume of a partition may be equivalent to a volume of at least about 30 cells. A volume of a partition may be equivalent to a volume of at least about 40 cells. A volume of a partition may be equivalent to a volume of at least about 50 cells. A volume of a partition may be equivalent to a volume of at least about 60 cells. A volume of a partition may be equivalent to a volume of at least about 70 cells. A volume of a partition may be equivalent to a volume of at least about 80 cells. A volume of a partition may be equivalent to a volume of at least about 90 cells. A volume of a partition may be equivalent to a volume of at least about 100 cells.

A thickness of an electrical conductor may be at least about 10 nanometers (nm). A thickness of an electrical conductor may be at least about 50 nm. A thickness of an electrical conductor may be at least about 100 nm. A thickness of an electrical conductor may be at least about 150 nm. A thickness of an electrical conductor may be at least about 200 nm. A thickness of an electrical conductor may be at least about 250 nm.

A microfluidic device may comprise one or more sensors. A microfluidic device may comprise at least 2 sensors. A microfluidic device may comprise at least 3 sensors. A microfluidic device may comprise at least 4 sensors. A microfluidic device may comprise at least 5 sensors. A microfluidic device may comprise at least 10 sensors. A microfluidic device may comprise at least 15 sensors. A microfluidic device may comprise a single type of sensor for an individual device. A microfluidic device may comprise a single type of sensor for each partition of an individual device. A microfluidic device may comprise a single type of sensor for a portion of partitions of a plurality of partitions of an individual device. A microfluidic device may comprise two of the same type of sensor. A microfluidic device may comprise at least 2 different types of sensors. A microfluidic device may comprise at least 3 different types of sensors. A microfluidic device may comprise at least 4 different types of sensors.

A speed of an object, such as a magnetic bead, may travel along a track, such as a magnetic track at a speed from about 1 micrometer per second (um/sec) to about 100 um/sec. A speed of an object may be from about 1 um/sec to about 200 um/sec. A speed of an object may be from about 1 um/sec to about 500 um/sec. A speed of an object may be from about 10 um/sec to about 100 um/sec. A speed of an object may be from about 50 um/sec to about 100 um/sec.

An object, such as a cell, may be maintained or cultured in the microfluidic chip for about 1 hour. An object may be maintained or cultured in a microfluidic device for at least about 1 hour. An object, such as a cell, may be maintained or cultured in the microfluidic chip for about 2 hours. An object may be maintained or cultured in a microfluidic device for at least about 2 hours. An object, such as a cell, may be maintained or cultured in the microfluidic chip for about 4 hours. An object may be maintained or cultured in a microfluidic device for at least about 4 hours. An object, such as a cell, may be maintained or cultured in the microfluidic chip for about 6 hours. An object may be maintained or cultured in a microfluidic device for at least about 6 hours. An object may be maintained or cultured in a microfluidic device for about 12 hours. An object may be maintained or cultured in a microfluidic device for at least about 12 hours. An object may be maintained or cultured in a microfluidic device for about 18 hours. An object may be maintained or cultured in a microfluidic device for at least about 18 hours. An object may be maintained or cultured in a microfluidic device for about 1 day. An object may be maintained or cultured in a microfluidic device for at least about 1 day. An object may be maintained or cultured in a microfluidic device for about 2 days. An object may be maintained or cultured in a microfluidic device for at least about 2 days. An object may be maintained or cultured in a microfluidic device for about 3 days. An object may be maintained or cultured in a microfluidic device for at least about 3 days. An object may be maintained or cultured in a microfluidic device for about 4 days. An object may be maintained or cultured in a microfluidic device for at least about 4 days. An object may be maintained or cultured in a microfluidic device for about 5 days. An object may be maintained or cultured in a microfluidic device for at least about 5 days. An object may be maintained or cultured in a microfluidic device for about 6 days. An object may be maintained or cultured in a microfluidic device for at least about 6 days. An object may be maintained or cultured in a microfluidic device for about 7 days. An object may be maintained or cultured in a microfluidic device for at least about 7 days. An object may be maintained or cultured in a microfluidic device for about 10 days. An object may be maintained or cultured in a microfluidic device for at least about 10 days. An object may be maintained or cultured in a microfluidic device for about 14 days. An object may be maintained or cultured in a microfluidic device for at least about 14 days.

About 100 objects, such as cells, may be evaluated in parallel using the devices, systems, and methods provided herein. Greater than about 100 objects may be evaluated in parallel. About 500 objects may be evaluated in parallel. Greater than about 500 objects may be evaluated in parallel. About 1,000 objects may be evaluated in parallel. Greater than about 1,000 objects may be evaluated in parallel. About 5,000 objects may be evaluated in parallel. Greater than about 5,000 objects may be evaluated in parallel. About 10,000 objects may be evaluated in parallel. Greater than about 10,000 objects may be evaluated in parallel.

A length of a barcode comprising a nucleic acid sequence may be about 5 basepairs (bp). A length of a barcode may be at least about 5 bp. A length of a barcode may be about 6 bp. A length of a barcode may be at least about 6 bp. A length of a barcode may be about 7 bp. A length of a barcode may be at least about 7 bp. A length of a barcode may be about 8 bp. A length of a barcode may be at least about 8 bp. A length of a barcode may be about 9 bp. A length of a barcode may be at least about 9 bp. A length of a barcode may be about 10 bp. A length of a barcode may be at least about 10 bp. A length of a barcode may be about 15 bp. A length of a barcode may be at least about 15 bp. A length of a barcode may be about 20 bp. A length of a barcode may be at least about 20 bp.

An acoustic standing wave may be applied to a device configured to transfer an object from a trap to an adjacent partition. A frequency of an acoustic standing wave may be from about 1 MHz to about 20 MHz. A frequency of an acoustic standing wave may be from about 1 MHz to about 5 MHz. A frequency of an acoustic standing wave may be from about 1 MHz to about 10 MHz. A frequency of an acoustic standing wave may be from about 1 MHz to about 15 MHz. A frequency of an acoustic standing wave may be from about 1 MHz to about 25 MHz. A frequency of an acoustic standing wave may be from about 1 MHz to about 30 MHz. A frequency of an acoustic standing wave may be from about 0.5 MHz to about 20 MHz. A frequency of an acoustic standing wave may be from about 5 MHz to about 20 MHz. A frequency of an acoustic standing wave may be from about 10 MHz to about 20 MHz. A frequency of an acoustic standing wave may be from about 15 MHz to about 20 MHz. A frequency of an acoustic standing wave may be about: 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 MHz. A frequency of an acoustic standing wave may be constant. A frequency of an acoustic standing wave may be intermittent, such as intermittent applied across a period of time. A frequency of an acoustic standing wave may be time varying, such as an adjustable frequency that may be modified by a user or a controller.

An acoustic streaming may be applied to a device configured to transfer an object from a trap to an adjacent partition. A frequency of an acoustic streaming may be from about 1 kHz to about 2000 kHz. A frequency of an acoustic streaming may be from about 1 kHz to about 1800 kHz. A frequency of an acoustic streaming may be from about 1 kHz to about 1600 kHz. A frequency of an acoustic streaming may be from about 1 kHz to about 1400 kHz. A frequency of an acoustic streaming may be from about 1 kHz to about 1200 kHz. A frequency of an acoustic streaming may be from about 1 kHz to about 1000 kHz. A frequency of an acoustic streaming may be from about 1 kHz to about 800 kHz. A frequency of an acoustic streaming may be from about 1 kHz to about 600 kHz. A frequency of an acoustic streaming may be from about 1 kHz to about 400 kHz. A frequency of an acoustic streaming may be from about 1 kHz to about 200 kHz. A frequency of an acoustic streaming may be from about 1 kHz to about 100 kHz. A frequency of an acoustic streaming may be from about 1 kHz to about 80 kHz. A frequency of an acoustic streaming may be from about 1 kHz to about 60 kHz. A frequency of an acoustic streaming may be from about 1 kHz to about 40 kHz. A frequency of an acoustic streaming may be from about 1 kHz to about 20 kHz. A frequency of an acoustic streaming may be from about 1 kHz to about 10 kHz. A frequency of an acoustic streaming may be from about 10 kHz to about 2000 kHz. A frequency of an acoustic streaming may be from about 100 kHz to about 2000 kHz. A frequency of an acoustic streaming may be from about 200 kHz to about 2000 kHz. A frequency of an acoustic streaming may be from about 400 kHz to about 2000 kHz. A frequency of an acoustic streaming may be from about 600 kHz to about 2000 kHz. A frequency of an acoustic streaming may be from about 800 kHz to about 2000 kHz. A frequency of an acoustic streaming may be from about 1000 kHz to about 2000 kHz. A frequency of an acoustic streaming may be from about 1200 kHz to about 2000 kHz. A frequency of an acoustic streaming may be from about 1400 kHz to about 2000 kHz. A frequency of an acoustic streaming may be from about 1600 kHz to about 2000 kHz. A frequency of an acoustic streaming may be from about 1800 kHz to about 2000 kHz. A frequency of an acoustic streaming may be from about 500 kHz to about 1500 kHz. A frequency of an acoustic streaming may be from about 100 kHz to about 1000 kHz. A frequency of an acoustic streaming may be from about 100 kHz to about 500 kHz.

A liquid medium may be introduced into a device, such as introduced into one or more paths, one or more traps, one or more partitions, or a combination thereof. A viscosity of a liquid medium, such as a buffer or media, may vary or may be constant. A liquid may be selected for use with a device or system herein based on a liquid property such as a viscosity. A particular viscosity may be advantageous to produce desired flow parameters within a partition when an acoustic stimulus such as a standing wave or ascoustic streaming is applied to a device or system. A viscosity of a liquid medium may range from about 0.001 centipoise (cP) to about 0.1 cP. A viscosity of a liquid medium may range from about 0.001 centipoise (cP) to about 0.08 cP. A viscosity of a liquid medium may range from about 0.001 centipoise (cP) to about 0.06 cP. A viscosity of a liquid medium may range from about 0.001 centipoise (cP) to about 0.04 cP. A viscosity of a liquid medium may range from about 0.001 centipoise (cP) to about 0.02 cP. A viscosity of a liquid medium may range from about 0.001 centipoise (cP) to about 0.01 cP. A viscosity of a liquid medium may range from about 0.001 centipoise (cP) to about 0.008 cP. A viscosity of a liquid medium may range from about 0.001 centipoise (cP) to about 0.006 cP. A viscosity of a liquid medium may range from about 0.001 centipoise (cP) to about 0.004 cP. A viscosity of a liquid medium may range from about 0.001 centipoise (cP) to about 0.002 cP. A viscosity of a liquid medium may range from about 0.004 centipoise (cP) to about 0.1 cP. A viscosity of a liquid medium may range from about 0.006 centipoise (cP) to about 0.1 cP. A viscosity of a liquid medium may range from about 0.008 centipoise (cP) to about 0.1 cP. A viscosity of a liquid medium may range from about 0.01 centipoise (cP) to about 0.1 cP. A viscosity of a liquid medium may range from about 0.02 centipoise (cP) to about 0.1 cP. A viscosity of a liquid medium may range from about 0.04 centipoise (cP) to about 0.1 cP. A viscosity of a liquid medium may range from about 0.06 centipoise (cP) to about 0.1 cP. A viscosity of a liquid medium may range from about 0.08 centipoise (cP) to about 0.1 cP. A viscosity of a liquid medium may range from about 0.004 centipoise (cP) to about 0.04 cP. A viscosity of a liquid medium may range from about 0.008 centipoise (cP) to about 0.08 cP. A viscosity of a liquid medium may range from about 0.008 centipoise (cP) to about 0.02 cP.

EXAMPLES

Example 1—Correlate Cellular Phenotype and Genotype of Single Cells

Magnetic beads will first be organized into an array, and the barcodes associated with each bead will be identified with a pyrosequencing protocol. Thereafter, single FLT3-ITD+ AML cells will be populated (MV4;11) into the array. The cells will be maintained on the microfluidic chip for 7 days, while exposing the cells to Quizartinib (CAS Number 950769-58-1). At a desired endpoint, the micro-valves will be closed, and the single cell RNA will be reverse transcribed onto the single magnetic beads with known barcodes. Following pooling of beads, second strand synthesis, linear amplification, RNA fragmentation, adapter labeling, reverse transcription, and selection of double labeled DNA, that DNA will be further selected by polymerase chain reaction (PCR) amplification using cell-specific barcodes (corresponding to resistant cells of interest) to generate sequencing-compatible double stranded DNAs from selected cells representing their single cell transcriptomes which will be analyzed by Illumina HiSeq. Gene Set Enrichment Analysis will be used to identify signatures of active FLT3 signaling in selected resistant cells (relative to reference, drug sensitive cells treated with Quizartinib).

Figure 10:
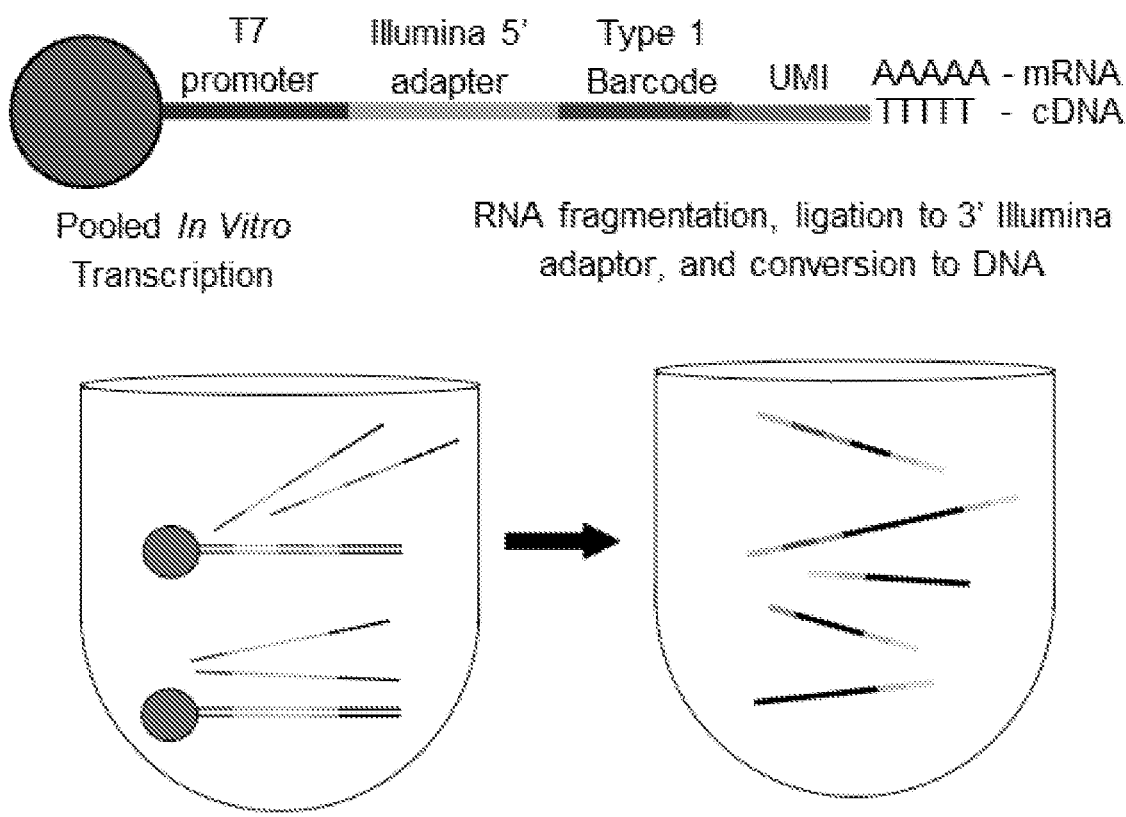
FIG. 10 shows DNA barcoded magnetic beads used to capture and reverse transcribe single cell RNA.

Example 2—Validate Single CEL-Seq Using On-Chip Co-Localized Cells and Magnetic Beads Single cells and single magnetic beads will be organized into arrays. A reverse transcriptase(RT)/lysis buffer will be introduced into the microfluidic channels. The micro-valves of all channels will be closed to conduct the reverse transcription reactions in parallel. Polyadenylated mRNAs released from lysed cells will be captured with polyT functionalized capture probes on the surface of magnetic beads (FIG. 10), then reversed transcribed using RT/lysis buffer that includes 100 mM Tris-HCl at 8.0 pH, 5× First-Strand buffer, 1% (v/v) IGEPAL, 2.5 mM DTT, 10 mM Dithiothreitol, Murine RNase inhibitor, and Superscript III RT Enzyme suspended in nuclease-free water. To perform RT, the array will be incubated at 50° C. for 2 hours to allow cDNA synthesis to occur, followed by heating the chip for 15 minutes at 70° C. to terminate the reaction. After cooling the chip to room temperature, the micro-valves will be opened and the transistors will all be turned on to release the barcoded magnetic beads from their partition (each now carrying the transcribed cDNA of the co-assembled single cells). The magnetic beads will then be extracted from the chip by rinsing the microfluidic channels into an Eppendorf tube. After pooling the magnetic beads, established CEL-Seq procedures will be followed to transcribe and fragment the RNA, ligate 3' Illumina adaptors, then convert the RNA to DNA, and enrich the DNA containing both 3' and 5' Illumina adaptors. DNAs with dual labeling will be selected and subjected to paired end sequencing using the Illumina HiSeq 2500.

Example 3—Functionalize 10 Micrometer Diameter Magnetic Beads, Each with a Unique DNA Barcode DNA strands from IDT with a 5' biotin tag will be designed with the following structure: T7 promoter region, Illumina 5' adaptor, N bp barcode, unique molecular identifier (UMI), and terminated with a poly T tail (FIG. 9). To avoid misidentifications during pyrosequencing, the barcodes will be limited to non-repeat sequences, which allows the fluorescent read-out to be identified as a binary signal (presence or absence of fluorescence). The number of barcodes will scale as $\Omega=3^N$ combinations, where N is the barcode length. The single cell array will have R=40 rows, where each row has P=40 apartments, and each apartment holds a single cell, with a total of C=R×P=1,600 apartments in the array. To limit the probability of a duplicate barcode in a given row to less than 50%, the number of barcodes should be at least $Q \neq P$ $2 \neq 1,600$. This analysis implies that the minimum barcode length should be N=log(1600/3)≈6 base pairs; however barcodes >10 bp in length will be used to increase fidelity, reduce false positives, and maintain base frequency parity. These barcodes will be purchased in plate format by IDT, with the 3' ends functionalized with random UMIs (10-15 bp), and grafted to poly T tails to complete the required structure. Streptavidin coated magnetic beads will be incubated in these plates, rinsed thoroughly, and pooled to establish a bead library, in which each magnetic bead is associated with a unique barcode.

Example 4—Pyrosequencing of Beads in Bulk

The pyrosequencing protocol will be calibrated in bulk. The buffer will consist of 0.1M Tris Acetate, 0.5 mM EDTA, 5 mM Magnesium Acetate, 0.1% bovine serum albumin, 1 mM Dithiothreitol, 5 μM 5'adenosine-5'-phosphosulfate, 0.4 mg/mL of MW 360,000 Poly(vinylpyrrolidone), and 100 μg/mL D-luciferin. The enzyme mix will contain 25 mU ATP sulfurylase, 20 μg/mL purified luciferase, 50 μg/mL *E. coli* ssDNA binding protein, 80 U/mL exonuclease-deficient Klenow polymerase, 0.1 μM sodium pyrophosphate, and 200 U/mL Sequenase 2.0, to which the deoxynucleotides, dCTP, dGTP, dTTP, and α-thio deoxyadenosine triphosphate will be added at concentrations of 10-50 μM (the latter is substituted for dATP due to cross-reactivity). After dNTP addition, the enzymes will catalyze a reaction resulting in the release of a bioluminescent signal from the beads as each base is added. The remaining dNTPs will be deactivated by addition of 1 U/mL of apyrase.

Example 5—Pyrosequencing of Beads Arrayed on Chip

The pyrosequencing protocol will be demonstrated on chip by first arraying magnetic beads at a concentration of one bead per apartment. Once arrayed, the fluorescent signature of each bead will be recorded during an SBS protocol. The workflow of the sequencing reagents will be organized into kernels based on established protocols, where the first kernel will introduce ~30 seconds of buffer flow, followed by ~10 seconds of enzyme mix flow with the dNTPs. A low-resolution image will be captured, and the remaining dNTPs will be deactivated with a ~30 seconds of apyrase rinse. After ~40 cycles lasting a total of ~1 hour, each array site will be assigned to a unique barcode. To mitigate non-specific adhesion of enzymes or molecules inside the microchannels, the microchannels will be functionalized with POEGMA, a coating that may be effective in resisting non-specific adhesion of both molecules and cells to the microfabricated substrates. The array spatial period will be 100-200 μm, such that the field of view to cover all 1,600 array sites will be less than 10 mm. A CCD camera will image all array elements simultaneously in a 5× objective.

Example 6—Scale Up the Hardware and Microfluidics to Organize Thousands of Single Cells The number of control wires will be increased while reducing the wire resistances to enable low power switch architectures using 10 Volts power supplies. The microfluidic channels and micro-valving systems will be integrated to individually address the fluidic paths in each row of the array. The cell placement and error correction algorithms will be optimized to achieve >99% single cell array occupancy in less than 1 hour. To increase the number of control wires, the PCI card edge connectors will be re-designed to allow more wires to be connected to the chip. The metal layer thicknesses will be increased to minimize the wire resistances. A microfluidic flow control module will be designed and built to deliver magnetized cells to microchannels in the array (passive delivery), after which the magnetic circuits will organize nearby cells into the desired chambers (active delivery). Microfluidic channels will be built by inverse molding in PDMS with masters fabricated in SU-8. Fluidic micro-valves will be built using Quake-style architectures. The micro-valves will be controlled with Elvesys flow switch matrices. The interior flow channel surfaces will be functionalized with POEGMA brushes to reduce non-specific cell adhesion. Additional flow switch matrices will be added to control 40 valves. Adopting the crossbar memory architecture comprising 40 control wires (T1-T40) and 40 control valves (V1-V40), 1,600 array elements will be individually addressable (FIG. 8b). The transistors and micro-valves will be actuated with customized LABVIEW software. The microscopy filters and stage will be controlled with Metamorph software, and finally, the image analysis will be conducted with MATLAB and ImageJ.

The workflow will first introduce magnetically labeled cells 801 into the flow channels 804 (white spaces in FIG. 8a), after which the flow is stopped and the magnetic transistors will be activated to organize the nearby cells into partitions of the array 803. This process may be repeated to add a second cell or a bead 802 into each of the partitions of the array. The concentration of the cell suspension will be optimized such that after the magnetic sorting step is complete, the majority of micro-wells will contain a single cell. This procedure will allow most of the array sites to be populated within minutes; however some assembly errors will require correction, particularly array sites with dual occupancy. In these cases, the excess cells will be automatically identified by image tracking and extracted by activating the transistor switches and microfluidic controllers.

Example 7—Optimize On-Chip Incubator and Microfluidics to Maintain Cells for >7 Days Custom-made incubator systems will be developed and resistive heaters and Arduino controllers will be optimized to maintain the microfluidic chip temperature at 37° C. The chip temperature will be controlled with resistive heating through indium tin oxide (ITO) coated glass slides. An Arduino chipset and controller algorithm will maintain set temperatures, independently verified with Negative Temperature Coefficient (NTC) Thermistors (U.S. Sensor Corp). Cell viability will be demonstrated at >95% cell viability for 3 days and at >95% cell viability for 7 days. The temperature sensors will be miniaturized. Pre-mixed CO2 will be filled in the control valves and stock media. Nutrient exchange will be achieved by continuously flowing cell culture media through the microchannels. Cell viability will be measured by using both the Yopro-1 viability indicator (Invitrogen) and by counting cell numbers over time. Automatic scanning images of the array region will be obtained every 30 minutes using MetaMorph and ImageJ software Bethesda, Md.). The integrity of cell growth conditions over the course of 7 days on the array will be validated by comparing population doublings to standard culture conditions in a 15 cm plate.

Example 8—Expose Arrayed Cells to Drug Compounds and Assess Survival Rates Vs. Time and Dosage Acute myeloid leukemia (AML) cells bearing internal tandem duplication (ITD) mutations in FMS-like tyrosine kinase 3 (FLT3) will be used. FLT3-ITD mutations are the most common mutations in AML and drive constitutive cell growth and survival. As such, FLT3-ITD+ AMLs are highly sensitive to treatment with small molecule FLT3 inhibitors. Unfortunately, resistance to FLT3 inhibitor treatment emerges rapidly in nearly all patients owing to the pre-existence of drug resistant clones harboring either "gate-keeper" mutations in FLT3-ITD (F691L) or kinase activation loop mutations at residues D835 or Y842, all of which block drug binding. Thus, populations of FLT3-ITD+ AML cells from both patients and established cell lines are characterized by a majority of cells that are drug-sensitive and a minority of cells (<1%) that are profoundly drug resistant owing to the presence of the drug binding mutants above.

MV4;11 AML cells expressing FLT3-ITD and exhibiting growth inhibition-50% (GI50) values of ~10 nM when treated with the first generation, approved FLT3 inhibitor Quizartinib, will be magnetically labeled with antibodies against the cell surface marker CD33. Cells will then be sorted into individual apartments and cultured in media containing either DMSO vehicle or Quizartinib at concentrations of 1, 10, 25, 50, and 100 nM. The number of cells in each apartment will be counted daily for up to 7 days using automated microscopy. Histograms representing the distribution of cell numbers per apartment will be calculated as a function of time and dose, where vehicle treated populations will be expected to yield a unimodal distribution with increasing mean value and breadth over time, whereas drug treated populations will be expected to yield bimodal distributions, one of which includes the majority drug sensitive cells and exhibits a nearly constant mean value and narrow distribution as cells undergo growth arrest or death over time, and the second of which includes the minority drug resistant cells and exhibits an increasing mean value as cells proliferate over time. The frequency of cells in the MV4;11 line with FLT3-ITD gatekeeper mutations is expected to lie in the 0.1-1% range, thus yielding 1-10 drug resistant apartments within the total set of ~1,600. The true frequency of gatekeeper mutations will be verified by deep sequencing of the FLT3 allele in the cell line prior to the experiment, and if this frequency is lower than expected, the population will be "spiked" with ~1% of cells stably expressing an ectopic FLT3-ITD (F691L) mutant, resistance-conferring construct.

Example 9—Array of Cells after Hydrodynamic Trapping and Acoustic Transfer

Figure 41:
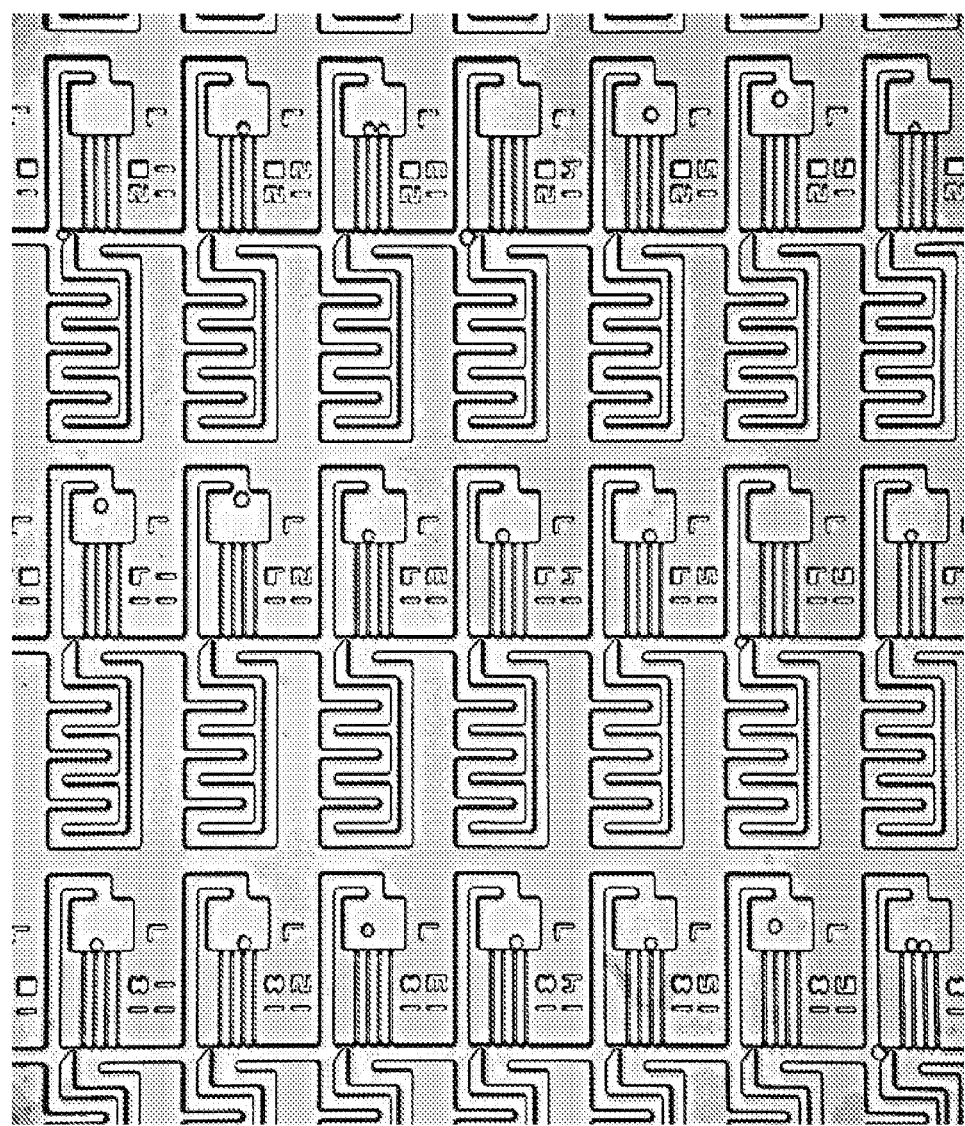
FIG. 41 shows an array of fluidic traps and adjacent partitions configured for acoustic transfer.

FIG. 41 shows an array of hydrodynamic traps and adjacent partitions and also shows the location of single cells after hydrodynamic trapping and acoustic transfer into adjacent partitions. The acoustic transfer was achieved by applying an acoustic source to the array having a driving frequency of 2.90 MHz. Following acoustic transfer, 75% of the plurality of partitions in the array achieved single cell occupancy.

Example 10—Comparing Flow Patterns Under Acoustic Stimuli

Figure 42A:
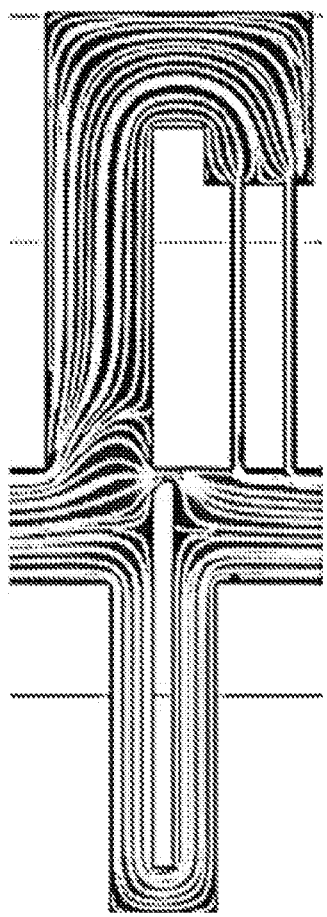
FIG. 42a-c shows COMSOL calculations for flow profiles at a trifuration in (a), and fluorescent tracer particles of the flow profile are shown in the absence of an acoustic signal (b) and presence of an acoustic signal (c), showing the effect of acoustic streaming at sharp corners and beam like structures.
Figure 42B:
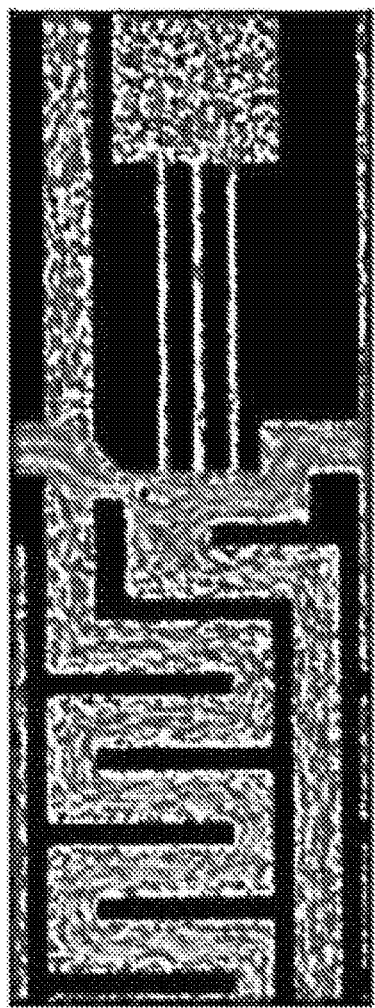
Figure 42C:
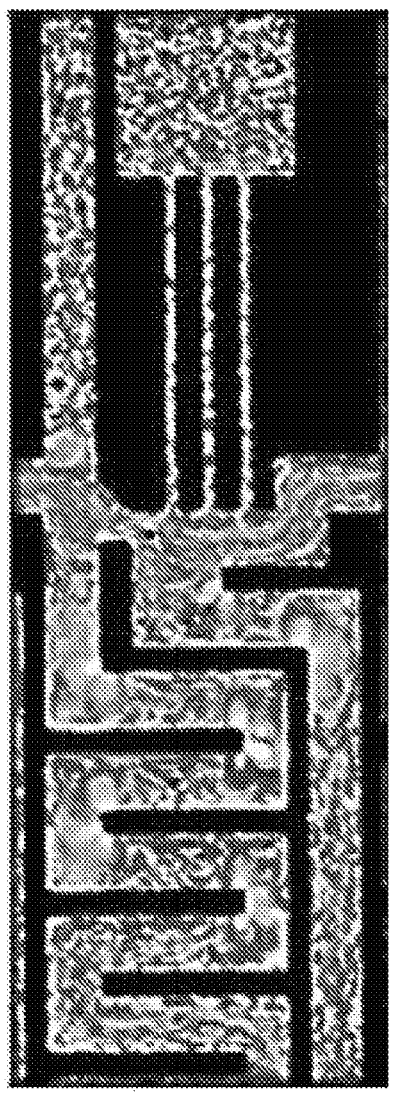

FIG. 42a shows COMSOL calculations for flow profiles at a trifurcation in a device. The flow patterns of the COMSOL calculations were compared to flow patterns visualized in an experiment using 300 nm fluorescent tracer particles when an acoustic field was not applied to the trifurcation (FIG. 42b) and when an acoustic field was applied to the trifurcation (FIG. 42c). The flow pattern of the COMSOL calculation was similar to the flow pattern of the tracer particles when the acoustic field was not applied. The flow pattern of the tracer particles changed when the acoustic field was applied, in which vortices were observed at the corners of the microchannels and at the entrance to the partition. The vortices that were generated from the acoustic streaming were the fluidic forces that pushed the cells into the partitions by the acoustic streaming.

Example 11—Expose Arrayed Latently Infected Human Immunodeficiency Virus (HIV) Cells to Drug Compounds and Assess Activation Percentages Vs. Time and Immune Mechanisms for Clearing Activated Cells Cells with latent human immunodeficiency virus (HIV)-1 infection may be well recognized as a barrier to curing HIV. However, immunological silence of these cells can make it difficult to test therapeutic strategies, such as a "shock and kill" approach to enhance the immune system's ability to clear the infection. As the estimated latent pool in an antiretroviral therapy (ART)-suppressed patient may be expected to be in the range from about 0.1% to about 0.001%, single cell analysis tools are needed to observe these exceedingly rare cellular events and to enable the formation of cell pairs to study the immune mechanisms to clear the activated cells. Histone deacetylase (HDAC) inhibitors have been shown to activate HIV transcription in latent cells and induce the production of proteins necessary for their recognition and targeted elimination. However, the activation rates may be difficult to study in detail due to their extreme rarity. A device or system as described herein can (a) form an array of latent cells, (b) deliver multiple exposures of the arrayed cells to compounds (such as anti-latency compounds), (c) develop virion microwell biological sensors to quantify replication competent viral reservoirs, (d) form CD8/CD4 single cell pairs to recreate a bulk cytolytic assay at single cell resolution, or (e) any combination thereof.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A method comprising:
    a) capturing a first set of one or more objects in one or more hydrodynamic traps, wherein the one or more hydrodynamic traps are formed within a microfluidic device;
    b) turning off a fluid flow from the one or more hydrodynamic traps into one or more partitions, wherein the one or more partitions are adjacent to the one or more hydrodynamic traps and are also formed within the microfluidic device;
    c) selectively or collectively transferring at least a subset of the first set of one or more objects from the one or more hydrodynamic traps into the one or more partitions using a transfer mechanism, wherein the fluid flow remains off during the selectively or collectively transferring, and wherein the transfer mechanism is a magnetic transfer mechanism, an acoustic transfer mechanism, or a combination thereof.

2. The method of claim 1, further comprising, after the transferring in step (c), the steps of:
    d) starting the fluid flow from the one or more hydrodynamic traps into one or more partitions;
    e) capturing at least a second set of one or more objects in the one or more hydrodynamic traps, and
    f) selectively or collectively transferring at least a subset of the at least second set of one or more objects into the one or more partitions using the transfer mechanism.

3. The method of claim 2, further comprising the step of:
    g) removing the subset of the first set of one or more objects from the one or more partitions using the transfer mechanism.

4. The method of claim 1, wherein the first set of one or more objects comprises cells, and further comprising the steps of:
    d) introducing a compound into at least one of the one or more partitions, using the transfer mechanism; and
    e) quantifying a biological response within at least one of the one or more partitions.

5. The method of claim 1, wherein the transfer mechanism comprises a magnetic transfer mechanism that comprises the use of one or more magnets and a magnetic track disposed within the microfluidic device.

6. The method of claim 1, wherein the one or more partitions comprise structural resonance features, and wherein the selecting the transfer mechanism comprises selecting the acoustic transfer mechanism, and wherein the acoustic transfer mechanism comprises using acoustic energy that produces a standing acoustic wave within the microfluidic device.

7. The method of claim 1, wherein the selecting the transfer mechanism comprises selecting the acoustic transfer mechanism, and wherein the acoustic transfer mechanism comprises using an acoustic energy source that provides acoustic streaming within the microfluidic device.

* * * * *